US012562273B2

(12) United States Patent
Bernstein et al.

(10) Patent No.: US 12,562,273 B2
(45) Date of Patent: Feb. 24, 2026

(54) MEDICAL DEVICES AND METHODS

(71) Applicant: ABBOTT DIABETES CARE INC.,
Alameda, CA (US)

(72) Inventors: Daniel Milfred Bernstein, El Granada,
CA (US); Martin J. Fennell, Concord,
CA (US); Christopher Allen Thomas,
Cheltenham (GB); Udo Hoss, San
Ramon, CA (US); **Gary Ashley
Stafford, Hayward, CA (US); Phillip
Yee**, San Francisco, CA (US);
Jean-Pierre Cole, Tracy, CA (US);
Jeffery Mario Sicurello, Union City,
CA (US)

(73) Assignee: ABBOTT DIABETES CARE INC.,
Alameda, CA (US)

( * ) Notice: Subject to any disclaimer, the term of this
patent is extended or adjusted under 35
U.S.C. 154(b) by 0 days.

(21) Appl. No.: 18/912,508

(22) Filed: Oct. 10, 2024

(65) Prior Publication Data
US 2025/0037855 A1     Jan. 30, 2025

Related U.S. Application Data

(63) Continuation of application No. 18/130,381, filed on
Apr. 3, 2023, now abandoned, which is a continuation
(Continued)

(51) Int. Cl.
*G16H 40/67* (2018.01)
*A61B 5/00* (2006.01)
(Continued)

(52) U.S. Cl.
CPC ........... *G16H 40/67* (2018.01); *A61B 5/0017*
(2013.01); *A61B 5/0022* (2013.01); *A61B 5/01*
(2013.01);
(Continued)

(58) Field of Classification Search
CPC ...... G16H 40/67; G16H 40/63; A61B 5/0017;
A61B 5/0022; A61B 5/01; A61B
5/14532;
(Continued)

(56) References Cited

U.S. PATENT DOCUMENTS 2,892,990 A     6/1959  Werndl
3,180,221 A     4/1965  Porter
(Continued)

FOREIGN PATENT DOCUMENTS

AU     2003/259741        2/2004
CA         2291105 A1   12/1998
(Continued)

OTHER PUBLICATIONS

U.S. Appl. No. 60/587,787, filed Jul. 13, 2004, Brister et al.
(Continued)

*Primary Examiner* — Navin Natnithithadha
(74) *Attorney, Agent, or Firm* — ONE LLP

(57) ABSTRACT

Methods and devices to monitor an analyte in body fluid are
provided. Embodiments include continuous or discrete
acquisition of analyte related data from a transcutaneously
positioned in vivo analyte sensor automatically or upon
request from a user. The in vivo analyte sensor is coupled to
an electronics unit holding a memory with instruction to
cause processing circuitry to initiate a predetermined time
period that is longer than a predetermined life of the sensor,
during the predetermined time period, convert signals from
the sensor related to glucose to respective corresponding
glucose levels, without relying on any post-manufacture
independent analyte measurements from a reference device,
and at the expiration of the predetermined time period,
disable, deactivate, or cease use of one or more feature.

10 Claims, 25 Drawing Sheets

Related U.S. Application Data of application No. 18/176,293, filed on Feb. 28, 2023, now Pat. No. 12,315,630, which is a continuation of application No. 17/864,931, filed on Jul. 14, 2022, now abandoned, which is a continuation of application No. 16/700,799, filed on Dec. 2, 2019, which is a continuation of application No. 14/841,224, filed on Aug. 31, 2015, now Pat. No. 10,492,685, which is a continuation of application No. 12/807,278, filed on Aug. 31, 2010, now Pat. No. 10,136,816.

(60) Provisional application No. 61/299,924, filed on Jan. 29, 2010, provisional application No. 61/291,326, filed on Dec. 30, 2009, provisional application No. 61/256,925, filed on Oct. 30, 2009, provisional application No. 61/247,508, filed on Sep. 30, 2009, provisional application No. 61/247,519, filed on Sep. 30, 2009, provisional application No. 61/247,514, filed on Sep. 30, 2009, provisional application No. 61/238,581, filed on Aug. 31, 2009.

(51) Int. Cl.

| | |
|---|---|
| *A61B 5/01* | (2006.01) |
| *A61B 5/145* | (2006.01) |
| *A61B 5/1486* | (2006.01) |
| *G01N 33/487* | (2006.01) |
| *G16H 40/63* | (2018.01) |

(52) U.S. Cl.
CPC ........ *A61B 5/14532* (2013.01); *A61B 5/1486* (2013.01); *A61B 5/72* (2013.01); *G01N 33/48792* (2013.01); *G16H 40/63* (2018.01); *A61B 2560/0238* (2013.01); *Y02A 90/10* (2018.01)

(58) Field of Classification Search
CPC . A61B 5/1486; A61B 5/72; A61B 2560/0238; G01N 33/48792; Y02A 90/10; G06Q 50/22
USPC .......................................... 600/309, 345–366
See application file for complete search history.

(56) References Cited

U.S. PATENT DOCUMENTS

| | | | |
|---|---|---|---|
| 3,320,954 | A | 5/1967 | Cowley |
| 3,581,062 | A | 5/1971 | Aston |
| 3,926,760 | A | 12/1975 | Allen et al. |
| 3,949,388 | A | 4/1976 | Fuller |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,286,039 | A | 8/1981 | Landa et al. |
| 4,327,725 | A | 5/1982 | Cortese et al. |
| 4,344,438 | A | 8/1982 | Schultz |
| 4,349,728 | A | 9/1982 | Phillips et al. |
| 4,373,527 | A | 2/1983 | Fischell |
| 4,392,849 | A | 7/1983 | Petre et al. |
| 4,425,920 | A | 1/1984 | Bourland et al. |
| 4,431,004 | A | 2/1984 | Bessman et al. |
| 4,478,976 | A | 10/1984 | Goertz et al. |
| 4,494,950 | A | 1/1985 | Fischell |
| 4,509,531 | A | 4/1985 | Ward |
| 4,527,240 | A | 7/1985 | Kvitash |
| 4,538,616 | A | 9/1985 | Rogoff |
| 4,545,382 | A | 10/1985 | Higgins et al. |
| 4,561,443 | A | 12/1985 | Hogrefe et al. |
| 4,561,963 | A | 12/1985 | Owen et al. |
| 4,619,793 | A | 10/1986 | Lee |
| 4,639,062 | A | 1/1987 | Taniguchi et al. |
| 4,671,288 | A | 6/1987 | Gough |
| 4,675,346 | A | 6/1987 | Lin et al. |
| 4,684,245 | A | 8/1987 | Goldring |
| 4,703,324 | A | 10/1987 | White |
| 4,703,756 | A | 11/1987 | Gough et al. |
| 4,711,245 | A | 12/1987 | Higgins et al. |
| 4,731,726 | A | 3/1988 | Allen, III |
| 4,749,985 | A | 6/1988 | Corsberg |
| 4,752,935 | A | 6/1988 | Beck |
| 4,757,022 | A | 7/1988 | Shults et al. |
| 4,777,953 | A | 10/1988 | Ash et al. |
| 4,779,618 | A | 10/1988 | Mund et al. |
| 4,818,994 | A | 4/1989 | Orth et al. |
| 4,854,322 | A | 8/1989 | Ash et al. |
| 4,861,454 | A | 8/1989 | Ushizawa et al. |
| 4,871,351 | A | 10/1989 | Feingold |
| 4,890,620 | A | 1/1990 | Gough |
| 4,924,879 | A | 5/1990 | O'Brien |
| 4,925,268 | A | 5/1990 | Iyer et al. |
| 4,953,552 | A | 9/1990 | DeMarzo |
| 4,986,271 | A | 1/1991 | Wilkins |
| 4,995,402 | A | 2/1991 | Smith et al. |
| 5,000,180 | A | 3/1991 | Kuypers et al. |
| 5,002,054 | A | 3/1991 | Ash et al. |
| 5,019,974 | A | 5/1991 | Beckers |
| 5,050,612 | A | 9/1991 | Matsumura |
| 5,051,688 | A | 9/1991 | Murase et al. |
| 5,055,171 | A | 10/1991 | Peck |
| 5,068,536 | A | 11/1991 | Rosenthal |
| 5,082,550 | A | 1/1992 | Rishpon et al. |
| 5,089,112 | A | 2/1992 | Skotheim et al. |
| 5,106,365 | A | 4/1992 | Hernandez |
| 5,122,925 | A | 6/1992 | Inpyn |
| 5,124,661 | A | 6/1992 | Zellin et al. |
| 5,135,004 | A | 8/1992 | Adams et al. |
| 5,162,407 | A | 11/1992 | Turner |
| 5,165,407 | A | 11/1992 | Wilson et al. |
| 5,188,534 | A | 2/1993 | Bertho et al. |
| 5,245,314 | A | 9/1993 | Kah et al. |
| 5,246,867 | A | 9/1993 | Lakowicz et al. |
| 5,259,793 | A | 11/1993 | Yamada et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,267,963 | A | 12/1993 | Bachynsky |
| 5,279,294 | A | 1/1994 | Anderson et al. |
| 5,285,792 | A | 2/1994 | Sjoquist et al. |
| 5,289,497 | A | 2/1994 | Jackobson et al. |
| 5,293,877 | A | 3/1994 | O'Hara et al. |
| 5,299,571 | A | 4/1994 | Mastrototaro |
| 5,305,008 | A | 4/1994 | Turner et al. |
| 5,318,583 | A | 6/1994 | Rabenau et al. |
| 5,320,715 | A | 6/1994 | Berg |
| 5,320,725 | A | 6/1994 | Gregg et al. |
| 5,322,063 | A | 6/1994 | Allen et al. |
| 5,333,615 | A | 8/1994 | Craelius et al. |
| 5,340,722 | A | 8/1994 | Wolfbeis et al. |
| 5,342,408 | A | 8/1994 | deCoriolis et al. |
| 5,342,789 | A | 8/1994 | Chick et al. |
| 5,356,786 | A | 10/1994 | Heller et al. |
| 5,360,404 | A | 11/1994 | Novacek et al. |
| 5,372,133 | A | 12/1994 | Hogen Esch |
| 5,372,427 | A | 12/1994 | Padovani et al. |
| 5,379,238 | A | 1/1995 | Stark |
| 5,390,671 | A | 2/1995 | Lord et al. |
| 5,391,250 | A | 2/1995 | Cheney, II et al. |
| 5,400,794 | A | 3/1995 | Gorman |
| 5,407,431 | A | 4/1995 | Botich et al. |
| 5,408,999 | A | 4/1995 | Singh et al. |
| 5,410,326 | A | 4/1995 | Goldstein |
| 5,411,647 | A | 5/1995 | Johnson et al. |
| 5,425,868 | A | 6/1995 | Pedersen |
| 5,431,160 | A | 7/1995 | Wilkins |
| 5,431,921 | A | 7/1995 | Thombre |
| 5,462,051 | A | 10/1995 | Oka et al. |
| 5,462,645 | A | 10/1995 | Albery et al. |
| 5,472,317 | A | 12/1995 | Field et al. |
| 5,482,473 | A | 1/1996 | Lord et al. |

(56)  References Cited

U.S. PATENT DOCUMENTS

| | | |
|---|---|---|
| 5,489,414 A | 2/1996 | Schreiber et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,821 A | 5/1996 | Bae et al. |
| 5,529,676 A | 6/1996 | Maley et al. |
| 5,531,878 A | 7/1996 | Vadgama et al. |
| 5,532,686 A | 7/1996 | Urbas et al. |
| 5,543,326 A | 8/1996 | Heller et al. |
| 5,544,196 A | 8/1996 | Tiedmann, Jr. et al. |
| 5,558,638 A | 9/1996 | Evers et al. |
| 5,568,806 A | 10/1996 | Cheney, II et al. |
| 5,569,186 A | 10/1996 | Lord et al. |
| 5,581,206 A | 12/1996 | Chevallier et al. |
| 5,582,184 A | 12/1996 | Erickson et al. |
| 5,584,813 A | 12/1996 | Livingston et al. |
| 5,586,553 A | 12/1996 | Halili et al. |
| 5,591,137 A | 1/1997 | Stevens |
| 5,593,852 A | 1/1997 | Heller et al. |
| 5,600,301 A | 2/1997 | Robinson, III |
| 5,601,435 A | 2/1997 | Quy |
| 5,609,575 A | 3/1997 | Larson et al. |
| 5,623,933 A | 4/1997 | Amano et al. |
| 5,628,310 A | 5/1997 | Rao et al. |
| 5,628,890 A | 5/1997 | Carter et al. |
| 5,634,468 A | 6/1997 | Platt et al. |
| 5,653,239 A | 8/1997 | Pompei et al. |
| 5,659,454 A | 8/1997 | Vermesse |
| 5,660,163 A | 8/1997 | Schulman et al. |
| 5,665,222 A | 9/1997 | Heller et al. |
| 5,673,694 A | 10/1997 | Rivers |
| 5,690,119 A | 11/1997 | Rytky et al. |
| 5,700,360 A | 12/1997 | Chan et al. |
| 5,707,502 A | 1/1998 | McCaffrey et al. |
| 5,711,001 A | 1/1998 | Bussan et al. |
| 5,711,685 A | 1/1998 | Wood |
| 5,711,861 A | 1/1998 | Ward et al. |
| 5,724,030 A | 3/1998 | Urbas et al. |
| 5,733,259 A | 3/1998 | Valcke et al. |
| 5,733,313 A | 3/1998 | Barreras, Sr. et al. |
| 5,735,285 A | 4/1998 | Albert et al. |
| 5,748,103 A | 5/1998 | Flach et al. |
| 5,749,907 A | 5/1998 | Mann |
| 5,758,290 A | 5/1998 | Nealon et al. |
| 5,763,787 A | 6/1998 | Gravel et al. |
| 5,770,028 A | 6/1998 | Maley et al. |
| 5,770,208 A | 6/1998 | Fattom et al. |
| 5,772,586 A | 6/1998 | Heinonen et al. |
| 5,778,879 A | 7/1998 | Ota et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,804,047 A | 9/1998 | Karube et al. |
| 5,820,551 A | 10/1998 | Hill et al. |
| 5,822,715 A | 10/1998 | Worthington et al. |
| 5,823,802 A | 10/1998 | Bartley |
| 5,830,064 A | 11/1998 | Bradish et al. |
| 5,833,603 A | 11/1998 | Kovacs et al. |
| 5,842,473 A | 12/1998 | Fenster et al. |
| 5,856,758 A | 1/1999 | Joffe et al. |
| 5,891,049 A | 4/1999 | Cyrus et al. |
| 5,899,855 A | 5/1999 | Brown |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,045,671 A | 4/2000 | Wu et al. |
| 6,049,727 A | 4/2000 | Crothall |
| 6,052,565 A | 4/2000 | Ishikura et al. |
| 6,071,391 A | 6/2000 | Gotoh et al. |
| 6,081,736 A | 6/2000 | Colvin et al. |
| 6,083,710 A | 7/2000 | Heller et al. |
| 6,085,342 A | 7/2000 | Marholev et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,268 A | 8/2000 | Inbar |
| 6,096,364 A | 8/2000 | Bok et al. |
| 6,097,480 A | 8/2000 | Kaplan |
| 6,103,033 A | 8/2000 | Say et al. |
| 6,106,484 A | 8/2000 | Terwilliger et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,149,626 A | 11/2000 | Bachynsky et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,180,221 B1 | 1/2001 | Crotzer et al. |
| 6,198,946 B1 | 3/2001 | Shin et al. |
| 6,198,969 B1 | 3/2001 | Kuzma |
| 6,200,265 B1 | 3/2001 | Walsh et al. |
| 6,203,354 B1 | 3/2001 | Kuwahara et al. |
| 6,203,495 B1 | 3/2001 | Bardy et al. |
| 6,212,416 B1 | 4/2001 | Ward et al. |
| 6,212,417 B1 | 4/2001 | Ikeda et al. |
| 6,219,574 B1 | 4/2001 | Cormier et al. |
| 6,233,471 B1 | 5/2001 | Berner et al. |
| 6,237,394 B1 | 5/2001 | Harris et al. |
| 6,248,067 B1 | 6/2001 | Causey, III et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,304,766 B1 | 10/2001 | Colvin, Jr. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,336,269 B1 | 1/2002 | Eldridge et al. |
| 6,338,790 B1 | 1/2002 | Feldman et al. |
| 6,340,588 B1 | 1/2002 | Nova et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,377,829 B1 | 4/2002 | Al-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |

(56)  References Cited

U.S. PATENT DOCUMENTS

| | | | |
|---|---|---|---|
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,478,736 B1 | 11/2002 | Mault |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,498,941 B1 | 12/2002 | Jackson |
| 6,503,381 B1 | 1/2003 | Gotoh et al. |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,603,995 B1 | 8/2003 | Carter |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,178 B1 | 11/2003 | Junker et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,668,196 B1 | 12/2003 | Villegas et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,850,859 B1 | 2/2005 | Schuh |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,965,791 B1 | 11/2005 | Hitchcock et al. |
| 6,968,294 B2 | 11/2005 | Gutta et al. |
| 6,971,274 B2 | 12/2005 | Olin |
| 6,973,706 B2 | 12/2005 | Say et al. |
| 6,974,437 B2 | 12/2005 | Lebel et al. |
| 6,983,867 B1 | 1/2006 | Fugere |
| 6,986,756 B2 | 1/2006 | Pelkey et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,020,508 B2 | 3/2006 | Stivoric et al. |
| 7,022,072 B2 | 4/2006 | Fox et al. |
| 7,024,236 B2 | 4/2006 | Ford et al. |
| 7,024,245 B2 | 4/2006 | Lebel et al. |
| 7,027,859 B1 | 4/2006 | McNichols et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |

(56)                References Cited

U.S. PATENT DOCUMENTS

| | | | |
|---|---|---|---|
| 7,074,307 B2 | 7/2006 | Simpson et al. |
| 7,081,195 B2 | 7/2006 | Simpson et al. |
| 7,082,334 B2 | 7/2006 | Boute et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,124,027 B1 | 10/2006 | Ernst et al. |
| 7,125,382 B2 | 10/2006 | Zhou et al. |
| 7,134,999 B2 | 11/2006 | Brauker et al. |
| 7,136,689 B2 | 11/2006 | Shults et al. |
| 7,154,398 B2 | 12/2006 | Chen et al. |
| 7,155,290 B2 | 12/2006 | Von Arx et al. |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |
| 7,287,318 B2 | 10/2007 | Bhullar et al. |
| 7,291,497 B2 | 11/2007 | Holmes et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,344,500 B2 | 3/2008 | Talbot et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,384,397 B2 | 6/2008 | Zhang et al. |
| 7,386,937 B2 | 6/2008 | Bhullar et al. |
| 7,387,010 B2 | 6/2008 | Sunshine et al. |
| 7,399,277 B2 | 7/2008 | Saidara et al. |
| 7,401,111 B1 | 7/2008 | Batman et al. |
| 7,402,153 B2 | 7/2008 | Steil et al. |
| 7,404,796 B2 | 7/2008 | Ginsberg |
| 7,408,132 B2 | 8/2008 | Wambsganss et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,525,315 B2 | 4/2009 | Fredette et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,582,059 B2 | 9/2009 | Funderburk et al. |
| 7,583,990 B2 | 9/2009 | Goode, Jr. et al. |
| 7,585,287 B2 | 9/2009 | Bresina et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,660,615 B2 | 2/2010 | VanAntwerp et al. |
| 7,668,596 B2 | 2/2010 | Von Arx et al. |
| 7,697,967 B2 | 4/2010 | Stafford |
| 7,699,775 B2 | 4/2010 | Desai et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,731,691 B2 | 6/2010 | Cote et al. |
| 7,741,734 B2 | 6/2010 | Joannopoulos et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,846,132 B2 | 12/2010 | Gravesen et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,885,698 B2 | 2/2011 | Feldman |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,946,984 B2 | 5/2011 | Brister et al. |
| 7,951,080 B2 | 5/2011 | Taub |
| 7,955,258 B2 | 6/2011 | Goscha et al. |
| 7,970,448 B2 | 6/2011 | Shults et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,999,674 B2 | 8/2011 | Kamen |
| 8,000,918 B2 | 8/2011 | Fjield et al. |
| 8,028,837 B2 | 10/2011 | Gerstle et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |

(56) References Cited

U.S. PATENT DOCUMENTS

| | | | |
|---|---|---|---|
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,175,673 B2 | 5/2012 | Say et al. |
| 8,179,266 B2 | 5/2012 | Hermle |
| 8,219,173 B2 | 7/2012 | Budiman et al. |
| 8,323,251 B2 | 12/2012 | West et al. |
| 8,346,335 B2 | 1/2013 | Harper et al. |
| 8,538,512 B1 | 9/2013 | Bibian et al. |
| 8,617,069 B2 | 12/2013 | Bernstein et al. |
| 8,747,363 B2 | 6/2014 | Nielsen et al. |
| 8,750,955 B2 | 6/2014 | Brister et al. |
| 8,764,657 B2 | 7/2014 | Curry et al. |
| 8,808,515 B2 | 8/2014 | Feldman et al. |
| 9,186,098 B2 | 11/2015 | Lee et al. |
| 9,215,992 B2 | 12/2015 | Donnay et al. |
| 9,241,631 B2 | 1/2016 | Valdes et al. |
| 9,265,453 B2 | 2/2016 | Curry et al. |
| 9,351,669 B2 | 5/2016 | Stafford |
| 9,402,570 B2 | 8/2016 | Pace et al. |
| 9,504,471 B2 | 11/2016 | Vaitekunas et al. |
| 9,566,384 B2 | 2/2017 | Gyrn et al. |
| 9,668,682 B2 | 6/2017 | Brister et al. |
| 9,687,183 B2 | 6/2017 | Donnay et al. |
| 9,750,444 B2 | 9/2017 | Stafford |
| 9,808,574 B2 | 11/2017 | Yodfat et al. |
| 10,010,280 B2 | 7/2018 | Donnay et al. |
| 10,136,816 B2* | 11/2018 | Bernstein ........... A61B 5/14532 |
| 10,292,632 B2 | 5/2019 | Lee et al. |
| 10,492,685 B2* | 12/2019 | Bernstein ............. A61B 5/0017 |
| 10,765,351 B2 | 9/2020 | Stafford |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,340 B2 | 1/2021 | Curry et al. |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,952,657 B2 | 3/2021 | Curry et al. |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 10,993,642 B2 | 5/2021 | Simpson et al. |
| 11,000,213 B2 | 5/2021 | Kamath et al. |
| 11,000,216 B2 | 5/2021 | Curry et al. |
| 11,013,440 B2 | 5/2021 | Lee et al. |
| 11,058,334 B1 | 7/2021 | Curry et al. |
| 11,064,917 B2 | 7/2021 | Simpson et al. |
| 11,064,922 B1 | 7/2021 | Curry et al. |
| 11,141,084 B2 | 10/2021 | Funderburk et al. |
| 11,202,591 B2 | 12/2021 | Yee et al. |
| 11,246,519 B2 | 2/2022 | Donnay et al. |
| 11,259,725 B2 | 3/2022 | Stafford |
| 11,266,335 B2 | 3/2022 | Donnay et al. |
| 11,510,625 B2 | 11/2022 | Gray et al. |
| 12,070,313 B2* | 8/2024 | Alonso-Soski ........ A61B 5/685 |
| 2001/0016682 A1 | 8/2001 | Berner et al. |
| 2001/0020546 A1 | 9/2001 | Eldridge et al. |
| 2001/0037060 A1 | 11/2001 | Thompson et al. |

| | | | |
|---|---|---|---|
| 2001/0037366 A1 | 11/2001 | Webb et al. |
| 2001/0047127 A1 | 11/2001 | New et al. |
| 2002/0013522 A1 | 1/2002 | Lav et al. |
| 2002/0013538 A1 | 1/2002 | Teller |
| 2002/0019022 A1 | 2/2002 | Dunn et al. |
| 2002/0019584 A1 | 2/2002 | Schulze et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0026108 A1 | 2/2002 | Arthur, Jr. |
| 2002/0032531 A1 | 3/2002 | Mansky et al. |
| 2002/0039026 A1 | 4/2002 | Stroth et al. |
| 2002/0042090 A1 | 4/2002 | Heller et al. |
| 2002/0045808 A1 | 4/2002 | Ford et al. |
| 2002/0049482 A1 | 4/2002 | Fabian et al. |
| 2002/0050250 A1 | 5/2002 | Peterson et al. |
| 2002/0057993 A1 | 5/2002 | Maisey et al. |
| 2002/0065454 A1 | 5/2002 | Lebel et al. |
| 2002/0072784 A1 | 6/2002 | Sheppard et al. |
| 2002/0074162 A1 | 6/2002 | Su et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0103499 A1 | 8/2002 | Perez et al. |
| 2002/0106709 A1 | 8/2002 | Potts et al. |
| 2002/0118528 A1 | 8/2002 | Su et al. |
| 2002/0119711 A1 | 8/2002 | VanAntwerp et al. |
| 2002/0128594 A1 | 9/2002 | Das et al. |
| 2002/0161288 A1 | 10/2002 | Shin et al. |
| 2002/0164836 A1 | 11/2002 | Ho |
| 2002/0169439 A1 | 11/2002 | Flaherty |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0197522 A1 | 12/2002 | Lawrence et al. |
| 2003/0004403 A1 | 1/2003 | Drinan et al. |
| 2003/0020477 A1 | 1/2003 | Goldstein |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0065308 A1 | 4/2003 | Lebel et al. |
| 2003/0076792 A1 | 4/2003 | Theimer |
| 2003/0078481 A1 | 4/2003 | McIvor et al. |
| 2003/0088166 A1 | 5/2003 | Say et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0114898 A1 | 6/2003 | Von Arx et al. |
| 2003/0119457 A1 | 6/2003 | Standke |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0144579 A1 | 7/2003 | Buss |
| 2003/0144581 A1 | 7/2003 | Conn et al. |
| 2003/0153900 A1 | 8/2003 | Aceti et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199790 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak et al. |
| 2003/0225373 A1 | 12/2003 | Bobroff et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0030226 A1 | 2/2004 | Quy |

(56) References Cited

U.S. PATENT DOCUMENTS

| | | |
|---|---|---|
| 2004/0030531 A1 | 2/2004 | Miller et al. |
| 2004/0030581 A1 | 2/2004 | Levin et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106860 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176669 A1 | 9/2004 | Arthur, Jr. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0221057 A1 | 11/2004 | Darcey et al. |
| 2004/0223876 A1 | 11/2004 | Kirollos et al. |
| 2004/0225199 A1 | 11/2004 | Evanyk et al. |
| 2004/0225338 A1 | 11/2004 | Lebel et al. |
| 2004/0236200 A1 | 11/2004 | Say et al. |
| 2004/0240426 A1 | 12/2004 | Wu et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0009379 A1 | 1/2005 | Huang et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0112169 A1 | 5/2005 | Brauker et al. |
| 2005/0112544 A1 | 5/2005 | Xu et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0171442 A1 | 8/2005 | Shirasaki et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0215871 A1 | 9/2005 | Feldman et al. |
| 2005/0221504 A1 | 10/2005 | Petruno et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0240245 A1 | 10/2005 | Bange et al. |
| 2005/0241957 A1 | 11/2005 | Mao et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0277164 A1 | 12/2005 | Drucker et al. |
| 2005/0283114 A1 | 12/2005 | Bresina et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0004270 A1 | 1/2006 | Bedard et al. |
| 2006/0004272 A1 | 1/2006 | Shah et al. |
| 2006/0009727 A1 | 1/2006 | O'Mahony et al. |
| 2006/0010098 A1 | 1/2006 | Goodnow et al. |
| 2006/0011474 A1 | 1/2006 | Schulein et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040793 A1 | 2/2006 | Martens et al. |
| 2006/0042080 A1 | 3/2006 | Say et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0129733 A1 | 6/2006 | Solbelman |
| 2006/0142651 A1 | 6/2006 | Brister et al. |

(56)  References Cited

U.S. PATENT DOCUMENTS

| | | |
|---|---|---|
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0178022 A1 | 8/2006 | Liu |
| 2006/0178625 A1 | 8/2006 | Lim et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0220839 A1 | 10/2006 | Fifolt et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0272652 A1 | 12/2006 | Stocker et al. |
| 2006/0276714 A1 | 12/2006 | Holt et al. |
| 2006/0276771 A1 | 12/2006 | Galley et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088300 A1 | 4/2007 | Cline et al. |
| 2007/0090511 A1 | 4/2007 | Borland et al. |
| 2007/0093754 A1 | 4/2007 | Mogensen et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0111196 A1 | 5/2007 | Alarcon et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0197889 A1 | 8/2007 | Brister et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255125 A1 | 11/2007 | Moberg et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0033268 A1 | 2/2008 | Stafford et al. |
| 2008/0033273 A1 | 2/2008 | Zhou et al. |
| 2008/0039702 A1 | 2/2008 | Hayter et al. |
| 2008/0045824 A1 | 2/2008 | Tapsak et al. |
| 2008/0055070 A1 | 3/2008 | Bange et al. |
| 2008/0058625 A1 | 3/2008 | McGarraugh et al. |
| 2008/0059133 A1 | 3/2008 | Edwards et al. |
| 2008/0059227 A1 | 3/2008 | Clapp |
| 2008/0060955 A1 | 3/2008 | Goodnow |
| 2008/0062055 A1 | 3/2008 | Cunningham et al. |
| 2008/0064937 A1 | 3/2008 | McGarraugh et al. |
| 2008/0064943 A1 | 3/2008 | Talbot et al. |
| 2008/0064944 A1 | 3/2008 | VanAntwerp et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0102441 A1 | 5/2008 | Chen et al. |
| 2008/0108942 A1 | 5/2008 | Brister et al. |
| 2008/0114280 A1 | 5/2008 | Stafford |
| 2008/0119705 A1 | 5/2008 | Patel et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0179187 A1 | 7/2008 | Ouyang |

(56) References Cited

U.S. PATENT DOCUMENTS

| | | |
|---|---|---|
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilersen et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0269719 A1 | 10/2008 | Balgobin et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281179 A1 | 11/2008 | Fennell et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054748 A1 | 2/2009 | Feldman et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0076356 A1 | 3/2009 | Simpson et al. |
| 2009/0076359 A1 | 3/2009 | Peyser et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0085873 A1 | 4/2009 | Betts et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0197440 A1 | 8/2009 | Hirata et al. |
| 2009/0198118 A1 | 8/2009 | Hayter et al. |
| 2009/0198186 A1 | 8/2009 | Mernoe et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0234212 A1 | 9/2009 | Slomski et al. |
| 2009/0240120 A1 | 9/2009 | Mensinger et al. |
| 2009/0240121 A1 | 9/2009 | Bickoff |

(56)　　　　　References Cited

U.S. PATENT DOCUMENTS

| | | |
|---|---|---|
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0299301 A1 | 12/2009 | Gottlieb et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081905 A1 | 4/2010 | Bommakanti et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121169 A1 | 5/2010 | Petisce et al. |
| 2010/0145377 A1 | 6/2010 | Lai et al. |
| 2010/0152548 A1 | 6/2010 | Koski |
| 2010/0152554 A1 | 6/2010 | Steine et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0168660 A1 | 7/2010 | Galley et al. |
| 2010/0190435 A1 | 7/2010 | Cook et al. |
| 2010/0191087 A1 | 7/2010 | Talbot et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0213080 A1 | 8/2010 | Celentano et al. |
| 2010/0228111 A1 | 9/2010 | Friman et al. |
| 2010/0230285 A1 | 9/2010 | Hoss et al. |
| 2010/0235439 A1 | 9/2010 | Goodnow et al. |
| 2010/0259543 A1 | 10/2010 | Tarassenko et al. |
| 2010/0267161 A1 | 10/2010 | Wu et al. |
| 2010/0288632 A1 | 11/2010 | Say et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331651 A1 | 12/2010 | Groll |
| 2011/0004085 A1 | 1/2011 | Mensinger et al. |
| 2011/0004276 A1 | 1/2011 | Blair et al. |
| 2011/0015509 A1 | 1/2011 | Peyser |
| 2011/0021889 A1 | 1/2011 | Hoss et al. |
| 2011/0022411 A1 | 1/2011 | Hjelm et al. |
| 2011/0028817 A1 | 2/2011 | Jin et al. |
| 2011/0077469 A1 | 3/2011 | Blocker et al. |
| 2011/0082484 A1 | 4/2011 | Saravia et al. |
| 2011/0097090 A1 | 4/2011 | Cac |
| 2011/0106126 A1 | 5/2011 | Love et al. |
| 2011/0123971 A1 | 5/2011 | Berkowitz et al. |
| 2011/0125040 A1 | 5/2011 | Crawford et al. |
| 2011/0137571 A1 | 6/2011 | Power et al. |
| 2011/0148905 A1 | 6/2011 | Simmons et al. |
| 2011/0152637 A1 | 6/2011 | Kateraas et al. |
| 2011/0178378 A1 | 7/2011 | Brister et al. |
| 2011/0184482 A1 | 7/2011 | Eberman et al. |
| 2011/0184752 A1 | 7/2011 | Ray et al. |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0213225 A1* | 9/2011 | Bernstein ............. A61B 5/1486 |
| | | 600/309 |
| 2011/0230741 A1 | 9/2011 | Liang et al. |
| 2011/0257495 A1 | 10/2011 | Hoss et al. |
| 2011/0257895 A1 | 10/2011 | Brauker et al. |
| 2011/0263959 A1 | 10/2011 | Young et al. |
| 2011/0264378 A1 | 10/2011 | Breton et al. |
| 2011/0287528 A1 | 11/2011 | Fern et al. |
| 2011/0288574 A1 | 11/2011 | Curry et al. |
| 2011/0319729 A1 | 12/2011 | Donnay et al. |
| 2011/0320130 A1 | 12/2011 | Valdes et al. |
| 2012/0010642 A1 | 1/2012 | Lee et al. |
| 2012/0116190 A1 | 5/2012 | Iketani et al. |
| 2012/0179113 A1 | 7/2012 | Yokota et al. |
| 2012/0184909 A1 | 7/2012 | Gyrn |
| 2012/0190941 A1 | 7/2012 | Donnay et al. |
| 2012/0190942 A1 | 7/2012 | Donnay et al. |
| 2012/0190943 A1 | 7/2012 | Donnay et al. |
| 2012/0190951 A1 | 7/2012 | Curry et al. |
| 2012/0197098 A1 | 8/2012 | Donnay et al. |
| 2012/0197222 A1 | 8/2012 | Donnay et al. |
| 2012/0265042 A1 | 10/2012 | Neinast et al. |
| 2012/0303043 A1 | 11/2012 | Donnay |
| 2013/0111248 A1 | 5/2013 | Ghesquiere et al. |
| 2013/0150691 A1 | 6/2013 | Pace et al. |
| 2013/0158376 A1* | 6/2013 | Hayter ............... A61B 5/14503 |
| | | 600/347 |
| 2013/0267812 A1 | 10/2013 | Pryor et al. |
| 2014/0121989 A1 | 5/2014 | Kamath et al. |
| 2014/0188053 A1 | 7/2014 | Lundquist |
| 2014/0275898 A1* | 9/2014 | Taub ........................ A61B 5/07 |
| | | 600/347 |
| 2015/0005601 A1 | 1/2015 | Hoss et al. |
| 2015/0025338 A1 | 1/2015 | Lee et al. |
| 2015/0326072 A1 | 11/2015 | Petras et al. |
| 2016/0015267 A1* | 1/2016 | Bernstein ............. A61B 5/1486 |
| | | 600/347 |
| 2016/0015268 A1* | 1/2016 | Bernstein ............. A61B 5/1486 |
| | | 600/347 |
| 2016/0015303 A1* | 1/2016 | Bernstein ......... G01N 33/48792 |
| | | 600/347 |
| 2016/0030078 A1 | 2/2016 | Lee et al. |

(56)        References Cited

U.S. PATENT DOCUMENTS

| | | | |
|---|---|---|---|
| 2016/0128615 A1 | 5/2016 | Curry et al. | |
| 2016/0331283 A1 | 11/2016 | Rao et al. | |
| 2016/0331284 A1 | 11/2016 | Pace | |
| 2017/0020417 A1 | 1/2017 | Stafford | |
| 2017/0112531 A1 | 4/2017 | Schoonmaker et al. | |
| 2017/0127985 A1 | 5/2017 | Thompson et al. | |
| 2017/0340249 A1 | 11/2017 | Stafford | |
| 2018/0235520 A1 | 8/2018 | Rao et al. | |
| 2019/0076073 A1 | 3/2019 | Donnay et al. | |
| 2019/0298240 A1 | 10/2019 | Lee et al. | |
| 2020/0100676 A1* | 4/2020 | Bernstein | A61B 5/14532 |
| 2020/0178899 A1 | 6/2020 | Chae et al. | |
| 2020/0397358 A1 | 12/2020 | Lee et al. | |
| 2020/0405208 A1 | 12/2020 | Lee et al. | |
| 2021/0000399 A1 | 1/2021 | Curry et al. | |
| 2021/0000400 A1 | 1/2021 | Curry et al. | |
| 2021/0007651 A1 | 1/2021 | Donnay et al. | |
| 2021/0022654 A1 | 1/2021 | Curry et al. | |
| 2021/0038137 A1 | 2/2021 | Curry et al. | |
| 2021/0076987 A1 | 3/2021 | Stafford | |
| 2021/0113118 A1 | 4/2021 | Stafford | |
| 2021/0113126 A1 | 4/2021 | Donnay et al. | |
| 2021/0161445 A1 | 6/2021 | Donnay et al. | |
| 2021/0204849 A1 | 7/2021 | Donnay et al. | |
| 2021/0204850 A1 | 7/2021 | Curry et al. | |
| 2021/0204851 A1 | 7/2021 | Curry et al. | |
| 2022/0087580 A1 | 3/2022 | Donnay et al. | |
| 2022/0125358 A1 | 4/2022 | Curry et al. | |
| 2022/0142533 A1 | 5/2022 | Donnay et al. | |
| 2022/0218247 A1 | 7/2022 | Donnay et al. | |
| 2022/0359074 A1* | 11/2022 | Bernstein | A61B 5/0022 |
| 2023/0238131 A1* | 7/2023 | Bernstein | A61B 5/0022 |
| | | | 600/347 |
| 2023/0268071 A1* | 8/2023 | Bernstein | A61B 5/72 |
| | | | 600/347 |
| 2024/0008777 A1* | 1/2024 | Fuchs | A61B 5/1473 |
| 2024/0366120 A1* | 11/2024 | Baumann | A61B 5/14532 |
| 2024/0366125 A1* | 11/2024 | Alonso-Soski | A61B 5/14503 |
| 2025/0006363 A1* | 1/2025 | Bernstein | A61B 5/01 |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2617965 | 10/2011 |
| CA | 2766685 | 12/2011 |
| CN | 101163440 | 4/2008 |
| CN | 101268932 | 9/2008 |
| CN | 101296650 | 10/2008 |
| DE | 4401400 | 7/1995 |
| EP | 0098592 | 1/1984 |
| EP | 0127958 | 12/1984 |
| EP | 0319277 | 6/1989 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 0680727 | 11/1995 |
| EP | 0724859 | 8/1996 |
| EP | 0805574 | 11/1997 |
| EP | 0973289 | 1/2000 |
| EP | 0678308 | 5/2000 |
| EP | 1048264 | 11/2000 |
| EP | 1292218 | 3/2003 |
| EP | 1077634 | 7/2003 |
| EP | 1413245 | 4/2004 |
| EP | 1568309 | 8/2005 |
| EP | 1666091 | 6/2006 |
| EP | 1703697 | 9/2006 |
| EP | 1704893 | 9/2006 |
| EP | 1956371 | 8/2008 |
| EP | 2031534 | 3/2009 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 2 236 077 | 10/2010 |
| EP | 1725163 | 12/2010 |
| EP | 2260757 | 12/2010 |
| EP | 2201969 | 3/2011 |
| EP | 2407094 | 1/2012 |
| EP | 2153382 | 2/2012 |
| EP | 2284773 | 2/2012 |
| EP | 2433565 | 3/2012 |
| EP | 1789116 | 5/2013 |
| EP | 1075209 | 10/2014 |
| EP | 2713879 | 7/2017 |
| EP | 2393417 | 1/2019 |
| EP | 3 632 314 | 4/2020 |
| EP | 3632315 | 4/2020 |
| EP | 3730045 | 3/2022 |
| EP | 3766408 | 4/2022 |
| EP | 4070727 | 10/2022 |
| EP | 3 831 283 | 4/2023 |
| EP | 4111949 | 7/2023 |
| EP | 3300658 | 1/2024 |
| EP | 4238496 | 2/2024 |
| GB | 1399192 | 6/1975 |
| GB | 2409951 | 7/2005 |
| JP | 03-500940 | 2/1991 |
| JP | 07-10973 | 2/1995 |
| JP | 07-182462 | 7/1995 |
| JP | 07-311196 | 11/1995 |
| JP | 10-305016 | 11/1998 |
| JP | 11-225359 | 8/1999 |
| JP | 2003-144417 | 5/2003 |
| JP | 2003-520091 | 7/2003 |
| JP | 2004-103354 | 4/2004 |
| JP | 2005-122994 | 5/2005 |
| JP | 2006-021031 | 1/2006 |
| JP | 2006-280464 | 10/2006 |
| JP | 2007-152037 | 6/2007 |
| JP | 2008-62072 A | 3/2008 |
| JP | 2008-506468 | 3/2008 |
| JP | 2012-221588 | 11/2012 |
| JP | 2014-056762 | 3/2014 |
| JP | 5642611 | 12/2014 |
| JP | 2015-053232 | 3/2015 |
| KR | 10-2017-0068964 | 6/2017 |
| WO | WO-1995/028878 | 2/1995 |
| WO | WO-1996/025089 | 8/1996 |
| WO | WO-1996/035370 | 11/1996 |
| WO | WO-1997/033513 | 9/1997 |
| WO | WO-1998/004902 | 2/1998 |
| WO | WO-98/16975 | 4/1998 |
| WO | WO-1998/035053 | 8/1998 |
| WO | WO-1999/27849 | 6/1999 |
| WO | WO-1999/28736 | 6/1999 |
| WO | WO-99/58190 | 11/1999 |
| WO | WO-1999/056613 | 11/1999 |
| WO | WO-00/49942 | 8/2000 |
| WO | WO-2000/049940 | 8/2000 |
| WO | WO-2000/059370 | 10/2000 |
| WO | WO-2000/060350 | 10/2000 |
| WO | WO 00/78213 | 12/2000 |
| WO | WO-2000/074753 | 12/2000 |
| WO | WO-01/17875 | 3/2001 |
| WO | WO-01/52727 | 7/2001 |

(56) References Cited

FOREIGN PATENT DOCUMENTS

| WO | WO-2001/052935 | 7/2001 |
| WO | WO-01/58348 | 8/2001 |
| WO | WO-2001/054753 | 8/2001 |
| WO | WO-01/64105 | 9/2001 |
| WO | WO-02/15778 | 2/2002 |
| WO | WO-2002/016905 | 2/2002 |
| WO | WO-02/058537 | 8/2002 |
| WO | WO-03/032411 | 4/2003 |
| WO | WO-2003/057027 | 7/2003 |
| WO | WO-2003/076893 | 9/2003 |
| WO | WO-2003/082091 | 10/2003 |
| WO | WO 2004/006982 | 1/2004 |
| WO | WO-2004/015539 | 2/2004 |
| WO | WO-2004/047445 | 6/2004 |
| WO | WO-2004/090503 | 10/2004 |
| WO | WO 2004/095648 | 11/2004 |
| WO | WO-2004/098405 | 11/2004 |
| WO | WO-2004/098682 | 11/2004 |
| WO | WO-2005/011779 | 2/2005 |
| WO | WO-2005/018450 | 3/2005 |
| WO | WO-2005/026689 | 3/2005 |
| WO | WO-2005/041766 | 5/2005 |
| WO | WO-2005/045744 | 5/2005 |
| WO | WO-2005/046780 | 5/2005 |
| WO | WO-2005/051170 | 6/2005 |
| WO | WO-2005/057175 | 6/2005 |
| WO | WO-2005/065538 | 7/2005 |
| WO | WO-2005/065542 | 7/2005 |
| WO | WO-2005/121785 | 12/2005 |
| WO | WO-2005/123186 | 12/2005 |
| WO | WO-2006/017358 | 2/2006 |
| WO | WO-2006/020212 | 2/2006 |
| WO | WO-2006/024671 | 3/2006 |
| WO | WO-2006/026741 | 3/2006 |
| WO | WO-2006/032653 | 3/2006 |
| WO | WO-2006/040083 | 4/2006 |
| WO | WO-2006/064397 | 6/2006 |
| WO | WO-2006/072035 | 7/2006 |
| WO | WO-2006/086423 | 8/2006 |
| WO | WO-2006/094513 | 9/2006 |
| WO | WO-2006/124099 | 11/2006 |
| WO | WO 2007/002189 | 1/2007 |
| WO | WO-2007/007459 | 1/2007 |
| WO | WO-2007/019289 | 2/2007 |
| WO | WO-2007/065285 | 6/2007 |
| WO | WO-2007/092618 | 8/2007 |
| WO | WO-2007/097754 | 8/2007 |
| WO | WO-2007/149319 | 12/2007 |
| WO | WO-2008/001366 | 1/2008 |
| WO | WO-2008/048452 | 4/2008 |
| WO | WO-2008/052374 | 5/2008 |
| WO | WO-2008/062099 | 5/2008 |
| WO | WO-2008/086541 | 7/2008 |
| WO | WO-2008/105768 | 9/2008 |
| WO | WO-2008/114223 | 9/2008 |
| WO | WO-2008/115409 | 9/2008 |
| WO | WO-2008/129532 | 10/2008 |
| WO | WO-2008/144445 | 11/2008 |
| WO | WO-2008/153693 | 12/2008 |
| WO | WO-2008/155377 | 12/2008 |
| WO | WO-2008/157821 | 12/2008 |
| WO | WO-2009/035773 | 3/2009 |
| WO | WO-2009/066288 | 5/2009 |
| WO | WO-2010/062898 | 6/2010 |
| WO | WO-2010/077329 | 7/2010 |
| WO | WO-2010/091005 | 8/2010 |
| WO | WO-2011/000528 | 1/2011 |
| WO | WO-2011/002815 | 1/2011 |
| WO | WO-2011/011643 | 1/2011 |
| WO | WO-2011/022418 | 2/2011 |
| WO | WO-2011/025549 | 3/2011 |
| WO | WO-2011/026053 | 3/2011 |
| WO | WO-2011/041531 | 4/2011 |
| WO | WO 2011/077893 | 6/2011 |
| WO | WO-2011/104616 | 9/2011 |
| WO | WO 2011/119896 | 9/2011 |
| WO | WO-2013/090215 | 6/2013 |
| WO | WO-2016/120920 | 8/2016 |
| WO | WO 2016/183493 | 11/2016 |
| WO | WO-2019/005627 | 1/2019 |

OTHER PUBLICATIONS

U.S. Appl. No. 60/614,683, filed Sep. 30, 2004, Brister et al.

U.S. Appl. No. 10/705,719, filed Jul. 7, 2020, Jakowtiz.

U.S. Appl. No. 18/130,381 (US 2023/0238131 A1) filed Apr. 3, 2023 (Jul. 27, 2023).

U.S. Appl. No. 18/176,293 (US 2023/0268071A1) filed Feb. 28, 2023 (Aug. 24, 2023).

U.S. Appl. No. 16/700,799 (US 2020/0100676 A1) filed Dec. 2, 2019 (Apr. 2, 2020).

U.S. Appl. No. 18/130,381, filed Oct. 23, 2024 Notice of Allowance.

U.S. Appl. No. 18/130,381, filed Oct. 9, 2024 Request for Continued Examination (RCE).

U.S. Appl. No. 18/130,381, filed Jul. 10, 2024 Notice of Allowance.

U.S. Appl. No. 18/130,381, filed Jun. 7, 2024 Request for Continued Examination (RCE).

U.S. Appl. No. 18/130,381, filed Apr. 24, 2024 Notice of Allowance.

U.S. Appl. No. 18/130,381, filed Apr. 9, 2024 Request for Continued Examination (RCE).

U.S. Appl. No. 18/130,381, filed Feb. 23, 2024 Notice of Allowance.

U.S. Appl. No. 18/130,381, filed Feb. 6, 2024 Response to Non-Final Office Action.

U.S. Appl. No. 18/130,381, filed Sep. 6, 2023 Non-Final Office Action.

U.S. Appl. No. 18/130,381, filed May 17, 2023 Track One Request Granted.

U.S. Appl. No. 18/176,293, filed Nov. 7, 2024 Notice of Allowance.

U.S. Appl. No. 18/176,293, filed Oct. 28, 2024 Preliminary Amendment.

U.S. Appl. No. 18/176,293, filed Oct. 23, 2024 Request for Continued Examination (RCE).

U.S. Appl. No. 18/176,293, filed Jul. 25, 2024 Notice of Allowance.

U.S. Appl. No. 18/176,293, filed Jun. 7, 2024 Request for Continued Examination (RCE).

U.S. Appl. No. 18/176,293, filed Apr. 10, 2024 Notice of Allowance.

U.S. Appl. No. 18/176,293, filed Mar. 18, 2024 Request for Continued Examination (RCE).

U.S. Appl. No. 18/176,293, filed Dec. 19, 2023 Notice of Allowance.

U.S. Appl. No. 18/176,293, filed Dec. 5, 2023 Preliminary Amendment.

U.S. Appl. No. 18/176,293, filed Nov. 30, 2023 Request for Continued Examination (RCE).

U.S. Appl. No. 18/176,293, filed Oct. 6, 2023 Corrected Notice of Allowability.

U.S. Appl. No. 18/176,293, filed Sep. 20, 2023 Notice of Allowance.

U.S. Appl. No. 18/176,293, filed Sep. 7, 2023 Response to Non-Final Office Action.

U.S. Appl. No. 18/176,293, filed Aug. 14, 2023 Non-Final Office Action.

U.S. Appl. No. 18/176,293, filed Jun. 5, 2023 Track One Request Granted.

U.S. Appl. No. 16/700,799, filed Sep. 11, 2024 Notice of Allowance.

U.S. Appl. No. 16/700,799, filed Aug. 5, 2024 Request for Continued Examination (RCE).

U.S. Appl. No. 16/700,799, filed Jul. 11, 2024 Corrected Notice of Allowability.

U.S. Appl. No. 16/700,799, filed Jun. 24, 2024 Notice of Allowance.

U.S. Appl. No. 16/700,799, filed Mar. 15, 2024 Response to Non-Final Office Action.

U.S. Appl. No. 16/700,799, filed Nov. 21, 2023 Non-Final Office Action.

U.S. Appl. No. 16/700,799, filed Apr. 23, 2020 Preliminary Amendment.

(56) References Cited

OTHER PUBLICATIONS

"Abbott Receives CE Mark for Freestyle® Libre, A Revolutionary Glucose Monitoring System for People with Diabetes," 8 pages (2023).

"DexCom (DXCM) Q1 2018 Results—Earnings Call Transcript" retrieved from https://seekingalpha.com/article/4168949-dexcom-dxcm-g1-2018-results-earnings-call-transcript on May 2, 2018, 4 pages.

"FDA authorizes first fully interoperable continuous glucose monitoring system, streamlines review pathway for similar devices," FDA News Release, retrieved from https://www.fda.gov/news-events/press-announcements/fda-authorizes-first-fully-interoperable-continuous-glucose-monitoring-system-streamlines-review on Mar. 27, 2018, 3 pages.

"GESilicones—Master Grade" retrieved from https://web.archive.org/web/20031105083652/http://www.gesilicones.com:80/gesilicones/am1/en/grade/mastergrade_kit_one_part.jsp?masterGradeId-749 &categoryId=12&typeId=21, Sep. 22, 2003, 2 pages.

"Within Definition & Meaning" retrieved from "https://www.dictionary.com/browse/within" on Sep. 9, 2022, 5 pages.

"Z-Carbon LCD Connector" retrieved from https://web.archive.org/web/20041211190712/http://www.zaxisconnector.com:80/Z-Carbon-LCD-Elastomeric-Connectors.shtml, Oct. 30, 2004, 2 pages.

510(k) Summary of Safety and Effectiveness, Cleo™ 90 Infusion Set, Smiths Medical MD, Inc., 618 pages (2004).

59th Annual Meeting, EASD, Oct. 2023, 326 pages.

Abbott 2023 Annual Report, 86 pages (2023).

Abbott Press Release—"Abbott's FreeStyle Libre® is Named Best Medical Technology in Last 50 Years by the Galien Foundation", 2 pages (2022).

Abbott Press Release—"Abbott's FreeStyle® Libre 2 ICGM Cleared in U.S. for Adults and Children with Diabetes, Achieving Highest Level of Accuracy and Performance Standards", 3 pages (2020).

Abbott Press Release—"FreeStyle Libre Honored by Prix Galien", 4 pages (2019).

Abbott Press Release—"Real-World Data Show Abbott's FreeStyle Libre® Systems and GLP-1 Medicines Work Better Together for People with Type 2 Diabetes", 2 pages (2024).

Abbott Reports Fourth-Quarter and Full-Year 2023 Results; Issues 2024 Financial Outlook, News Release, (Jan. 24, 2024), 20 pages.

*Abbott v. Dexcom*, Jack Griffis Direct Examination, dated Mar. 15, 2024, 38 pages.

Abbott's Continuous Blood Glucose Monitor Approval Soon, 3 pages (2006).

Accu-Chek® Compact Plus, Blood Glucose Meter, Owner's Booklet, 2008, 100 pages.

Ahn, "Abbott's Euro Approved Wearable Glucose Monitor is Different than Anything on the Market", 6 pages (2014).

Ahson, et al., RFID Handbook, Applications, Technology, Security, and Privacy, Taylor & Francis Group, 6 pages (2008).

AIM Inc. WP-98/002R2, Radio Frequency Identification RFID, A basic primer, 17 pages (2001).

Annex C1 GS1 User Guide, Sibionics (2023), 26 pages.

Annex C2 GS1 Product Insert, Sibionics, 4 pages (2023).

Annex C3 GS1 Quick Start Guide, Sibionics, (Nov. 1, 2023), 3 pages.

Annex C4 GS1 App User Guide, GS1 Continuous Glucose Monitoring System App User Guide English, (2023), 49 pages.

Annex C6 Extract from Eudamed registry in relation to the Second Defendant, Manufacturer, CN-MF-000017945, Shenzhen Sisensing Co., Ltd. China, (2023) 7 pages.

Annex D1 Excerpts from First Defendant's website: Sibionics GS1 Continuous Glucose Monitoring (CGM) System, 5 pages (Mar. 20, 2024).

Annex F2 Original Application of the Patent, EP Patent Application No. EP21152231.3, filed (Jan. 19, 2021), 133 pages.

Annex F3 Announcement on website of the Defendants, Sibionics is temporarily discontinuing CGM offerings in select European countries (2024), 7 pages.

Annex F3 Earlier Application of the Patent, EP Patent Application No. EP17182379.2, filed (Jul. 20, 2017), 131 pages.

Annex F4 Earliest Application of the Patent, EP Patent Application No. EP12857506.5, filed (Dec. 30, 2013), 131 pages.

Annex F5 Oxford Dictionary—distal (2023), 2 pages.

Annex F6 Announcement on website of the Defendants temporary cease of sale GS1 Device, Sibionics is temporarily discontinuing CGM offerings in selected European Countries, (2024), 4 pages.

Annex F9, Court of appeal Brussels, *Novartis* v. *Eurocjenerics*, in German with English Translation, 23 pages, Sep. 2016.

Apple, The Wayback Machine—Introduction, Apple Rubber Products (1999).

Application Note AN048, Compact Reach Xtend™ Bluetooth®, 802.11b/g WLAN Chip Antenna, Antenna Part No. FR05-S1-N-0-102, Texas Instruments, 13 pages (2008).

Application Note, Nordic Semiconductor, nRF9E5 RF and antenna layout, nAN900-05, 13 pages (2006).

Armour, J. C., et al., "Application of Chronic Intravascular Blood Glucose Sensor in Dogs", Diabetes, vol. 39, 1990, pp. 1519-1526.

ATTD Program, 2nd International Conference on Advanced Technologies & Treatments for Diabetes, Athens, Greece, 4 pages (2009).

Australian Patent Application No. 2008265541, Examiner's Report mailed Sep. 8, 2014.

Australian Patent Application No. 2016201703, Examiner's Report mailed Mar. 22, 2017.

Australian Patent Application No. 2017254903, Examiner's Report mailed Dec. 11, 2018.

AVR2023-AT86RF231 PCB reference design for antenna diversity, ATMEL® AVR Z Link, Application Note, 15 pages (2008).

Ballard, "User Interface Design Guidelines for J2ME MIDP 2.0" 9 pages (2005).

Baltensperger, Feature Article, Vials. Caps, Septa & Various Products in Comparison, ILM, 3 pages (Apr. 9, 2020).

Battery Connector, 1.20MM Height, 1.60MM Pitch, Double Row, Product Specification, Molex, 9 pages (2006).

Beardsall, et al., The continuous glucose monitoring sensor in neonatal intensive care, Arch Dis Child Fetal Neonatal Ed, 90, pp. F307-F310 (2005).

Benkič, et al., "Using RSSI value for distance estimation in Wireless sensor networks based on ZigBee", 4 pages (2000).

Bennion, N., et al., "Alternate Site Glucose Testing: A Crossover Design", Diabetes Technology & Therapeutics, vol. 4, No. 1, 2002, pp. 25-33.

Best Practice for Software Asset Management, OGC ITIL Managing IT services, TSO, 7 pages (2003).

Best Practice for Software Asset Management, TSO, 2003, pp. 19, 20, 69.

Bisco® EC2265 Electrically Conductive Solid, Product Data Sheet, Rogers Corporation, 2 pages (Dec. 14, 2023).

Black & Hastings et al., Handbook of Biomaterial Properties, Springer US, 1st Edition 607 pages (1998).

Black, et al., Handbook of Biomaterial Properties, Springer, 5 pages (1998).

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Bluetooth Antenna Design, Application Note, National Semiconductor Corporation, 16 pages (2005).

Blum, "Freestyle Libre Glucose Monitoring System", Clin Diabetes, vol. 36, No. 2, pp. 203-204 (2018).

Breton, et al., Optimum Subcutaneous Glucose Sampling and Fourier Analysis of Continuous Glucose Monitors, Journal of Diabetes Science and Technology, vol. 2, Issue 3, pp. 495-500 (2008).

Brooks, S. L., et al., "Development of an On-Line Glucose Sensor for Fermentation Monitoring", Biosensors, vol. 3, 1987/88, pp. 45-56.

Callaway, Wireless Sensor Networks, Architectures and Protocols, Auerbach Publications, 4 pages (2003).

Cambridge Dictionary of American English for "periphery", Cambridge University Press, 5 pages (2000).

(56) References Cited

OTHER PUBLICATIONS

Cambridge Dictionary of American English, 3 pages (2000)—Recess.
Canadian Patent Application No. 2,765,712, Examiner's Report mailed Apr. 10, 2017.
Canadian Patent Application No. 2,765,712, Examiner's Report mailed Apr. 29, 2016.
Canadian Patent Application No. 2,765,712, Examiner's Report mailed Mar. 27, 2018.
Cass, A. E., et al., "Ferrocene-Medicated Enzyme Electrode for Amperometric Determination of Glucose", Analytical Chemistry, vol. 56, No. 4, 1984, 667-671.
Cather, CGM Frustrations Survey, Dexcom, dated Jun. 2020, 37 pages.
Korean Application No. 10-2017-0068964, filed on Jun. 2, 2017, 99 pages (with English translation).
Priority Document, U.S. Appl. No. 62/272,983, filed Dec. 30, 2015, 171 pages.
U.S. Appl. No. 61/238,672, filed Aug. 31, 2009, 138 pages.
U.S. Appl. No. 61/247,541, filed Sep. 30, 2009, 69 pages.
U.S. Appl. No. 61/297,265, filed Jan. 22, 2010, 54 pages.
U.S. Pat. No. 11,000,216, issued on May 11, 2021, 86 pages.
CES 2022 Innovation Award Product, Innovation Awards Honorees, FreeStyle Libre 3 System, 1 page (2022).
Chen et al., Defining the Period of Recovery of the Glucose Concentration after its Local Perturbation by the Implantation of a Miniature Sensor, Clin Chem Lab Med 2002; 40 (8):786-789.
Chen, et al., "A novel fault-tolerant sensor system for sensor drift compensation", Sensors and Actuators, A 147:623-632 (2008).
Chicago Innovation Awards—Abbott Laboratories, retrieved from: https://chicagoinnovation.com/winners/abbott-laboratories/, 5 pages (2018).
Chinese Patent Application No. 20100006480.2, Original Language & English Translation of Office Action mailed Dec. 11, 2013.
Chinese Patent Application No. 20100006480.2, Original Language & English Translation of Office Action mailed May 6, 2013.
Chinese Patent Application No. 201080027344.1, Notice of Allowance mailed Jan. 15, 2016.
Chinese Patent Application No. 2010800273441, Original Language & English Translation of Office Action mailed Feb. 6, 2015.
Chinese Patent Application No. 2010800273441, Original Language & English Translation of Office Action mailed Jun. 5, 2014.
Chinese Patent Application No. 2014105252013, Original Language & English Translation of Office Action mailed Dec. 4, 2015.
Chinese Patent Application No. 2014105252013, Original Language & English Translation of Office Action mailed Jun. 3, 2016.
Chinese Patent Application No. 201601448601, Original Language & English Translation of Office Action mailed Dec. 10, 2018.
Chinese Patent Application No. 201601448601, Original Language & English Translation of Office Action mailed Mar. 23, 2018.
Chinese Patent Application No. 201601448601, Original Language & English Translation of Office Action mailed May 23, 2019.
Chip Antenna Layout Considerations for 802.11 Applications, Jul. 4, 2007 https://web.archive.org/web/20070704100715/http://www.johansontechnology.com/technicalnotes/ant/ 5 pages, retrieved on Oct. 28, 2019.
Choosing the Right Hamilton Syringe for Your Application, 4 pages (1998).
Claremont et al., In vivo chemical sensors and biosensors in clinical medicine, pp. 356-376 (1987).
Cleo® 90 Infusion Set Training Guide, 1 page.
Clinical Trials Competitor and Ecosystem Players, Abbott, dated Jun. 25, 2020, 29 pages.
COHRlastic Silicone Rubber Products, Saint-Gobain Performance Plastics, 7 pages (2002).
Compression Connectors, 1.60mm Pitch Compression Connector, 1.20mm Working Height, Dual-row, 4 Circuits, Molex, 2 pages (2014).

Conductive—High Consistency Silicone Rubber (HCR), Type—Carbon filled. (C), Technical Data Sheet, Primasil Silicones Ltd., 1 page (Dec. 14, 2023).
Conductive Carbon Filled Silicone (ERC-225), retrieved from the internet: EMI Conductive Rubber, LLC (emiconductiverubberllc.com); EMI Conductive Rubber, LLC, 5 pages (Dec. 14, 2023).
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Cunningham et al., Winefordner Seried Editor, "Chemical Analysis: A Seried of Monographs on Analytical Chemistry and Its Applications—In Vivo Glucose Sensing" 50 pages (2010).
Cunningham, D.D. et al., "In Vivo Glucose Sensing", John Wiley & Sons, 2010, chapter 1, pp. 4-9; chapter 5, pp. 113-156.
Cunningham, et al., In Vivo Glucose Sensing, Wiley, 9 pages (2010).
Custom Medical-Grade Silicone Gasket, Manufacturer of Medical Silicone Potash Sealing Liners, Suconvey, 17 pages (Dec. 20, 2023) (with an English translation).
Custom Silicone Gasket in Medical Quality, Manufacturer of Medical Silicone Rubber Seal Rollers, Suconvey, 16 pages (Dec. 14, 2023) (with an English translation).
Das et al., "Review—Electrochemistry and Other Emerging Technologies for Continuous Glucose Monitoring Devices," ECS Sensors Plus, 1 031601, 19 pages (2022).
Declaration of Gary D. Fletcher, Ph.D., 133 pages (2023).
Declaration of Gary D. Fletcher, Ph.D., 141 pages (2023).
Declaration of John Mastrototaro, Ph.D. (2022).
Declaration of John Mastrototaro, Ph.D., 22 pages (2023).
Declaration of Karl R. Leinsing, MSME, PE, in Support of Abbott's Motion for Summary Judgment, executed on May 19, 2023, 81 pages.
Deposition of Gary Fletcher, Ph.D., dated Jun. 26, 2024, 54 pages in *Abbott Diabetes Care Inc.*, et al. v. *Dexcom, Inc.*, Case No. 03946-82752US01, In the United States District Court for the District of Delaware.
Dexcom (DXCM) Company Profile, 2017 /Q4 Earnings call transcript, 12 pages (2017).
Dexcom G5 Mobile, Continuous Glucose Monitoring System, Quick Start Guide, Dexcom, 36 pages (2020).
Dexcom G6, Continuous Glucose Monitoring System, User Guide, 7 pages (2020).
Dexcom G6, Start Here, Set up Guide, Dexcom, 20 pages (2022).
Dexcom G7, Overview Webpage, retrieved from: https://www.dexcom.com/g7-com-system, 20 pages (2024).
Dexcom G7, User Guide, Dexcom, 196 pages (2024).
Dexcom Leading the Way, Seven Plus Continuous Glucose Monitoring System, 12 pages (2010).
Dexcom Seven Plus User's Guide, 145 pages (2010).
DexcomG6, Continuous Glucose Monitoring System, User Guide, 22 pages (2020).
DexcomG6, Start Here, Set up, Dexcom G6 Continuous Glucose Monitoring (CGM) System (G6), 8 pages (2019).
DexcomG6, Using Your G6, 7 pages (2020).
DexCom™ STS™ Continuous Glucose Monitoring System User's Guide (2006).
Diabetes Close Up—Conferences—#2, Diabetes Technology, pp. 1-8 (2003).
Diabetes Product Review: Abbott FreeStyle Libre Flash Glucose Monitor, 6 pages (2017).
Diem, P., et al., "Clinical Performance of a Continuous Viscometric Affinity Sensor for Glucose", Diabetes Technology & Therapeutics, vol. 6, 2004, pp. 790-799.
Direct Examination of Neil Sheehan, filed May 31, 2024, ADC-1 (30 pages) & ADC-2 (30 pages).
Dougherty, Bi Monthly Commercial Insights Meeting, 69 pages, Dec. 17, 2019.
Dowla, F., Handbook of RF & Wireless Technologies, Elsevier, 44 pages (2004).
Drawing Sheets for U.S. Pat. No. 10,973,443 issued Apr. 13, 2021, 2 pages.

(56) References Cited

OTHER PUBLICATIONS

Dufresne et al., How reliable are trial dates relied on by the PTAB in the Fintiv analysis?, Perkins Coie, 1600 PTAB & Beyond, 4 pages (2021).

Elastosil® LR 3162 A, B Specification Sheet, Wacker Chemie GmbH, Version 3.00, 6 pages (2004) (with an English Translation).

Elastosil® RT 602, RTV-2 Silicone Encapsulant Specification Sheet, Wacker Chemie GmbH, Version 3.00, 2 pages (2004).

Elastosil® RTV-1 Silicone Rubber Specification Sheet, Wacker Chemie GmbH, 16 pages (2001).

Electrically Conductive Elastomers, Data Sheet Material (Material Specifications), Euro Technologies, 6 pages (Dec. 14, 2023).

Electrically Conductive Silicone Sheet, retrieved from the internet: *Electrically Conductive Silicone Sheet Silex UK*; Silex Ltd., 3 pages (Dec. 14, 2023).

El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, vol. 1, No. 2, 2007, pp. 181-192.

Email communication from Sophie Hood dated Jan. 24, 2023, 6 pages.

Email from Christopher Dougherty with slides re. Global Commercial Insights Meeting, Abbott, sent on Dec. 17, 2019 (69 pages).

England, Glucose Sensor Applicator, designconcepts, Dexcom (project #2554), 6 pages, Apr. 21, 2014.

Englert et al., "Skin and Adhesive Issues with Continuous Glucose Monitors: A Sticky Situation," J Diab Sci Tech, vol. 8 4 745-751 (2014).

Enlite, Serter User Guide, Medtronics, 26 pages (2012).

Erhard, G., Designing with Plastics, Hanser, 521 pages (2006).

European Patent Application No. 08771682.5, Examination Report mailed Oct. 18, 2016.

European Patent Application No. 08771682.5, Minutes of the Oral Proceedings mailed Oct. 18, 2016.

European Patent Application No. 10739031.2, Examination Report mailed Oct. 28, 2016.

European Patent Application No. 10739031.2, Extended European Search Report mailed May 7, 2013.

European Patent Application No. 10739031.2, Opposition filed Dec. 20, 2018.

European Patent Application No. 10812438.9, Examination Report mailed Oct. 26, 2015.

European Patent Application No. 10812438.9, Extended European Search Report mailed Oct. 12, 2013.

European Patent Application No. 13000105.0, Opposition filed Jan. 4, 2019.

European Patent Application No. 15184320.8, Examination Report mailed Apr. 18, 2017.

European Patent Application No. 15184320.8, Extended European Search Report mailed Feb. 23, 2016.

European Patent Application No. 17201183.5, Examination Report mailed May 17, 2019.

European Patent Application No. 18192278.2, Extended European Search Report mailed Mar. 13, 2019.

European Patent Application No. 18208224.8, Extended European Search Report mailed Oct. 11, 2019.

Evans et al., Clinical temperature acquisition using proximity telemetry, Scientific and Technical Record, J. Biomed. Eng., vol. 13, 83-86 (1991).

Ex Parte Reexamination Certificate for U.S. Pat. No. 10,959,654, certificate issued on Aug. 5, 2024, 2 pages.

Excerpts Diabetes Health Magazine, Continuous Glucose Monitoring Systems, Diabetes Health, 50-51 Dec. 2006-Jan. 2007.

Excerpts from Expert Report of Catharine M. Lawton—Ex. 36, Spruce Point Capital Management, Does Dexcom Really Have a Future If It Can't Match Abbott's Scale? 2 pages, Mar. 21, 2019.

U.S. Pat. No. 10,827,954, issued on Nov. 10, 2020, 7 pages.

U.S. Pat. No. 10,973,443, issued on Apr. 13, 2021, 22 pages.

Exhibit 338-9F—Final Invalidity Chart of U.S. Pat. No. 10,874,338, 37 pages, Feb. 9, 2023.

Exhibit X, Claim Chart, Application of U.S. Pat. No. 11,013,440 to Dexcom G6, 19 pages (2021).

Extended European Search Report dated Nov. 17, 2021 in Application No. EP 21168039.

Federal Register, vol. 86, No. 211, pp. 60827-60829 (2021).

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

File history of U.S. Appl. No. 17/019,110, filed Sep. 11, 2020 (Exhibit 1002—Part 1-13, 2126 pages in total).

File history of U.S. Appl. No. 17/221,154, filed Apr. 2, 2021 (Exhibit 1002—Part 1-8, 1093 pages in total).

File History of U.S. Appl. No. 13/071,497, filed Mar. 24, 2011, 132 pages.

File History of U.S. Appl. No. 13/071,497, filed Mar. 24, 2011, 162 pages.

File History of U.S. Pat. No. 10,292,632, issued May 21, 2019, 486 pages.

File History of U.S. Pat. No. 10,945,649, issued Mar. 16, 2021, 484 pages.

File History of U.S. Pat. No. 11,013,440, issued May 25, 2021, 486 pages.

File History of U.S. Pat. No. 11,510,625, issued on Nov. 29, 2022 [Part 1 (179 pages), Part 2 (178 pages), Part 3 (220 pages) & Part 4 (86 pages).

File history of U.S. Appl. No. 61/317,243, filed Mar. 24, 2010 (234 pages).

File history of U.S. Appl. No. 61/345,562, filed May 17, 2010 (Exhibit 1007—Part 1 & 2, 273 pages in total).

File history of U.S. Appl. No. 61/361,374, filed Jul. 2, 2010 (Exhibit 1008—Part 1 & 2, 185 pages in total).

File history of U.S. Appl. No. 61/411,262, filed Nov. 8, 2010 (245 pages).

U.S. Appl. No. 60/614,764, filed Sep. 30, 2004, 657 pages.

U.S. Appl. No. 13/071,461, filed Mar. 24, 2011 (202 pages).

U.S. Appl. No. 62/524,247, filed Jun. 23, 2017, 532 pages.

U.S. Appl. No. 61/155,889, filed Feb. 26, 2009, 55 pages.

Finkenzeller, K., RFID Handbook, Fundamentals and Applications in Contactless Smart Cards and Identification, Second Edition, Wiley, 114 pages (2003).

Freckmann et al., "Performance Evaluation of Three Continuous Glucose Monitoring Systems: Comparison of Six Sensors per Subject in Parallel," Journal of Diabetes Science and Technology, vol. 7, Issue 4, 842-853 (2013).

FreeStyle Libre 14 day, "Your FreeStyle Libre 14 day System", In-Service Guide, Abbott, 28 pages (2021).

FreeStyle Libre 2 HCP Pulse, Mar. 2021 Report, Abbott, dated Apr. 13, 2021, 14 pages.

FreeStyle Libre 2, Get Started, "Your guide to the FreeStyle Libre 2 system", Abbott, 15 pages (2023).

FreeStyle Libre 3, Continuous Glucose Monitoring System, User's Manual, Abbott, 248 pages (Part 1—124 pages and Part 2—124 pages) (2023).

FreeStyle Libre 3, Flash Glucose Monitoring System, Get Started with the FreeStyle Libre 3 System, Abbott, 11 pages (2023).

FreeStyle Libre FAQs, retrieved from https://www.freestyle abbott/uk-en/support/faq/question-answer.html?q=UKFaqquestion-SS#, 2 pages (2024).

FreeStyle Libre, "It Frees Your Patients from the Inconvenience of Routine Blood Glucose Testing", 4 pages (2016) (with an English translation).

FreeStyle Libre, "Why Punch When You Can Scan 1, 2?", 20 pages (2016) (with an English translation).

FreeStyle Libre, Flash Glucose Measuring System, Abbott, 11 pages (2016) (with an English abstract).

FreeStyle Libre, Flash Glucose Measuring System, Fact Sheet, Abbott, 3 pages (2016) (with an English abstract).

(56) References Cited

OTHER PUBLICATIONS

Freestyle Navigator Continuous Glucose Monitoring System User's Guide, Abbott, 2008, 196 pages.

FreeStyle Navigator Continuous Glucose Monitoring System, Dept of Health & Human Services, Food and Drug Administration, Mar. 12, 2008, 8 pages.

FreeStyle Navigator Continuous Glucose Monitoring System, Summary of Safety and Effectiveness Data in support of Pre-Market Approval (PMA) No. P050020, Abbott Diabetes Care, 27 pages (2008).

FreeStyle Navigator Continuous Glucose Monitoring System, User Guide, Abbott Diabetes Care Inc., 195 pages (2008).

FreeStyle Navigator Continuous Glucose Monitoring System, User's Guide, Abbott Diabetes Care Inc., 38 pages (2008).

Frenzel, Printed-Circuit-Board Antennas, Electronic Design, 4 pages (2005).

Fujipoly, New High Performance Silver Zebra® Connector, Fujipoly Data Sheet No. FPDS 01-34/Version 5, 7 pages (2007).

Fujipoly, New High Performance Silver Zebra® Connector, Fujipoly Data Sheet No. FPDS 01-34/Version 2, 7 pages (2002).

Fujipoly, New High Performance Silver Zebra® Connector, Fujipoly Data Sheet No. FPDS 01-34/Version 5, 7 pages (2006).

Fujipoly, Zebra® Elastomeric Connectors, Fujipoly America Corp-Zebra—Zebra Carbon, 3 pages (2003).

G7 Continuous Glucose Monitoring System, User's Guide, DexCom, 2024, 174 pages.

Galien Golden Jubilee Webpage—https://www.galienfoundation. org/galien-golden-jubilee, 3 pages (2022).

Gandrud et al., "Functionality of the MiniMed Continuous Glucose Monitoring System (CGMS) in Young Childen with Type 1 Diabetes," Abstracts of the 64th Scientific Sessions of the American Diabetes Association, vol. 50, Supplement 2 (2004).

Garg, S., et al., "Improvement in Glycemic Excursions with a Transcutaneous, Real-Time Continuous Glucose Sensor", Diabetes Care, vol. 29, No. 1, 2006, pp. 44-50.

Garibotto, et al., "An Innovative Application of Shape Memory Alloy Technology Yields a Novel Therapeutic Approach to Diabetes Management", Insulet Corporation, 1 page (2009).

Gender of connectors and fasteners, Wikipedia, 6 pages (2024).

German Health Report, Diabetes 2023, German Diabetes Society, 23 pages (2022) (with an English translation).

German Innovation Award—FreeStyle Libre 2—Measure Sugar without Piercing Using a Sensor and App, 1 page (2020).

Gerritsen, et al., "Performance of subcutaneously implanted glucose sensors for continuous monitoring", The Netherlands Journal of Medicine, 54:167-179 (1999).

Gonzales, et al., "The Progress of Glucose Monitoring—A Review of Invasive to Minimally and Non-Invasive Techniques, Devices and Sensors", Sensors, 19(4):800, 45 pages (2019).

Gonzalez et al., "Low-Cost Wireless Sensors", Designer Reference Manual, Freescale Semiconductor, 49 pages (2007).

Good Design Award—2017 Good Design Award, Abbott Japan Co., Ltd., Glucose Monitoring Systems, FreeStyle Libre, 9 pages (2017).

Gough, et al., "Perspectives in Diabetes, Development of the Implantable Glucose Sensor, What Are the Prospects and Why Is It Taking So Long?", Diabetes, vol. 44, pp. 1005-1009 (1995).

Guardian® Real-Time, Continuous Glucose Monitoring System, User Guide, Medtronic MiniMed, Inc., 184 pages (2006).

Guardian® RT, Continuous Glucose Monitoring System, REF MMT-7900, User Guide, Medtronic MiniMed, 128 pages (2005).

Güler et al., "Theory and Applications of Biotelemetry", Journal of Medical Systems, vol. 26, No. 2, pp. 159-178 (2002).

Hager, Why Double Elecrocoat and Powder Coat?, 5 pages (1999).

Hall, An Interview with Kevin Sayer, President and CEO of Dexcom, About The New Dexcom G6, College Diabetes Network, 6 pages (2021).

Hao, Y., "Topical Review; Wireless Body Sensor Networks for Health-Monitoring Applications", Physiological Measurement, vol. 29, No. 11, Nov. 1, 2008, pp. R27-R56.

Harris et al., "Common Causes of Glucose Oxidase Instability in In Vivo Biosensing: A Brief Review," J Diabetes Sci Technol, 7(4):1030-1038 (2013).

Heftman, Chip Antenna Reduces Cell-Phone Dimensions, Microwaves & RF, p. 182 (1999).

Heide, Silicone Rubber for Medical Device Applications, Medical Plastics and Biomaterials, Special Section, Medical Device & Diagnostic Industry, 7 pages (1999).

Heinemann et al., Benefits and Limitations of MARD as a Performance Parameter for Continuous Glucose Monitoring in the Interstitial Space, Journal of Diabetes Science and Technology, vol. 14 (1) 135-150 (2020).

Heller et al., "Electrochemical Glucose Sensors and Their Applications in Diabetes Management," Chemical Reviews, vol. 108, No. 7, 2482-2505 (2008).

Heller et al., Electrochemistry in Diabetes Management, Accounts of Chemical Research, vol. 43, No. 7, pp. 963-973 (2010).

Heller, Integrated Medical Feedback Systems for Drug Delivery, AIChE Journal, vol. 51, No. 4, pp. 1054-1066 (2005).

Henning, Commercially Available Continuous Glucose Monitoring Systems, Chapter 5, In Vivo Glucose Sensing, Wiley, 50 pages (2010).

Hermanides, et al., "Current Application of Continuous Glucose Monitoring in the Treatment of Diabetes", Diabetes Care, vol. 34, Supp. 2, pp. S197-S201 (2011).

Hoss, et al., "Continuous Glucose Monitoring in Subcutaneous Tissue Using Factory—Calibrated Sensors: A Pilot Study", Diabetes Technology & Therapeutics, 12(8):591-597 (2010).

Hoss, et al., "Continuous glucose monitoring in the tissue: Do we really need to calibrate in-vivo?," Diabetes Technology & Therapeutics, vol. 11, No. 2, 23 pages (2009).

Hoss, et al., "Feasibility of Factory Calibration for Subcutaneous Glucose Sensors in Subjects With Diabetes", Journal of Diabetes Science and Technology, 8(1):89-94 (2014).

Huang, et al., Antennas: From Theory to Practice, John Wiley & Sons Ltd., 5 pages (2008).

IEEE 100, The Authoritative Dictionary of IEEE Standards Terms, 7th Ed., 3 pages (2000).

Index of /sdg, The Wayback Machine, Apple Rubber Products Inc., 183 pages (1999).

Information Technology Digest, University of Michigan, Information Technology Division, 1996, vol. 5 (5), 32 pages.

Instructions for Use, G7 User Guide, Dexcom, 174 pages (2024).

Insulet OmniPod Insulin Management System 019 UST400 User Manual, 2011, 190 pages.

Interview with Dexcom CEO, Dexcom CEO Kevin Sayer Explains G6, Written By: Michelle Boise, 9 pages (2018).

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

James, et al., Handbook of Microstrip Antennas, vol. 2, Peter Peregrinus on behalf of the Institution of Electrical Engineers, 8 pages (1989).

Japanese Patent Application No. 2012-526736, Original Language & English Translation of Office Action mailed Apr. 15, 2014.

Japanese Patent Application No. 2012-526736, Original Language & English Translation of Office Action mailed Dec. 16, 2014.

Japanese Patent Application No. 2015-159805, Original Language & English Translation of Office Action mailed Aug. 9, 2016.

Johnson, P. C., "Peripheral Circulation", John Wiley & Sons, 1978, pp. 198.

Joint Declaration of Funderburk, et al. for U.S. Appl. No. 15/963,828, 11 pages (2020).

Joseph, et al., "Glucose Sensing in the Subcutaneous Tissue: Attempting to Correlate the Immune Response with Continuous Glucose Monitoring Accuracy", Diabetes Technology & Therapeutics, vol. 20, No. 5, pp. 321-324 (2018).

Jungheim, K., et al., "How Rapid Does Glucose Concentration Change in Daily Life of Patients with Type 1 Diabetes?", 2002, pp. 250.

(56) References Cited

OTHER PUBLICATIONS

Jungheim, K., et al., "Risky Delay of Hypoglycemia Detection by Glucose Monitoring at the Arm", Diabetes Care, vol. 24, No. 7, 2001, pp. 1303-1304.

Kalivas, et al., "Compensation for Drift and Interferences in Multicomponent Analysis", Laboratory for Chemometrics, Department of Chemistry, University of Washington, 38 pages (1982).

Kaplan, S. M., "Wiley Electrical and Electronics Engineering Dictionary", IEEE Press, 2004, pp. 141, 142, 548, 549.

Kass, Fintiv Fails: PTAB Uses 'Remarkably Inaccurate' Trial Dates, Law 360, Portfolio Media, Inc., 1 page (2021).

Kondepati, V., et al., "Recent Progress in Analytical Instrumentation for Glycemic Control in Diabetic and Critically Ill Patients", Analytical Bioanalytical Chemistry, vol. 388, 2007, pp. 545-563.

Kovatchev et al., Evaluating the Accuracy of Continuous Glucose-Monitoring Sensors, Diabetes Care, vol. 27, No. 8, pp. 1922-1928 (2004).

Kreith, F., The CRC Handbook of Mechanical Engineering, 3 pages (1998).

Krieth, Frank, et al., The CRC Handbook of Mechanical Engineer, Second Edition, CRC Press Inc., 2665 pages (2004).

Lau, et al., "Stress and Deflection Analysis of Partially Routed Panels for Depanelization", IEEE Transactions on Components, Hybrids, and Manufacturing Technology, vol. CHMT-10, No. 3, 411-419 (1987).

Lee, Y., Microchip AN678 RFID Coil Design, 21 pages (1998).

Letter from the Department of Health & Human Services, Food and Drug Administration to Abbott Diabetes Care, Inc. dated Mar. 12, 2008, regarding the Premarket Approval Application (PMA) for the FreeStyle Navigator Continuous Glucose Monitoring System, 7 pages.

Letter from the U.S. Food & Drug Administration to Dexcom, Inc. regarding the Dexcom G7 Continuous Glucose Monitoring (CGM) System, 510(k) Premarket Notification and 510(k) summary, 10 pages, Dec. 7, 2022.

Letter from U.S. Food & Drug Administration to Bob Shen, Dexcom, Inc. re. K231081, Dexcom G7 Continuous Glucose Monitoring (CGM) System, 8 pages, May 15, 2023.

Liang, et al., An implantable bi-directional wireless transmission system for transcutaneous biological signal recording, Institute of Physics Publishing, Physiological Measurement, 26, 83-97 (2005).

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain the Newest Short-Range Connectivity Technology", Smart Computing Learning Series, Wireless Computing, vol. 8, Issue 5, 2002, pp. 72-74.

Lovett, "What's Next for Dexcom? CEO, CTO Talk G6 for Inpatient Use, Expanding CGMs for Patients without Diabetes", 17 pages (2020).

Loy, et al., ISM-Band and Short Range Device Antennas, Application Report, SWRA046A, Texas Instruments, 38 pages (2005).

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Mark, et al., Second Edition, Encyclopedia of Polymer Science and Engineering, vol. 15, Parts 1-16 (1989).

Mcgarraugh, G., et al., "Glucose Measurements Using Blood Extracted from the Forearm and the Finger", TheraSense, Inc., 2001, 16 Pages.

Mcgarraugh, G., et al., "Physiological Influences on Off-Finger Glucose Testing", Diabetes Technology & Therapeutics, vol. 3, No. 3, 2001, pp. 367-376.

Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

MD&DI, Qmed, Insert Molding, 11 pages (1996).

MD+DI Qmed, Medical Device and Diagnostic Industry, Silicone Rubber for Medical Device Applications, 8 pages (1999).

MD+DI Qmed, Silicone Rubber for Medical Device Applications, 9 pages (1999).

Medical Design Excellence Awards®, "27 Winners Announced at the 19th Annual Medical Design Excellence Awards (MDEA) Award Ceremony", 4 pages (2017).

Medical Silicone Seal/Closing Rolls, Suconvey, 16 pages (Dec. 14, 2023) (with an English translation).

Medtronic Minimed_iProTM2 User Guide, 108 pages (2010).

Meltsner, et al., Observations on rotating needle insertions using a brachytherapy robot, Physics in Medicine and Biology, 52, pp. 6027-6037 (2007).

Merriam-Webster's Collegiate Dictionary, 10th Ed., 4 pages (1999)—Housing and recess.

Merriam-Webster's Collegiate Dictionary, 10th Ed., 4 pages (1999)—Release and retain.

Microsoft Applications for Windows Mobile 6 User Guide, 184 pages (2008).

Mika, H., et al., "Practical Implementations of Passive and Semi-passive NFC Enabled Sensors", First International Workshop on Near Field Communication, 2009, pp. 69-74.

Moussy et al., Performance of Subcutaneously Implanted Needle-Type Glucose Sensors Employing a Novel Trilayer Coating, Analytical Chemistry, vol. 65, No. 15, pp. 2072-2077 (1993).

Moussy, 32.2: Implantable Glucose Sensor: Progress and Problems, IEEE, pp. 270-273 (2002).

MRF24J40MA, Data Sheet, 2.4GHz IEEE Std. 802.15.4TM, RF Transceiver Module, Microchip Technology Inc., 30 pages (2008).

Murata Puts Antenna on a Chip, Electronic News, p. 44 (1999).

Nagpal, D.P., "Computer Fundamentals: Concepts, Systems and Applications," S. Chand, 2008, pp. 836, 838.

News Release—Abbott—"BinaxNOW, FreeStyle Libre 2 Win BIG Innovation Honors", 6 pages (2021).

News Release—Abbott Ireland—"Abbott's FreeStyle Libre Flash Glucose Monitoring System Wins the IMSTA Most Innovative Product Multi-National Award 2017", 2 pages (2017).

News Release—Business Intelligence Group—"55 Chosen as Winners in Annual Big Innovation Awards", 3 pages (2018).

News Release—Edison Awards—"Edison Awards Announces 2016 Gold, Silver, and Bronze Awards Winners", 9 pages (2016).

Nichols et al., "Biocompatible materials for Continuous Glucose Monitoring Devices," Chem Rev., 113(4) 2528-2549 (2013).

Non-Final Office Action for U.S. Appl. No. 14/884,622 dated Jun. 13, 2018, 7 pages.

Non-Final Office Action for U.S. Appl. No. 17/030,030 dated Dec. 17, 2020, 7 pages.

Not Just a Patch, Dexcom G7 Release: The Most Exciting New Features, "Dexcom G7: These are the Most Exciting Features", 14 pages (2024).

Notice of Allowance for U.S. Appl. No. 15/963,828 dated Mar. 3, 2021, 32 pages.

Olafsdottir, et al., "A Clinical Trial of the Accuracy and Treatment Experience of the Flash Glucose Monitor FreeStyle Libre in Adults with Type 1 Diabetes", Diabetes Technology & Therapeutics, vol. 19, No. 3, pp. 164-172 (2017).

Omnipod image, Exhibit 182, 2 pages, Sep. 22, 2022.

OmniPod Insulin Management System, UST400, User Guide, Insulet Corporation, 190 pages (2011).

Original Premarket Approval Application, FreeStyle Navigator Continuous Glucose Monitoring System, Section VII: Manufacturing Section Steven Label Sensor Sheet Validation Plan, vol. 28 of 31, TheraSense, Inc., 61 pages (2005).

Panteleon, et al., The Role of the Independent Variable to Glucose Sensor Calibration, Diabetes Technology & Therapeutics, vol. 5, No. 3, pp. 401-410 (2003).

Parker, McGraw-Hill Dictionary of Mechanical and Design Engineering for the word "boss," 4 pages (1984).

PCT Application No. PCT/US2010/002401, International Preliminary Report on Patentability and Written Opinion of the International Searching Authority mailed Mar. 15, 2012.

(56) References Cited

OTHER PUBLICATIONS

PCT Application No. PCT/US2010/002401, International Search Report and Written Opinion of the International Searching Authority mailed Nov. 12, 2010.

PCT Application No. PCT/US2010/022928, International Preliminary Report on Patentability and Written Opinion of the International Searching Authority mailed Aug. 18, 2011.

PCT Application No. PCT/US2010/022928, International Search Report and Written Opinion of the International Searching Authority mailed Mar. 21, 2010.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Poitout, et al., A glucose monitoring system for on line estimation in man of blood glucose concentration using a miniaturized glucose sensor implanted in the subcutaneous tissue and a wearable control unit, Diabetologia, vol. 36, pp. 658-663 (1993).

Premarket Approval Application Amendment, FreeStyle Navigator Continuous Glucose Monitoring System, vol. 2 of 39, Section III, Device Description, Abbott Diabetes Care, Inc., 89 pages (2006).

Press Release—"Abbott's FreeStyle Libre® 3 Receives U.S. FDA Clearance—Features World's Smallest, Thinnest and Most Accurate 14-Day Glucose Sensor", 3 pages (2022).

Press Release—"Abbott's FreeStyle® Libre 14 Day Flash Glucose Monitoring System Now Approved in U.S.", 2 pages (2018).

Princy et al., "Studies on Conductive Silicone Rubber Compounds," 1043-1050, 8 pages (1998).

Quinn, C. P., et al., "Kinetics of Glucose Delivery to Subcutaneous Tissue in Rats Measured with 0.3-mm Amperometric Microsensors", The American Physiological Society, 1995, E155-E161.

Reiterer et al., Significance and Reliability of MARD for the Accuracy of CGM Systems, Journal of Diabetes Science and Technology, 11(1):59-67 (2017).

Resource Center Library References/Bibliography, Available at: https://www.dexcom.com/sites/dexcom.com/files/professionals/CGM_Resource_Center_Reference-Bibliography_LBL_010629_Rev_02. pdf ("Dexcom CGM Resource Center Library") (Freestyle Navigator), Jun. 12, 2011.

Response to Non-Final Office Action for U.S. Appl. No. 15/963,828, filed Dec. 8, 2020, 17 pages.

Response to Restriction Requirement for U.S. Appl. No. 14/884,622, filed Apr. 5, 2018, 15 pages.

Rice et al., "Continuous Measurement of Glucose, Facts and Challenges," Anesthesiology, V. 116, No. 1, 199-204 (2012).

Rigo et al., "Cutaneous Reactions to Continuous Glucose Monitoring and Continuous Subcutaneous Insulin Infusion Devices in Type I Diabetes Mellitus," Journal of Diabetes Science and Technology, vol. 154i 786-791 (2021).

Rocchitta et al., "Enzyme Biosensors for Biomedical Applications: Strategies for Safeguarding Analytical Performances in Biological Fluids," Sensors 16, 780, 21 pages (2016).

Rodriguez, N., et al., "Flexible Communication and Control Protocol for Injectable Neuromuscular Interfaces", IEEE Transactions on Biomedical Circuits and Systems, IEEE, vol. 1, No. 1, 2007, pp. 19-27.

Roe, J. N., et al., "Bloodless Glucose Measurements", Critical Review in Therapeutic Drug Carrier Systems, vol. 15, Issue 3, 1998, pp. 199-241.

S&P Global Market Intelligence, "DexCom, Inc. NasdaqGS:DXCM, Company Conference Presentation," 17 pages (2021).

S&P Global Market Intelligence, "DexCom, Inc. NasdaqGS:DXCM, Company Conference Presentation," 10 pages (2020).

S&P Global Market Intelligence, "DexCom, Inc. NasdaqGS:DXCM, Company Conference Presentation," 11 pages (2019).

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salditt, P., "Trends in Medical Device Design and Manufacturing", SMTA News and Journal of Surface Mount Technology, vol. 17, 2004, pp. 19-24.

Salehi, C., et al., "A Telemetry-Instrumentation System for Long-Term Implantable Glucose and Oxygen Sensors", Analytical Letters, vol. 29, No. 13, 1996, pp. 2289-2308.

Sales Drawing for Battery 1.2H 1.6MM Pitch Double Row Connector, Molex, 2 pages (2013).

Sayer, CGMS Changing Diabetes Management: Kevin Sayer, DIC Interview Transcript, Featuring Steve Freed, 11 pages (2019).

Scheduling Order, C.A. No. 23-239 (KAJ), filed on Sep. 19, 2023, 14 pages.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Schoepke, Chip Antenna Layout Considerations for 802.11 Applications, Johanson Technology, 7 pages (2006).

Sclater, et al., Mechanisms and Mechanical Devices Sourcebook, Fourth Edition, McGraw-Hill, 29 pages (2007).

Seagrove Partners, Globeview™, International Diabetes Device 2022 Blue Book, 143 pages.

Seal Design Guide, Apple Rubber Products Inc., 190 pages (1999).

Seal Design Guide, Apple Rubber, 122 pages (2020).

Sen-Serter® User Guide, Medtronic MiniMed, 96 pages (2006).

Seven®Plus Continuous Glucose Monitoring System, User's Guide, DexCom 2008, 144 pages.

Sharawl, Use of low-cost patch antennas in modern wireless technology, IEEE, 5 pages (2006).

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shenoi, Introduction to Digital Signal Processing and Filter Design, Wiley, 46 pages (2006).

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Silastic® 94-595, Liquid Silicone Rubber, Specification Sheet, Dow Corning Corp, 4 pages (2002).

Silastic® MDX4-4210 BioMedical Grade Elastomer, Product Information, Dow Corning, Ref. No. 51-0202K-01, 4 pages (2005).

Silicone Rubber for Medical Device Applications, Medical Device and Diagnostic Industry Qmed, Nov. 1, 1999 Column.

(56)                References Cited

OTHER PUBLICATIONS

SlimStack™ SMT Stacking, Board-to-Board Connectors, 0.40 to 1.00mm (.016 to .039") Pitch, 0.95 to 20.00mm (.037 to .787") Height, Product Catalogue, Molex, 8 pages (2004).
Slomski, et al., U.S. Appl. No. 61/037,246, filed Mar. 17, 2008, 13 pages.
Smith, The Scientist and Engineer's Guide to Digital Signal Processing, Second Edition, 46 pages (1999).
Sonix, Dexcom CEO—Prime Position in Our Market—Mad Money—CNBC.mp4, 4 pages (2023).
Sorrells, P., Microchip AN680 Passive RFID Basics, 7 pages (1998).
Standard Test Method for Rubber Property-Durometer Hardness, ASTM International, Designation: D 2240-05, 13 pages (2005).
Statement of Defense (Counterclaim) dated Sep. 1, 2023, Case No. 21 O 6562/23, filed in Munich District Court I, 67 pages.
Sterling® C carbon black, Product Data Sheet, Cabot Corporation, 2 pages (Dec. 14, 2023).
Sternberg, R., et al., "Study and Development of Multilayer Needle-Type Enzyme-Based Glucose Microsensors", Biosensors, vol. 4, 1988, pp. 27-40.
Stone et al., "User Interface Design and Evaluation," The Open University, 13 pages (2005).
Stone, et al., "User Interface Design and Evaluation", The Open University, 2005, pp. 92, 93, 172-174, 224, 273, 614.
Stone, et al., User Interface Design and Evaluation, 4 pages (2005).
STS® Seven Glucose Monitoring System User's Guide, 74 pages (2007).
Summary of Safety and Effectiveness Data, Continuous Glucose Monitor, FreeStyle Navigator® Continuous Glucose Monitoring System, 2008, 27 pages.
Tegnestedt, et al., "Levels and sources of sound in the intensive care unit—an observational study of three room types", *Acta Anaesthesiologica Scandinavica*, pp. 1-10 (2013).
The Chambers Dictionary, 4 pages (1998)—Retract.
The Edison Awards—About US, Recognizing Global Innovation Excellence, 3 pages (2024).
The Edison Awards—Edison Best New Product Awards, 2022 Winners, 52 pages (2022).
The Edison Awards—Edison Best New Product Awards™, 2021 Winners, 19 pages (2024).
The MiniMed Paradigm® REAL-Time Insulin Pump and Continuous Glucose Monitoring System, Insulin Pump User Guide, Paradigm® 522 and 722 Insulin Pumps, Medtronic MiniMed, Inc., 25 pages (2008).
The New Oxford American Dictionary, 3 pages (2001)—Retract.
The New Penguin English Dictionary, Penguin Books, 4 pages (2000)—Recess.
The only CGM approved for kids ages 2 years and up, Children with Diabetes—Report from Diabetes Technology Meeting, 3 pages (2003).
The Wayback Machine, https://web.archive.org/web/20061018055737/http:///www.accu-check.com/us/rewrite/content/en_US/2.1.7.1.:10/article/ACCM_general_article_3303.htm (ACCU-CHEK Softclix Plus Lancet Device) 2006, 2 pages.
The Wayback Machine, https://web.archive.org/web/20090316065810/http://www.accu-chek.com:80/us/rewrite/content/en_us/2.1.9:0/article/ACCM_general_article_5136.htm, (Compact Plus Blood Glucose Meter) 2009, 3 pages.
TheraSense Files Premarket Approval Application for Freestyle Navigator(TM) Cont, 3 pages (2003).
Therasense Navigates Continuous Glucose Monitor PMA, Prepares for Flash, The Gray Sheet, vol. 29, No. 37, 2 pages (2003).
Thévenot et al., "Electrochemical Biosensors: Recommended Definitions and Classification (Technical Report)", Pure Appl. Chem. 71(12):2333-2348 (1999).
Thompson, M., et al., "In Vivo Probes: Problems and Perspectives", Clinical Biochemistry, vol. 19, 1986, pp. 255-261.
Tsumura, et al., Histological Evaluation of Tissue Damage Caused by Rotational Needle Insertion, IEEE, pp. 5120-5123 (2016).

Tung, S., "Layers of Security for Active RFID Tags", RFID Handbook: Applications, Technology, Security, and Privacy, Edited by Ehson, et al., Chapter 33, 2008, pp. 1-28.
Turner, A., et al., "Diabetes Mellitus: Biosensors for Research and Management", Biosensors, vol. 1, 1985, pp. 85-115.
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Software Change to an Existing Device, Guidance for Industry and Food and Drug Administration Staff," 32 pages (2017).
U.S. Food & Drug Administration, Dexcom G7 Continuous Glucose Monitoring (GGM) System, K231081, May 15, 2023, 8 pages.
U.S. Food & Drug Administration, Premarket Approval (PMA) for Freestyle Navigator Continuous Glucose Monitor, 6 pages, Notice Date: Apr. 1, 2008.
U.S. Appl. No. 12/698,124, Office Action mailed Aug. 13, 2012.
U.S. Appl. No. 12/698,124, Office Action mailed Dec. 4, 2013.
U.S. Appl. No. 12/698,124, Office Action mailed Jun. 6, 2013.
U.S. Appl. No. 12/698,124, Office Action mailed Mar. 20, 2015.
U.S. Appl. No. 12/698,124, Office Action mailed Nov. 21, 2012.
U.S. Appl. No. 12/807,278, Advisory Action mailed Jul. 28, 2014.
U.S. Appl. No. 12/807,278, Advisory Action mailed Jun. 13, 2013.
U.S. Appl. No. 12/807,278, Advisory Action mailed Oct. 8, 2014.
U.S. Appl. No. 12/807,278, Advisory Action Mar. 7, 2016.
U.S. Appl. No. 12/807,278, Notice of Allowance mailed Jul. 5, 2018.
U.S. Appl. No. 12/807,278, Office Action mailed Apr. 3, 2017.
U.S. Appl. No. 12/807,278, Office Action mailed Aug. 21, 2012.
U.S. Appl. No. 12/807,278, Office Action mailed Feb. 1, 2018.
U.S. Appl. No. 12/807,278, Office Action mailed Jul. 5, 2016.
U.S. Appl. No. 12/807,278, Office Action mailed Mar. 29, 2013.
U.S. Appl. No. 12/807,278, Office Action mailed Mar. 5, 2015.
U.S. Appl. No. 12/807,278, Office Action mailed May 9, 2014.
U.S. Appl. No. 12/807,278, Office Action mailed Oct. 7, 2013.
U.S. Appl. No. 12/807,278, Office Action mailed Oct. 7, 2015.
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
U.S. Appl. No. 14/094,719, Office Action mailed Dec. 26, 2018.
U.S. Appl. No. 14/094,719, Office Action mailed Jul. 10, 2019.
U.S. Appl. No. 14/741,458, Advisory Action mailed Oct. 9, 2018.
U.S. Appl. No. 14/741,458, Office Action mailed Feb. 12, 2020.
U.S. Appl. No. 14/741,458, Office Action mailed Nov. 24, 2017.
U.S. Appl. No. 14/741,459, Advisory Action mailed Apr. 13, 2018.
U.S. Appl. No. 14/741,459, Office Action mailed Aug. 2, 2019.
U.S. Appl. No. 14/741,459, Office Action mailed Dec. 14, 2017.
U.S. Appl. No. 14/741,459, Office Action mailed Jan. 7, 2020.
U.S. Appl. No. 14/741,459, Office Action mailed Jun. 5, 2017.
U.S. Appl. No. 14/841,122, Office Action mailed Aug. 25, 2016.
U.S. Appl. No. 14/841,122, Office Action mailed Feb. 8, 2018.
U.S. Appl. No. 14/841,122, Office Action mailed Jan. 5, 2016.
U.S. Appl. No. 14/841,122, Office Action mailed Mar. 7, 2017.
U.S. Appl. No. 14/841,122, Office Action mailed May 1, 2019.
U.S. Appl. No. 14/841,122, Office Action mailed Sep. 18, 2018.
U.S. Appl. No. 14/841,224, Advisory Action mailed Jan. 28, 2019.
U.S. Appl. No. 14/841,224, Advisory Action mailed Jun. 2, 2017.
U.S. Appl. No. 14/841,224, Notice of Allowance mailed Jul. 25, 2019.
U.S. Appl. No. 14/841,224, Office Action mailed Apr. 17, 2018.
U.S. Appl. No. 14/841,224, Office Action mailed Feb. 19, 2019.
U.S. Appl. No. 14/841,224, Office Action mailed Feb. 8, 2018.
U.S. Appl. No. 14/841,224, Office Action mailed Jan. 14, 2016.
U.S. Appl. No. 14/841,224, Office Action mailed Jan. 17, 2017.
U.S. Appl. No. 14/841,224, Office Action mailed Jul. 31, 2017.
U.S. Appl. No. 14/841,224, Office Action mailed Nov. 3, 2016.
U.S. Appl. No. 14/841,224, Office Action mailed Sep. 26, 2018.
U.S. Appl. No. 14/841,429, Advisory Action mailed May 2, 2018.
U.S. Appl. No. 14/841,429, Office Action mailed Feb. 8, 2017.
U.S. Appl. No. 14/841,429, Office Action mailed Feb. 8, 2018.
U.S. Appl. No. 14/841,429, Office Action mailed Jan. 21, 2016.
U.S. Appl. No. 14/841,429, Office Action mailed Jun. 12, 2019.
U.S. Appl. No. 14/841,429, Office Action mailed May 20, 2016.

(56) References Cited

OTHER PUBLICATIONS

U.S. Appl. No. 14/841,429, Office Action mailed Oct. 27, 2016.
U.S. Appl. No. 14/841,429, Office Action mailed Sep. 21, 2018.
U.S. Appl. No. 15/985,615, Office Action mailed Jul. 27, 2018.
U.S. Appl. No. 15/985,615, Office Action mailed Mar. 7, 2019.
United States Securities and Exchange Commission, Form 10-K, 59 pages (2005).
United States Securities and Exchange Commission, Form S-1, 309 pages (2005).
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
van den Boom, et al., "Changes in the utilization of blood glucose test strips among patients using intermittent—scanning continuous glucose monitoring in Germany", Diabetes Obes Metab., 22:922-928 (2020).
Velho, G., et al., "Strategies for Calibrating a Subcutaneous Glucose Sensor", Biomedica Biochimica Acta, vol. 48, 1989, pp. 957-964.
Vulcan® XC72 carbon black, Product Data Sheet, Cabot Corporation, 2 pages (Dec. 14, 2023).
Walt et al., "The chemistry of enzyme and protein immobilization with glutaraldehyde," Trends in Analytical Chemistry, 13, 10, 425-430 (1994).
Wampler, et al., Carbon Black, Chapter 6 in Rubber Compounding, Chemistry and Applications, 48 pages (2004).
Ward et al., Rise in background current over time in a subcutaneous glucose sensor in the rabbit: relevance to calibration and accuracy, Biosensors & Bioelectronics, 15, pp. 53-61 (2000).
Ward, et al., A Wire-Based Dual-Analyte Sensor for Glucose and Lactane: In Vitro and in Vivo Evaluation, Military Metabolic Monitoring, edited by Friedl, C.K.E., Diabetes Technology & Therapeutics, vol. 6, No. 3, pp. 389-401 (2004).
Waterhouse, Printed Antennas for Wireless Communications, John Wiley & Sons, Ltd., 14 pages (2007).
Watkin, "An Introduction to Flash Glucose Monitoring," 16 pages (2013).
Webster's New College Dictionary, 2 pages (2001)—Alcove.
Webster's Third New International Dictionary, 5 pages (1993)—Retract.
Wikipedia, The Free Encyclopedia, "Continuous glucose monitor", retrieved from https://en.wikipedia.org/w/index.php?title=Continuous_glucose_monitor&oldid=1224795137, 12 pages (2024).
Wilson et al., Chapter 1, Introduction to the Glucose Sensing Problem, In Vivo Glucose Sensing, edited by D.D. Cunningham et al., pp. 1-27 (2010).
Wilson, G. S., et al., "Progress Toward the Development of an Implantable Sensor for Glucose", Clinical Chemistry, vol. 38, No. 9, 1992, pp. 1613-1617.
Wong, Planar Antennas for Wireless Communications, John Wiley & Sons, Inc., 16 pages (2003).
Xu et al., "Anti-Biofouling Strategies for Long-Term Continuous Use of Implantable Biosensors," Chemosensors, 8, 66, 30 pages (2020).
Z-Carbon Connector, Z-Axis Connector Company, 2 pages (Jun. 7, 2004-May 6, 2007).
Zhang, "Investigations of potentially implantable glucose sensors", University of Kansas, 24 pages (1991).
Zisser, H.C., "The OmniPod Insulin Management System: the Latest Innovation in Insulin Pump Therapy", Diabetes Therapy, 2010, 1(1):10-24.
Z-Silver Connector, 2 pages (2004).
Authenticated U.S. Government Information, §1910.1030, 2003, pp. 260-273.
BBC News, Bluetooth rival unveiled by Nokia, Oct. 4, 2006, 2 pages.
Breton, et al., "Fully Integrated Artificial Pancreas in Type 1 Diabetes, Modular Closed-Loop Glucose Control Maintains Near Normoglycemia", Diabetes, 61:2230-2237 (2012).

Dexcom G5 Mobile, Continuous Glucose Monitoring System, User Guide, 265 pages (Part 1—100 pages, Part 2—100 pages and Part 3—65 pages) (2015).
Digias, et al., Reduced pain perception with Pen Mate™, an automatic needle insertion device for use with an insulin pen, Practical Diabetes International Mar./Apr. 1999, vol. 16, No. 2, pp. 39-41.
Earlier Application as filed for EP Application No. 17182379.2 filed on Dec. 11, 2012, 131 pages.
Earliest Application as filed for EP Application No. 12857506.5 filed on Dec. 11, 2012, 131 pages.
Exhibit ERP-14 to the Expert Report of Eugene Randal Prais, Aug. 13, 2024 including Using your ACCU-CHEK® Multiclix Lancet Device, Roche, 2005, 3 pages.
Exhibit ERP-15 to the Expert Report of Eugene Randal Prais, Aug. 13, 2024 including ACCU-CHEK® Softclix, Lancing Device, Roche, 2007, 3 pages.
Exhibit ERP-16 to the Expert Report of Eugene Randal Prais, Aug. 13, 2024 including Microlet® 2 Lancing Device, Bayer, 2008, 2 pages.
Exhibit ERP-17 to the Expert Report of Eugene Randal Prais, Aug. 13, 2024 including Paradigm® 512 and 712 Infusion Pumps, Models MMT-512, MMT-712, User Guide, Medtronic, 2005, 163 pages.
Exhibit ERP-18 to the Expert Report of Eugene Randal Prais, Aug. 13, 2024 including 510(k) Safety and Effectiveness Summary, VanishPoint® Syringe, 1998, 6 pages.
Exhibit ERP-19 to the Expert Report of Eugene Randal Prais, Aug. 13, 2024 including Schematic based on Thomas, 2 pages.
Exhibit ERP-3 to the Expert Report of Eugene Randal Prais, Aug. 13, 2024 including Medical devices—Quality management systems—Requirements for regulatory purposes (ISO 13485:2003), Jul. 2003, 70 pages.
Exhibit ERP-4 to the Expert Report of Eugene Randal Prais, Aug. 13, 2024 including International Standard, ISO 14971, Medical devices—Application of risk management to medical devices, 2007, 91 pages.
Exhibit ERP-5 to the Expert Report of Eugene Randal Prais, Aug. 13, 2024 including International Standard, IEC 62366, Medical devices—Application of usability engineering to medical devices, 2007, 215 pages.
Exhibit ERP-6 to the Expert Report of Eugene Randal Prais, Aug. 13, 2024 including Kaye et al., Guidance for Industry and FDA Premarket and Design Control Reviewers, Medical Device Use-Safety: Incorporating Human Factors Engineering into Risk Management, CDRH, Jul. 18, 2000, 34 pages.
Exhibit ERP-7 to the Expert Report of Eugene Randal Prais, Aug. 13, 2024 including American National Standard, Human factors engineering—Design of medical devices, AAMI, 2010 [Part 1 (116 pages), Part 2 (116 pages), Part 3 (116 pages), Part 4 (72 pages) & Part 5 (46 pages)].
Exhibit ERP-8 to the Expert Report of Eugene Randal Prais, Aug. 13, 2024 including in vitro diagnostic test systems—Requirements for blood-glucose monitoring systems for self-testing in managing diabetes mellitus (ISO 15197:2003), May 2003, 44 pages.
Exhibit ERP-9 to the Expert Report of Eugene Randal Prais, Aug. 13, 2024 including DexCom™ STS™ Continuous Glucose Monitoring System, User's Guide, 2006, 58 pages.
Expert Statement of Pantelis Georgiou, Aug. 9, 2024, 52 pages.
FreeStyle Libre 14 day Flash Glucose Monitoring System, Product Insert, Abbott Diabetes Care Inc., 5 pages (2023).
FreeStyle Navigator Continuous Glucose Monitoring System, User's Guide, Abbott Diabetes Care Inc., 197 pages (2008).
Guardian® Real-Time Continuous Glucose Monitoring System, User Guide, Medtronics, 2006, 181 pages.
Guardian® RT, Continuous Glucose Monitoring System, REF MMT-7900, User Guide, Medtronic MiniMed, 129 pages (2005).
Hirsch, Realistic Expectations and Practical Use of Continuous Glucose Monitoring for the Endocrinologist, J Clin Endocrinol Metab, Jul. 2009, 94(7), pp. 2232-2238.
Hughes, The Business of Self-Monitoring of Blood Glucose: A Market Profile, Journal of Diabetes Science and Technology, vol. 3, Issue 5, Sep. 2009, pp. 1220-1223.

(56)  References Cited

OTHER PUBLICATIONS

Moore, The Potential Use of Radio Frequency Identification Devices for Active Monitoring of Blood Glucose Levels, Journal of Diabetes Science and Technology, vol. 3, Issue 1, Jan. 2009, pp. 180-183.
One-press Serter, User Guide, Medtronic MiniMed, 29 pages (2015).
Original Application as filed for EP Application No. 21152231.3 filed on Dec. 11, 2012, 133 pages.
Oxford English Dictionary for "distal", Oxford University Press, 2 pages (2023).
Pace, U.S. Appl. No. 61/569,287, filed Dec. 11, 2011, 75 pages (Part 1—33 pages and Part 2—42 pages).
Seven® Plus Continuous Glucose Monitoring System, User's Guide, Dexcom, 2011, 144 pages.
Specification vol. 0, Specification of the Bluetooth System, Wireless Connections Made Easy, Master Table of Contents & Compliance Requirements, Covered Core Package version: 2.1 + EDR, Current Master TOC issued: Jul. 26, 2007 [Part 1 (711 pages) & Part 2 (709 pages)].
STS®-Seven, Continuous Glucose Monitoring System, User's Guide, DexCom, Inc., 75 pages (2007).
The Britannica Dictionary for "circumference", downloaded on Aug. 23, 2024, 1 page.

* cited by examiner

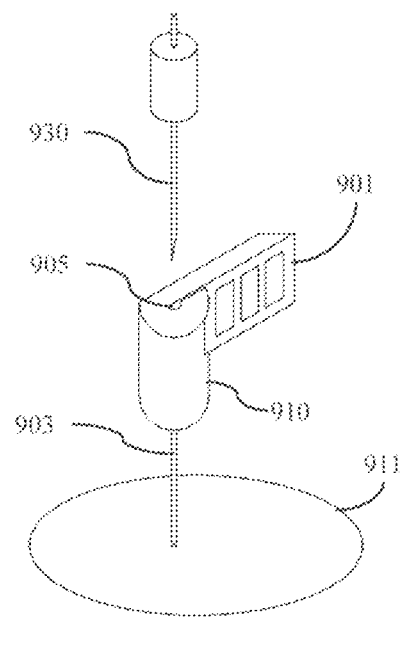
FIG. 9E
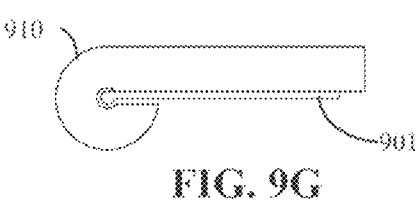
FIG. 9G
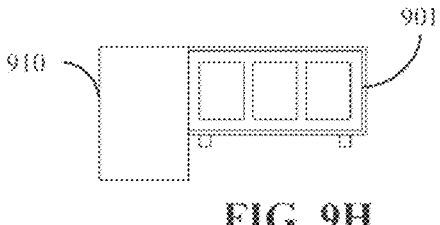
FIG. 9H
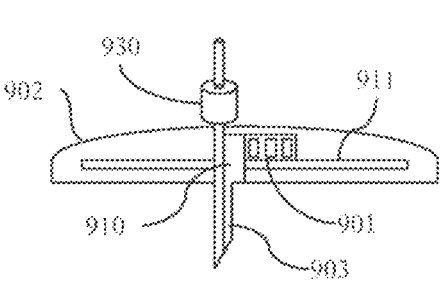
FIG. 9F
FIG. 9I
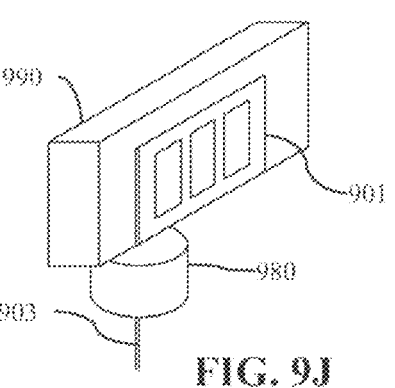
FIG. 9J

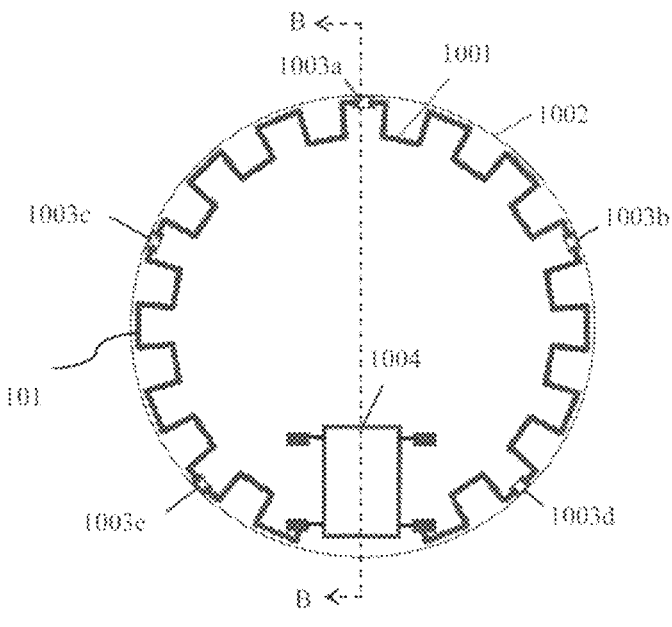
FIG. 10A
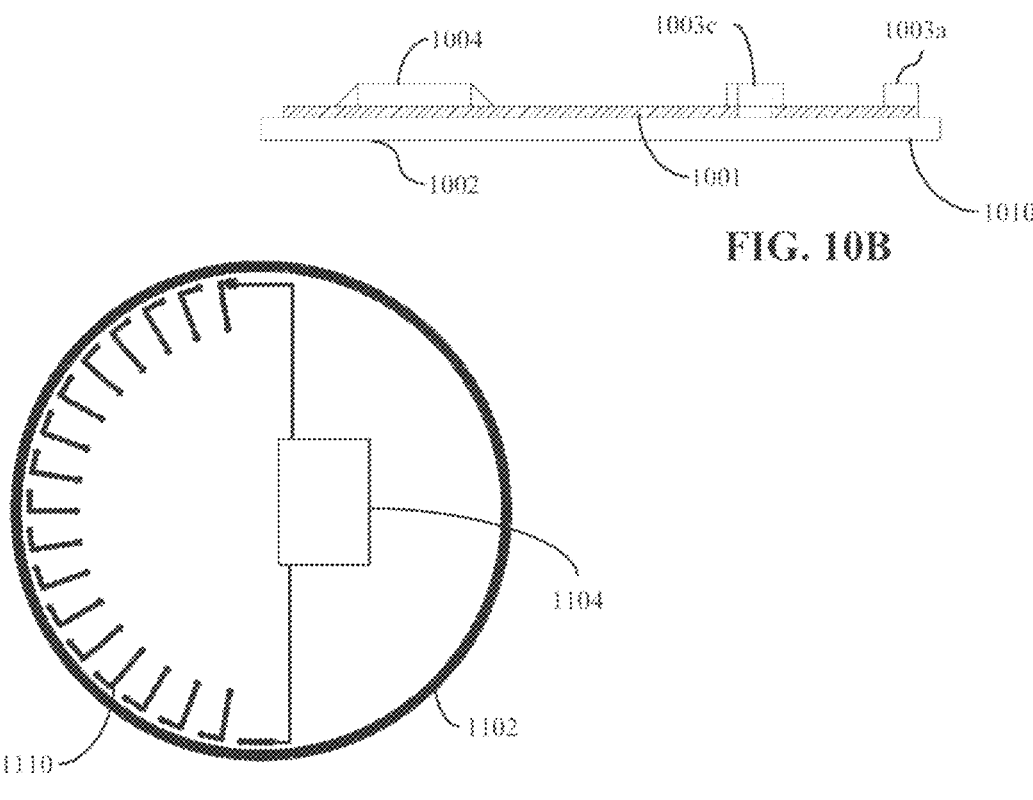
FIG. 10B
FIG. 11

MEDICAL DEVICES AND METHODS

RELATED APPLICATIONS

The present application is a continuation of U.S. patent application Ser. No. 18/130,381 filed Apr. 3, 2023, which is a continuation of U.S. patent application Ser. No. 18/176, 293 filed Feb. 28, 2023, which is a continuation of U.S. patent application Ser. No. 17/864,931 filed Jul. 14, 2022, which is a continuation of U.S. patent application Ser. No. 16/700,799 filed Dec. 2, 2019, which is a continuation of U.S. patent application Ser. No. 14/841,224 filed Aug. 31, 2015, now U.S. Pat. No. 10,492,685, which is a continuation of U.S. patent application Ser. No. 12/807,278 filed Aug. 31, 2010, now U.S. Pat. No. 10,136,816, which claims priority under § 35 U.S.C. 119 (c) to U.S. Provisional Application No. 61/238,581 filed Aug. 31, 2009, U.S. Provisional Application No. 61/247,519 filed Sep. 30, 2009, U.S. Provisional Application No. 61/247,514 filed Sep. 30, 2009, U.S. Provisional Application No. 61/247,508 filed Sep. 30, 2009, U.S. Provisional Application No. 61/256,925 filed Oct. 30, 2009, U.S. Provisional Application No. 61/291,326 filed Dec. 30, 2009, and U.S. Provisional Application No. 61/299, 924 filed Jan. 29, 2010, the disclosures of each of which are incorporated herein by reference for all purposes.

INCORPORATION BY REFERENCE

Patents, applications and/or publications described herein, including the following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365, now U.S. Pat. No. 7,811,231; 2005/0182306, now U.S. Pat. No. 8,771,183; 2006/0025662, now U.S. Pat. No. 7,740,581; 2006/0091006; 2007/0056858, now U.S. Pat. No. 8,298,389; 2007/0068807, now U.S. Pat. No. 7,846, 311; 2007/0095661; 2007/0108048, now U.S. Pat. No. 7,918,975; 2007/0199818, now U.S. Pat. No. 7,811,430; 2007/0227911, now U.S. Pat. No. 7,887,682; 2007/ 0233013; 2008/0066305, now U.S. Pat. No. 7,895,740; 2008/0081977, now U.S. Pat. No. 7,618,369; 2008/ 0102441, now U.S. Pat. No. 7,822,557; 2008/0148873, now U.S. Pat. No. 7,802,467; 2008/0161666; 2008/0267823; and 2009/0054748, now U.S. Pat. No. 7,885,698; U.S. patents application Ser. Nos. 11/461,725, now U.S. Pat. No. 7,866, 026; Ser. Nos. 12/131,012; 12/393,921, 12/242,823, now U.S. Pat. No. 8,219,173; Ser. No. 12/363,712, now U.S. Pat. No. 8,346,335; Ser. Nos. 12/495,709; 12/698,124; 12/698, 129, now U.S. Pat. No. 9,402,544; Ser. Nos. 12/714,439; 12/794,721, now U.S. Pat. No. 8,595,607; and Ser. No. 12/842,013, now U.S. Pat. No. 9,795,326, and U.S. Provisional Application Nos. 61/238,646, 61/246,825, 61/247, 516, 61/249,535, 61/317,243, 61/345,562, and 61/361,374.

BACKGROUND

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and with reduced pain, provide discreet monitoring to encourage frequent analyte monitoring to improve glycemic control.

SUMMARY

Embodiments of the subject disclosure include in vivo analyte monitoring devices, systems, kits, and processes of analyte monitoring and making analyte monitoring devices, systems and kits. Included are on-body (i.e., at least a portion of a device, system or a component thereof is maintained on the body of a user to monitor an analyte), physiological monitoring devices configured for real time measurement/monitoring of desired analyte level such as a glucose level over one or more predetermined time periods such as one or more predetermined monitoring time periods. Embodiments include transcutaneously positioned analyte sensors that are electrically coupled with electronics provided in a housing that is designed to be attached to the body of a user, for example, to a skin surface of a user, during the usage life of the analyte sensors or predetermined monitoring time periods. For example, an on body electronics assembly includes electronics that are operatively coupled to an analyte sensor and provided in a housing for placement on the body of a user.

Such device and system with analyte sensors provide continuous or periodic analyte level monitoring that is executed automatically, or semi-automatically by control logic or routines programmed or programmable in the monitoring devices or systems. As used herein, continuous, automatic, and/or periodic monitoring refer to the in vivo monitoring or detection of analyte levels with transcutaneously positioned analyte sensors.

In certain embodiments, the results of the in vivo monitored analyte level are automatically communicated from an electronics unit to another device or component of the system. That is, when the results are available, the results are automatically transmitted to a display device (or other user interaction device) of the system, for example, according to a fixed or dynamic data communication schedule executed by the system. In other embodiments, the results of the in vivo monitored analyte level are not automatically communicated, transferred or output to one or more device or component of the system. In such embodiments, the results are provided only in response to a query to the system. That is, the results are communicated to a component or a device of the system only in response to the query or request for such results. In certain embodiments, the results of the in vivo monitoring may be logged or stored in a memory of the system and only communicated or transferred to another device or component of the system after the one or more predetermined monitoring time periods.

Embodiments include software and/or hardware to transform any one of the devices, components or systems into any one of the other devices, components or systems, where such transformation may be user-configurable after manufacture. Transformation modules that include hardware and/or software to accomplish such transformation may be mateable to a given system to transform it.

Embodiments include electronics coupled to analyte sensors that provide functionalities to operate the analyte sensors for monitoring analyte levels over a predetermined monitoring time period such as for example, about 30 days (or more in certain embodiments), about 14 days, about 10 days, about 5 days, about 1 day, less than about 1 day. In certain embodiments, the usage life of each analyte sensor may be the same as or different from the predetermined monitoring time periods. Components of the electronics to provide the functionalities to operate the analyte sensors in certain embodiments include control logic or microprocessors coupled to a power supply such as a battery to drive the in vivo analyte sensors to perform electrochemical reactions to generate resulting signals that correspond to the monitored analyte levels.

Electronics may also include other components such as one or more data storage units or memory (volatile and/or nonvolatile), communication component(s) to communicate information corresponding to the in vivo monitored analyte level to a display device automatically when the information is available, or selectively in response to a request for the monitored analyte level information. Data communication between display devices and the electronics units coupled to the sensor may be implemented serially (e.g., data transfer between them are not performed at the same time), or in parallel. For example, the display device may be configured to transmit a signal or data packet to the electronics coupled to the sensor, and upon receipt of the transmitted signal or data packet, the electronics coupled to the sensor communicates back to the display device. In certain embodiments, a display device may be configured to provide RF power and data/signals continually, and detecting or receiving one or more return data packet or signal from electronics coupled to the sensor when it is within a predetermined RF power range from the display device. In certain embodiments, the display device and the electronics coupled to the sensor may be configured to transmit one or more data packets at the same time.

In certain embodiments, the one or more data storage units or memory stores data under the control of the electronics. In certain embodiments, the one or more data storage units or memory stores data according to a rolling data storage protocol executed by the control logic or microprocessors of the electronics. The data may be rolled according to time and/or prioritization, or otherwise. For example, a rolling data storage protocol may include a First-In/First-Out (FIFO) algorithm, First-In/Last-Out (FILO) algorithm, Last-In/First-Out (LIFO) algorithm, Last-In/Last-Out (LILO) algorithm. For example, embodiments include displacing the oldest stored data with most recent data in an iterative manner, or other rolling data protocol variations thereof.

Embodiments include self-powered in vivo analyte sensors that do not require a separate power supply to operate the analyte sensors for the detection or monitoring of the analyte level. In other words, self-powered sensors that provide their own power to operate and do not require any other power supply to monitor analyte in vivo are described.

Embodiments also include electronics programmed to store or log in the one or more data storage units or a memory data associated with the monitored analyte level over the sensor usage life or during a monitoring time period. During the monitoring time period, information corresponding to the monitored analyte level may be stored but not displayed or output during the sensor usage life, and the stored data may be later retrieved from memory at the end of the sensor usage life or after the expiration of the predetermined monitoring time period, e.g., for clinical analysis, therapy management, etc.

In certain embodiments, the predetermined monitoring time period may be the same as the sensor usage life time period such that when an analyte sensor usage life expires (thus no longer used for in vivo analyte level monitoring), the predetermined monitoring time period ends. In certain other embodiments, the predetermined monitoring time period may include multiple sensor usage life time periods such that when an analyte sensor usage life expires, the predetermined monitoring time period has not ended, and the expired analyte sensor is replaced with another analyte sensor during the same predetermined monitoring time period. The predetermined monitoring time period may include the replacement of multiple analyte sensors for use.

In certain embodiments, in addition to the monitored analyte level information, other information may be communicated to a device, system or a component thereof, such as, but not limited to, monitored temperature information, heart rate, one or more biomarkers such as HbA1C or the like, stored analyte level information spanning a time period, e.g., the past 1 second to about 48 hours, e.g., the past 1 minute to about 24 hours, e.g., the past about 1 minute to about 10 hours, e.g., the past about 8 hours, or the past about 2 hours, or the past about 1 hour, or the past about 30 minutes, or the past about 15 minutes.

In certain embodiments, temperature (in vivo and/or skin and/or ambient) information may be obtained and stored in memory, e.g., to be used in an algorithm to compensate for temperature dependent inaccuracies in monitored analyte levels.

Analyte level trend information may be generated or constructed based on stored analyte level information spanning a time period (e.g., corresponding to a temperature time period, or other) and communicated to the display device. The trend information may be output graphically and/or audibly and/or tactilely, and/or numerically and/or otherwise presented on a user interface of the display device to provide indication of the analyte level variation during this time period.

Embodiments include wirelessly communicating analyte level information from an on body electronics device to a second device such as a display device. Examples of communication protocols between on body electronics and the display device may include radio frequency identification (RFID) protocols or RF communication protocols. Exemplary RFID protocols include but are not limited to near field communication protocols that include short communication ranges (e.g., about 12 inches or less, or about 6 inches or less, or about 3 inches or less, or about 2 inches or less), high frequency wireless communication protocols, far field communication protocols (e.g., using ultra high frequency (UHF) communication systems) for providing signals or data from on body electronics to display devices.

Communication protocols may use 433 MHz frequency, 13.56 MHz frequency, 2.45 GHz frequency, or other suitable frequencies for wireless communication between the on body electronics that includes electronics coupled to an analyte sensor, and display devices and/or other devices such as a personal computer. While certain data transmission frequencies and/or data communication ranges are described above, within the scope of the present disclosure, other data suitable data transmission frequencies and/or data communication ranges may be used between the various devices in the analyte monitoring system.

Embodiments include data management systems including, for example, a data network and/or personal computer and/or a server terminal and/or one or more remote computers that are configured to receive collected or stored data from the display device for presenting analyte information and/or further processing in conjunction with the physiological monitoring for health management. For example, a display device may include one or more communication ports (hard wired or wireless) for connection to a data network or a computer terminal to transfer collected or stored analyte related data to another device and/or location. Analyte related data in certain embodiment are directly communicated from the electronics coupled to the analyte sensor to a personal computer, server terminal, and/or remote computers over the data network.

In certain embodiments, calibration "invisible" systems and methods are provided that determine clinically accurate analyte concentrations at least over the predetermined sensing period of analyte sensor systems without obtaining one or more independent analyte measurements (e.g., without using an in vitro test strip or other reference device) for calibration of generated analyte related signal from the analyte sensor during the usage life of the sensor, i.e., post-manufacture. In other words, once the analyte sensors are positioned in the body of the user, control logic or microprocessors in the electronics, or the microprocessors in the display device include one or more algorithms or programming to accurately convert or correlate signals related to the sensed analyte (e.g., in nA, counts, or other appropriate units) to a corresponding analyte level (e.g., converted to an analyte level in mg/dL or other appropriate units) without a reference value provided to the system, rendering sensor calibration "invisible" to the user such that the system does not require any human intervention for analyte sensor calibration.

These and other features, objects and advantages of the present disclosure will become apparent to those persons skilled in the art upon reading the details of the present disclosure as more fully described below.

BRIEF DESCRIPTION OF THE DRAWINGS

FIGS. 9A-9J illustrate on body electronics assembly including analyte sensor, components for connection to a PCB of on body electronics in certain embodiments;

FIG. 10A illustrates a top planar view of antenna and electronic circuit layout of the on body electronics of the analyte monitoring system 100 of FIG. 1 in certain embodiments;

FIG. 10B illustrates a cross sectional view of antenna and electronic circuit layout of the on body electronics of the analyte monitoring system 100 of FIG. 1 in certain embodiments;

FIG. 11 illustrates a top planar view of the antenna layout on the circuit board of the on body electronics in certain embodiments;

DETAILED DESCRIPTION

Figure 1:
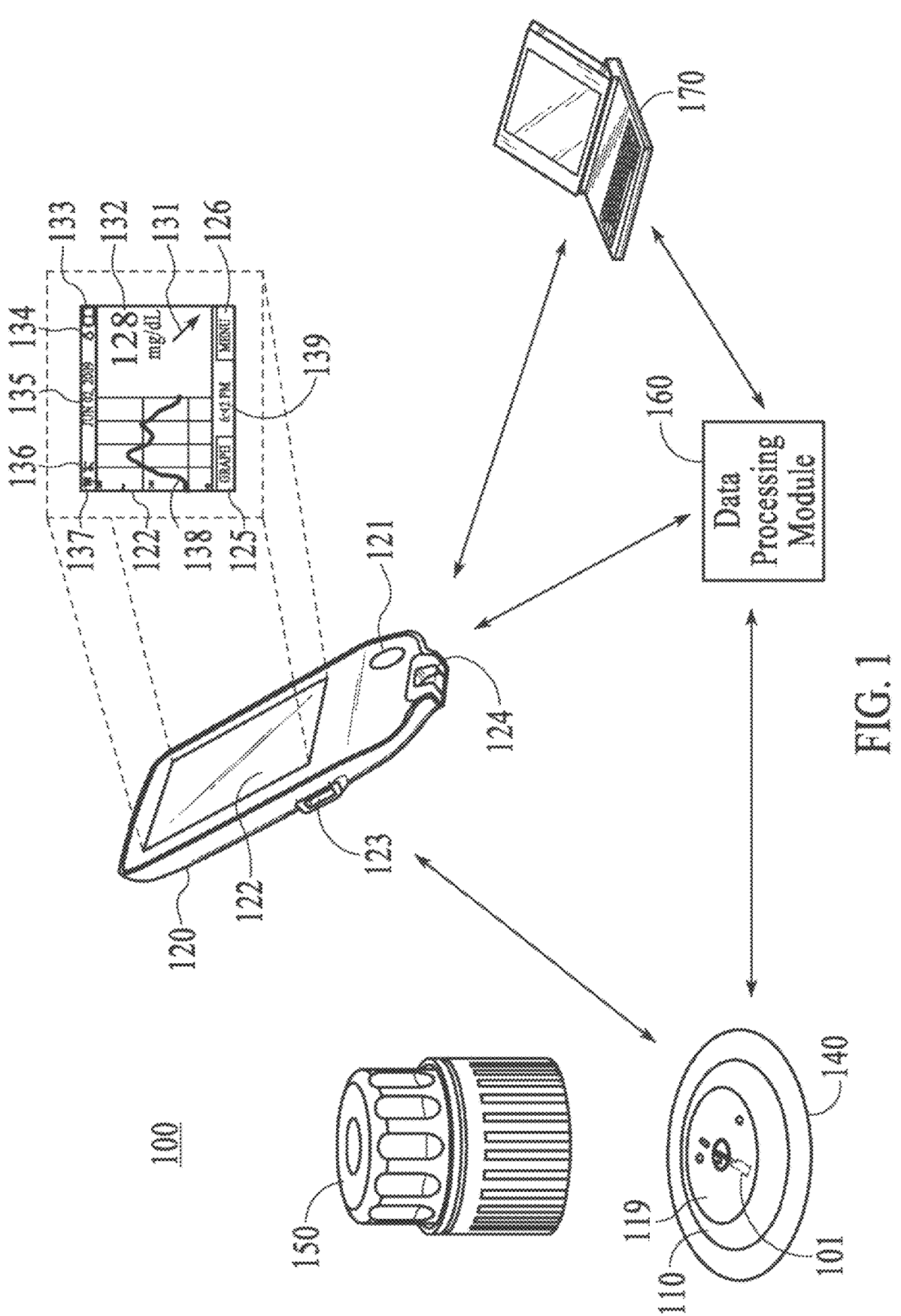
FIG. 1 illustrates analyte monitoring system for real time analyte (e.g., glucose) measurement, data acquisition and/or processing in certain embodiments.

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to in vivo methods and devices for detecting at least one analyte such as glucose in body fluid. Accordingly, embodiments include in vivo analyte sensors configured so that at least a portion of the sensor is positioned in the body of a user (e.g., within the ISF), to obtain information about at least one analyte of the body, e.g., transcutaneously positioned in user's body. In certain embodiments, an in vivo analyte sensor is coupled to an electronics unit that is maintained on the body of the user such as on a skin surface, where such coupling provides on body, in vivo analyte sensor electronics assemblies.

In certain embodiments, analyte information is communicated from a first device such as an on body electronics unit to a second device which may include user interface features, including a display, and/or the like. Information may be communicated from the first device to the second device automatically and/or continuously when the analyte information is available, or may not be communicated automatically and/or continuously, but rather stored or logged in a memory of the first device. Accordingly, in many embodiments of the system, analyte information derived by the sensor/on body electronics (for example, on body electronics assembly) is made available in a user-usable or viewable form only when queried by the user such that the timing of data communication is selected by the user.

In this manner, analyte information is only provided or evident to a user (provided at a user interface device) when desired by the user even though an in vivo analyte sensor automatically and/or continuously monitors the analyte level in vivo, i.e., the sensor automatically monitors analyte such as glucose on a pre-defined time interval over its usage life. For example, an analyte sensor may be positioned in vivo and coupled to on body electronics for a given sensing period, e.g., about 14 days. In certain embodiments, the sensor-derived analyte information is automatically communicated from the sensor electronics assembly to a remote monitor device or display device for output to a user throughout the 14 day period according to a schedule programmed at the on body electronics (e.g., about every 1 minute or about every 5 minutes or about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated and sensor-derived information is then sent from the on body electronics to the remote device or display device.

In still other embodiments, the information may be communicated from the first device to the second device automatically and/or continuously when the analyte information is available, and the second device stores or logs the received information without presenting or outputting the information to the user. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device.

Accordingly, in certain embodiments once a sensor electronics assembly is placed on the body so that at least a portion of the in vivo sensor is in contact with bodily fluid such as ISF and the sensor is electrically coupled to the electronics unit, sensor derived analyte information may be communicated from the on body electronics to a display device on-demand by powering on the display device (or it may be continually powered), and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body device and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including but not limited to one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include in vivo analyte sensors and on body electronics that together provide body wearable sensor electronics assemblies. In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on body electronics assemblies completely in an interior compartment, i.e., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collect information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc.). For example, a display device communication port may enable charging a display device battery with a respective charging cable and/or data exchange between a display device and its compatible informatics software.

Compatible informatics software in certain embodiments include, for example, but not limited to stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc.

Embodiments may include a haptic feedback feature such as a vibration motor or the like, configured so that corresponding notifications (e.g., a successful on-demand reading received at a display device), may be delivered in the form of haptic feedback.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

For example, analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times, with a single sensor or with a plurality of sensors which may use the same on body electronics (e.g., simultaneously) or with different on body electronics.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a body fluid such as ISF, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. patent Application Ser. No. 12/698,129 filed on Feb. 1, 2010, now U.S. Pat. No. 9,402,544 and U.S. Provisional Application Nos. 61/238,646, 61/246,825, 61/247,516, 61/249,535, 61/317,243, 61/345,562, and 61/361,374, the disclosures of each of which are incorporated herein by reference for all purposes.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or low power including no power, inactive mode, or all components may be in an inactive mode, powered down mode. Upon receipt of the command, the remaining portion (or all) of the components of the on body electronics is switched to active, fully operational mode.

Embodiments of on body electronics may include one or more printed circuit boards with electronics including control logic implemented in ASIC, microprocessors, memory, and the like, and transcutaneously positionable analyte sensors forming a single assembly. On body electronics may be configured to provide one or more signals or data packets associated with a monitored analyte level upon detection of a display device of the analyte monitoring system within a predetermined proximity for a period of time (for example, about 2 minutes, e.g., 1 minute or less, e.g., about 30 seconds or less, e.g., about 10 seconds or less, e.g., about 5 seconds or less, e.g., about 2 seconds or less) and/or until a confirmation, such as an audible and/or visual and/or tactile (e.g., vibratory) notification, is output on the display device indicating successful acquisition of the analyte related signal from the on body electronics. A distinguishing notification may also be output for unsuccessful acquisition in certain embodiments.

In certain embodiments, the monitored analyte level may be correlated and/or converted to glucose levels in blood or other fluids such as ISF. Such conversion may be accomplished with the on body electronics, but in many embodiments will be accomplished with display device electronics. In certain embodiments, glucose level is derived from the monitored analyte level in the ISF.

Analyte sensors may be insertable into a vein, artery, or other portion of the body containing analyte. In certain embodiments, analyte sensors may be positioned in contact with ISF to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Embodiments of In Vivo Analyte Monitoring Systems

FIG. 1 shows an exemplary in vivo-based analyte monitoring system 100 in accordance with embodiments of the present disclosure. As shown, in certain embodiments, analyte monitoring system 100 includes on body electronics 110 electrically coupled to in vivo analyte sensor 101 (a proximal portion of which is shown in FIG. 1) and attached to adhesive layer 140 for attachment on a skin surface on the body of a user. On body electronics 110 includes on body housing 119, that defines an interior compartment. Also shown in FIG. 1 is insertion device 150 that, when operated, transcutaneously positions a portion of analyte sensor 101 through a skin surface and in fluid contact with ISF, and positions on body electronics 110 and adhesive layer 140 on a skin surface. In certain embodiments, on body electronics 110, analyte sensor 101 and adhesive layer 140 are sealed within the housing of insertion device 150 before use, and in certain embodiments, adhesive layer 140 is also sealed within the housing or itself provides a terminal seal of the insertion device 150. Devices, systems and methods that may be used with embodiments herein are described, e.g., in U.S. patent application Ser. No. 12/698,129, now U.S. Pat. No. 9,402,544 and U.S. Provisional Application Nos. 61/238,646, 61/246,825, 61/247,516, 61/249,535, 61/317,243, 61/345,562, and 61/361,374, the disclosures of each of which are incorporated herein by reference for all purposes.

Referring back to the FIG. 1, analyte monitoring system 100 includes display device 120 which includes a display 122 to output information to the user, an input component 121 such as a button, actuator, a touch sensitive switch, a capacitive switch, pressure sensitive switch, jog wheel or the like, to input data or command to display device 120 or otherwise control the operation of display device 120. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 110 may be configured to store some or all of the monitored analyte related data received from analyte sensor 101 in a memory during the monitoring time period, and maintain it in memory until the usage period ends. In such embodiments, stored data is retrieved from on body electronics 110 at the conclusion of the monitoring time period, for example, after removing analyte sensor 101 from the user by detaching on body electronics 110 from the skin surface where it was positioned during the monitoring time period. In such data logging configurations, real time monitored analyte level is not communicated to display device 120 during the monitoring period or otherwise transmitted from on body electronics 110, but rather, retrieved from on body electronics 110 after the monitoring time period.

In certain embodiments, input component 121 of display device 120 may include a microphone and display device 120 may include software configured to analyze audio input received from the microphone, such that functions and operation of the display device 120 may be controlled by voice commands. In certain embodiments, an output component of display device 120 includes a speaker for outputting information as audible signals. Similar voice responsive components such as a speaker, microphone and software routines to generate, process and store voice driven signals may be provided to on body electronics 110.

In certain embodiments, display 122 and input component 121 may be integrated into a single component, for example a display that can detect the presence and location of a physical contact touch upon the display such as a touch screen user interface. In such embodiments, the user may control the operation of display device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 120 also includes data communication port 123 for wired data communication with external devices such as remote terminal (personal computer) 170, for example. Example embodiments of the data communication port 123 include USB port, mini USB port, RS-232 port, Ethernet port, Firewire port, or other similar data communication ports configured to connect to the compatible data cables. Display device 120 may also include an integrated in vitro glucose meter, including in vitro test strip port 124 to receive an in vitro glucose test strip for performing in vitro blood glucose measurements.

Referring still to FIG. 1, display 122 in certain embodiments is configured to display a variety of information-some or all of which may be displayed at the same or different time on display 122. In certain embodiments the displayed information is user-selectable so that a user can customize the information shown on a given display screen. Display 122 may include but is not limited to graphical display 138, for example, providing a graphical output of glucose values over a monitored time period (which may show important markers such as meals, exercise, sleep, heart rate, blood pressure, etc.), numerical display 132, for example, providing monitored glucose values (acquired or received in response to the request for the information), and trend or directional arrow display 131 that indicates a rate of analyte change and/or a rate of the rate of analyte change, e.g., by moving locations on display 122.

As further shown in FIG. 1, display 122 may also include date display 135 providing for example, date information for the user, time of day information display 139 providing time of day information to the user, battery level indicator display 133 which graphically shows the condition of the battery (rechargeable or disposable) of the display device 120, sensor calibration status icon display 134 for example, in monitoring systems that require periodic, routine or a predetermined number of user calibration events, notifying the user that the analyte sensor calibration is necessary, audio/vibratory settings icon display 136 for displaying the status of the audio/vibratory output or alarm state, and wireless connectivity status icon display 137 that provides indication of wireless communication connection with other devices such as on body electronics, data processing module 160, and/or remote terminal 170. As additionally shown in FIG. 1, display 122 may further include simulated touch screen button 125, 126 for accessing menus, changing display graph output configurations or otherwise for controlling the operation of display device 120.

Referring back to FIG. 1, in certain embodiments, display 122 of display device 120 may be additionally, or instead of visual display, configured to output alarms notifications such as alarm and/or alert notifications, glucose values etc., which may be audible, tactile, or any combination thereof. In one aspect, the display device 120 may include other output components such as a speaker, vibratory output component and the like to provide audible and/or vibratory output indication to the user in addition to the visual output indication provided on display 122. Further details and other display embodiments can be found in, e.g., U.S. patent application Ser. No. 12/871,901, now U.S. Pat. No. 8,514, 086, U.S. Provisional Application Nos. 61/238,672, 61/247, 541, 61/297,625, the disclosures of each of which are incorporated herein by reference for all purposes.

After the positioning of on body electronics 110 on the skin surface and analyte sensor 101 in vivo to establish fluid contact with ISF (or other appropriate body fluid), on body electronics 110 in certain embodiments is configured to wirelessly communicate analyte related data (such as, for example, data corresponding to monitored analyte level and/or monitored temperature data, and/or stored historical analyte related data) when on body electronics 110 receives a command or request signal from display device 120. In certain embodiments, on body electronics 110 may be configured to at least periodically broadcast real time data associated with monitored analyte level which is received by display device 120 when display device 120 is within communication range of the data broadcast from on body electronics 110, i.e., it does not need a command or request from a display device to send information.

For example, display device 120 may be configured to transmit one or more commands to on body electronics 110 to initiate data transfer, and in response, on body electronics 110 may be configured to wirelessly transmit stored analyte related data collected during the monitoring time period to display device 120. Display device 120 may in turn be connected to a remote terminal 170 such as a personal computer and functions as a data conduit to transfer the stored analyte level information from the on body electronics 110 to remote terminal 170. In certain embodiments, the received data from the on body electronics 110 may be stored (permanently or temporarily) in one or more memory of the display device 120. In certain other embodiments, display device 120 is configured as a data conduit to pass the data received from on body electronics 110 to remote terminal 170 that is connected to display device 120.

Referring still to FIG. 1, also shown in analyte monitoring system 100 are data processing module 160 and remote terminal 170. Remote terminal 170 may include a personal computer, a server terminal a laptop computer or other suitable data processing devices including software for data management and analysis and communication with the components in the analyte monitoring system 100. For example, remote terminal 170 may be connected to a local area network (LAN), a wide area network (WAN), or other data network for uni-directional or bi-directional data communication between remote terminal 170 and display device 120 and/or data processing module 160.

Remote terminal 170 in certain embodiments may include one or more computer terminals located at a physician's office or a hospital. For example, remote terminal 170 may be located at a location other than the location of display device 120. Remote terminal 170 and display device 120 could be in different rooms or different buildings. Remote terminal 170 and display device 120 could be at least about one mile apart, e.g., at least about 10 miles apart, e.g., at least about 100 miles apart. For example, remote terminal 170 could be in the same city as display device 120, remote terminal 170 could be in a different city than display device 120, remote terminal 170 could be in the same state as display device 120, remote terminal 170 could be in a different state than display device 120, remote terminal 170 could be in the same country as display device 120, or remote terminal 170 could be in a different country than display device 120, for example.

In certain embodiments, a separate, optional data communication/processing device such as data processing module 160 may be provided in analyte monitoring system 100. Data processing module 160 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 160 may further include communication ports, drivers or connectors to establish wired communication with one or more of display device 120, on body electronics 110, or remote terminal 170 including, for example, but not limited to USB connector and/or USB port, Ethernet connector and/or port, Fire Wire connector and/or port, or RS-232 port and/or connector.

In certain embodiments, data processing module 160 is programmed to transmit a polling or query signal to on body electronics 110 at a predetermined time interval (e.g., once every minute, once every five minutes, or the like), and in response, receive the monitored analyte level information from on body electronics 110. Data processing module 160 stores in its memory the received analyte level information, and/or relays or retransmits the received information to another device such as display device 120. More specifically in certain embodiments, data processing module 160 may be configured as a data relay device to retransmit or pass through the received analyte level data from on body electronics 110 to display device 120 or a remote terminal (for example, over a data network such as a cellular or WiFi data network) or both.

In certain embodiments, on body electronics 110 and data processing module 160 may be positioned on the skin surface of the user within a predetermined distance of each other (for example, about 1-12 inches, or about 1-10 inches, or about 1-7 inches, or about 1-5 inches) such that periodic communication between on body electronics 110 and data processing module 160 is maintained. Alternatively, data processing module 160 may be worn on a belt or clothing item of the user, such that the desired distance for communication between the on body electronics 110 and data processing module 160 for data communication is maintained. In a further aspect, the housing of data processing module 160 may be configured to couple to or engage with on body electronics 110 such that the two devices are combined or integrated as a single assembly and positioned on the skin surface. In further embodiments, data processing module 160 is detachably engaged or connected to on body electronics 110 providing additional modularity such that data processing module 160 may be optionally removed or reattached as desired.

Referring again to FIG. 1, in certain embodiments, data processing module 160 is programmed to transmit a command or signal to on body electronics 110 at a predetermined time interval such as once every minute, or once every 5 minutes or once every 30 minutes or any other suitable or desired programmable time interval to request analyte related data from on body electronics 110. When data processing module 160 receives the requested analyte related data, it stores the received data. In this manner, analyte monitoring system 100 may be configured to receive the continuously monitored analyte related information at the programmed or programmable time interval, which is stored and/or displayed to the user. The stored data in data processing module 160 may be subsequently provided or transmitted to display device 120, remote terminal 170 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 160 transmits a command or signal to on body electronics 110 to receive the analyte related data in response to a user activation of a switch provided on data processing module 160 or a user initiated command received from display device 120. In further embodiments, data processing module 160 is configured to transmit a command or signal to on body electronics 110 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 160 may be programmed to automatically transmit a request command or signal to on body electronics 110. Alternatively, data processing module 160 may be programmed to activate an alarm to notify the user that a predetermined period of time has elapsed since the last communication between the data processing module 160 and on body electronics 110. In this manner, users or healthcare providers may program or configure data processing module 160 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 101) that is outside a predetermined acceptable range indicating a physiological condition which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 110 and output to the user on a user interface of on body electronics 110 so that corrective action may be timely taken. In addition to or alternatively, if display device 120 is within communication range, the output indications or alarm data may be communicated to display device 120 whose processor, upon detection of the alarm data reception, controls the display 122 to output one or more notification.

In certain embodiments, control logic or microprocessors of on body electronics 110 include software programs to determine future or anticipated analyte levels based on information obtained from analyte sensor 101, e.g., the current analyte level, the rate of change of the analyte level, the acceleration of the analyte level change, and/or analyte trend information determined based on stored monitored analyte data providing a historical trend or direction of analyte level fluctuation as a function of time during monitored time period. Predictive alarm parameters may be programmed or programmable in display device 120, or the on body electronics 110, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 120, data processing module 160, and/or remote terminal 170, and/or on body electronics 110. Such information may be displayed as, for example, a graph (such as a line graph) to indicate to the user the current and/or historical and/or and predicted future analyte levels as measured and predicted by the analyte monitoring system 100. Such information may also be displayed as directional arrows (for example, see trend or directional arrow display 131) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 160 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 110, remote terminal 170 or display device 120. In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android', iPhone® operating system, Palm® WebOS', Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 170 may be configured to provide the executable application software to the one or more of the communication devices described above when communication between the remote terminal 170 and the devices are established.

In still further embodiments, executable software applications may be provided over-the-air (OTA) as an OTA download such that wired connection to remote terminal 170 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 160 and/or display device 120.

Referring back to remote terminal 170 of FIG. 1, in certain embodiments, new software and/or software updates such as software patches or fixes, firmware updates or software driver upgrades, among others, for display device 120 and/or on body electronics 110 and/or data processing module 160 may be provided by remote terminal 170 when communication between the remote terminal 170 and display device 120 and/or data processing module 160 is established. For example, software upgrades, executable programming changes or modification for on body electronics 110 may be received from remote terminal 170 by one or more of display device 120 or data processing module 160, and thereafter, provided to on body electronics 110 to update its software or programmable functions. For example, in certain embodiments, software received and installed in on body electronics 110 may include software bug fixes, modification to the previously stalled software parameters (modification to analyte related data storage time interval, resetting or adjusting time base or information of on body electronics 110, modification to the transmitted data type, data transmission sequence, or data storage time period, among others). Additional details describing field upgradability of software of portable electronic devices, and data processing are provided in U.S. application Ser. Nos. 12/698,124, 12/794,721, now U.S. Pat. No. 8,595,607, Ser. Nos. 12/699,653, and 12/699,844, now U.S. Pat. No. 8,930, 203, and U.S. Provisional Application Nos. 61,359,265, and 61/325,155 the disclosure of which is incorporated by reference herein for all purposes.

Embodiments of On-Body Electronics Units

Figures 2A, 2B, 3, 4A:
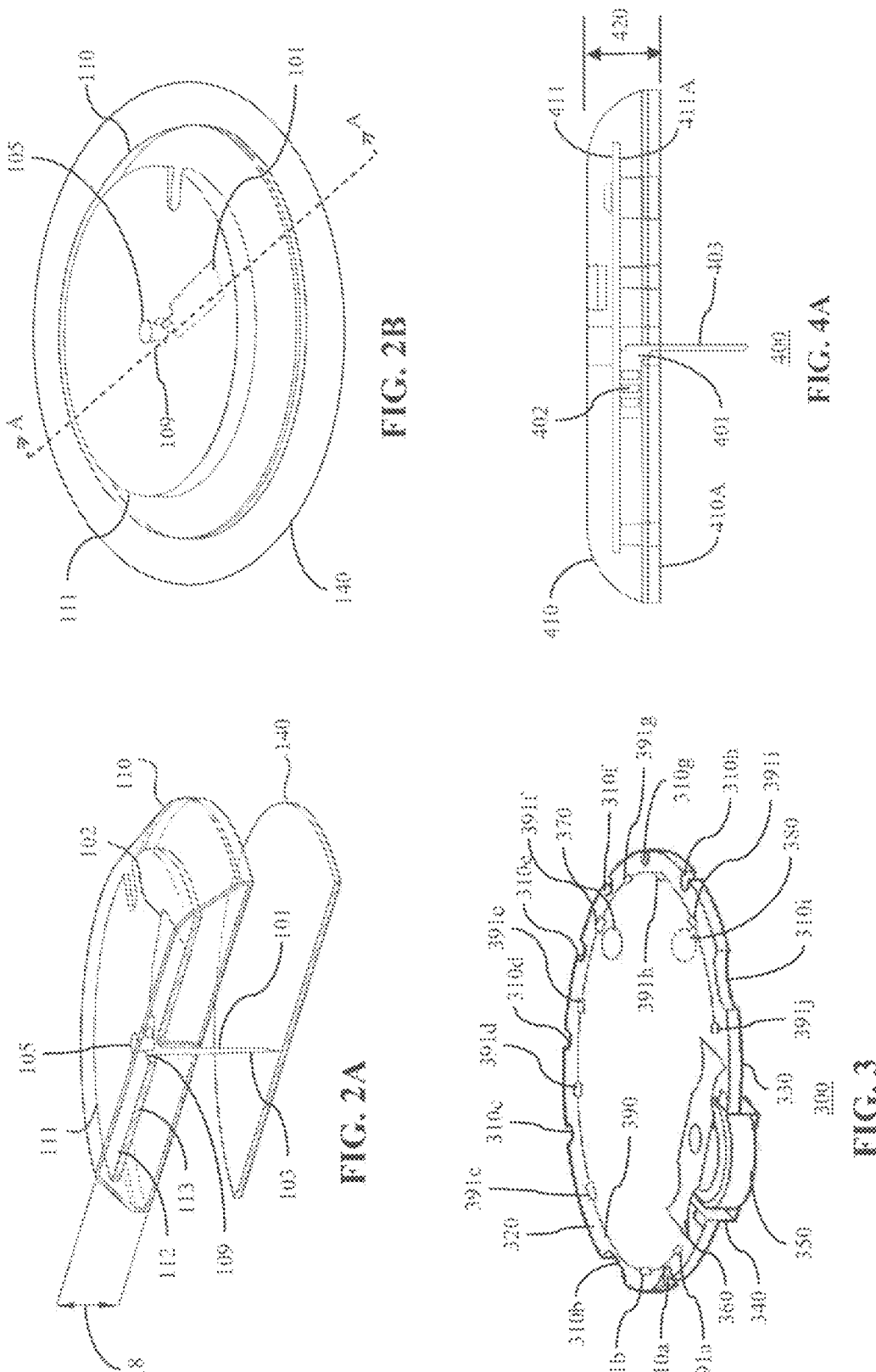
FIGS. 2A-2B are perspective and cross-sectional perspective views, respectively, of the housing including analyte sensor and on body electronics of system in FIG. 1 in certain embodiments.
FIG. 3 illustrates a printed circuit board (PCB) of on body electronics in certain embodiments.
FIG. 4A illustrates a side view of the housing including an analyte sensor and sensor electronics in certain embodiments.

FIGS. 2A-2B are perspective and top cross sectional views, respectively, of on body electronics 110 of FIG. 1 in certain embodiments. In particular, FIG. 2A illustrates the cross-sectional view of on body electronics 110 along the dotted line A shown in FIG. 2B. Referring to FIGS. 2A-2B, on body electronics 110 in certain embodiments is sized and shaped such that the height or thickness profile is minimized (for example, to less than or equal to about 10 mm, e.g., or less than or equal to about 7 mm, e.g., or less than or equal to about 5 mm, e.g., or less than or equal to about 4.5 mm, e.g., or less than or equal to about 4 mm or less). For example, as shown in the figures, in certain embodiments, on body electronics 110 includes a dome-like or tapered shape with a height or thickness dimension of up to about 5 mm at its thickest point, and may taper (gradually or step wise) to a height or thickness dimension of less than about 4 mm, or about 3 mm or less, or about 2 mm or less, or about 1 mm or less. In certain embodiments, on body electronics 110 has a compact z-height 118 (e.g., height or thickness of on body electronics 110) that is not more than about 4.5 mm thick at its thickest area (if the thickness is not uniform or rather varies within a given unit), and no more than about 4.6 mm thick including an adhesive patch.

Referring to FIGS. 2A-2B, in certain embodiments, analyte sensor 101 is assembled during manufacturing with on body electronics 110, for example, and fixedly connected to PCB 111 of on body electronics 110. As shown in FIGS. 2A-2B, proximal portion 102 of sensor 101 is placed on upper surface 112 of PCB 111 and secured to PCB 111 for example, using rivets, fasteners, clamps or the like. The fixedly positioned proximal portion 102 of sensor 101 may be positioned such that proximal portion 102 is electrically coupled to the respective contact points on upper surface 112 of PCB 111. As can be further seen from FIGS. 2A-2B, in such embodiments, the distal portion 103 of sensor 101 is bent or angled such that approximately a 90 degree angle is defined between the proximal portion 102 and distal portion 103 of sensor 101. In certain embodiments, the angle between the proximal portion 102 and distal portion 103 of sensor 101 may be less than about 90 degrees, less than about 80 degrees, less than about 70 degrees, less than about 60 degrees, less than about 50 degrees, less than about 40 degrees, less than about 30 degrees, less than about 20 degrees, or less than about 10 degrees.

Referring still to FIG. 2A-2B, as shown, sensor 101 is positioned relative to PCB 111 such that sensor 101 is positioned through opening 109 defined between upper surface 112 and lower surface 113 of PCB 111. In certain embodiments, PCBs of on body electronics do not include an opening such as that shown in FIGS. 2A-2B.

Furthermore, adhesive layer 140 (single sided or two sided) may be provided to securely position on body electronics 110 on the skin surface during and after sensor deployment. Adhesive may be manufactured so to be attached to the on body unit, or to be attachable post manufacturing, e.g., by a user. In certain embodiments, a sensor insertion process causes the adhesive patch to be attached to the on body unit. In certain embodiments, on body electronics 110 with analyte sensor 101 may be contained or disposed (e.g., during manufacturing) within insertion device 150 (FIG. 1), avoiding the need for a user to align, position, or otherwise connect or couple analyte sensor 101 and on body electronics 110 to insertion device 150 (FIG. 1) prior to the insertion of analyte sensor 101 and initializing on body electronics 110. In certain embodiments, an optional sensor guide 105 is provided to further assist in alignment of the analyte sensor 101 with insertion device 150. Thus, potential misuse, user error, or misalignment of analyte sensor 101 relative to a needle or insertion mechanism of insertion device 150 by the user may be avoided.

Referring to FIGS. 2A-2B, embodiments of on body electronics 110 include dimensions and weight that are optimized for reduction and thus maximized for comfort in use and wear. In certain embodiments, on body electronics 110 has a small on-body footprint, e.g., less than about 50 mm in diameter excluding adhesive patch 140 e.g., less than about 45 mm in diameter excluding adhesive patch 140, e.g., less than about 40 mm in diameter excluding adhesive patch 140, e.g., less than about 35 mm in diameter excluding adhesive patch 140, e.g., less than about 30 mm in diameter excluding adhesive patch 140, where in certain embodiments the on-body footprint may be about 25 mm to about 28 mm excluding adhesive patch 140.

In certain embodiments, on body electronics 110, including adhesive patch 140, has an on-body footprint that is less than about 70 mm in diameter (at its widest if it is not uniform), e.g., less than about 65 mm in diameter, e.g., less than about 60 mm in diameter, e.g., less than about 55 mm in diameter, e.g., less than about 50 mm in diameter, e.g., less than about 45 mm in diameter, e.g., less than about 40 mm in diameter, where in certain embodiments the on-body footprint may be about 35 mm to about 37 mm including adhesive patch 140.

In certain embodiments, adhesive patch 140 has an on body footprint that is less than about 3.0 inches in diameter, e.g., less than about 2.0 inches in diameter, less than about 1.0 inches in diameter, where in certain embodiments an adhesive patch may have a diameter that is 1.0 inch to about 1.5 inches or less.

Embodiments include on body electronics 110 that has a small surface area, e.g., less than about 2 square inches excluding adhesive patch 140, e.g., less than about 1.5 square inches excluding adhesive patch 140, e.g., less than about 1 square inches excluding adhesive patch 140, e.g., less than about 0.9 square inches excluding adhesive patch 140, e.g., less than about 0.8 square inches excluding adhesive patch 140, e.g., less than about 0.75 square inches excluding adhesive patch 140, e.g., less than about 0.7 square inches excluding adhesive patch 140, where in certain embodiments the surface area of an on body electronics unit may be about 0.75 square inches to about 0.79 square inches excluding an adhesive patch.

In certain embodiments, on body electronics 110, including adhesive patch 140, has a surface area that is about 3.0 square inches or less including an adhesive patch, e.g., about 2.0 square inches or less including an adhesive patch, e.g., about 1.9 square inches or less including an adhesive patch, e.g., about 1.8 square inches or less including an adhesive patch, e.g., about 1.75 square inches or less including an adhesive patch, e.g., about 1.6 square inches or less including an adhesive patch, where in certain embodiments the surface area of an on body electronics unit may be about 1.75 square inches to about 1.77 square inches or less.

In certain embodiments, on body electronics 110 may have a circular footprint and/or adhesive patch 140 may have a circular footprint. In certain embodiments, on body electronics 110 may be circular in shape. Other shapes for on body electronics and/or adhesive patches include, but are not limited to oval, rectangle, square triangle, or polygon shapes may also be used, as well as irregular and complex shapes.

In certain embodiments, on body electronics 110 has low mass, e.g., less than about 10 grams including adhesive patch 140 e.g., less than about 5 grams including adhesive patch 140, less than about 3.5 grams including adhesive patch 140, wherein in certain embodiments the mass is no more than 3 grams including adhesive patch 140.

FIG. 3 illustrates a PCB for use in on body electronics in certain embodiments. Referring to FIG. 3, PCB 300 in certain embodiments includes a plurality of notches 310a-310i around an outer periphery of PCB 300. In certain embodiments, notches 310a-310i provide a flowpath during manufacturing for an overmold material to encapsulate first and second surfaces 320, 330 of PCB 300 within a housing of an on body electronics. Referring still to FIG. 3, in certain embodiments, notch 340 is additionally provided on the outer periphery of PCB 300 to receive and retain a battery 350. As shown, battery 350 in certain embodiments is securely retained within notch 340 of PCB 300 using securement element 360 that is fixedly retained on first surface 320 of PCB 300. In certain embodiments, securement element 360 is configured as battery contact terminal to connect the battery to a respective electrical contact on PCB 300 to provide power to the components of PCB 300 in an on body electronics. In certain embodiments, PCB 300 may be encapsulated after all the components including battery 350 and securement element 360 are assembled.

Referring still to FIG. 3, in certain embodiments, an antenna 390 for wireless communication may include surface mounted inductors 391a-391j provided between each of the plurality of notches 310a-310i and 340 of PCB 300 either on a top and/or bottom surface of PCB 300, or at the edge surface of PCB 300 within notches 310a-310i, similar to battery 350 in notch 340. In addition, in certain embodiments, surface mounted thermistors 370, 380 are provided on first and second surfaces 320, 330 of PCB 300 to detect/monitor on skin temperature and ambient temperature.

FIG. 4A illustrates a side view of on body electronics 400 in certain embodiments. Referring to FIG. 4A, on body electronics 400 includes housing 410 with PCB 411 provided therein, PCB 411 having a portion in electrical contact with analyte sensor 401 such that proximal portion 402 of analyte sensor 401 is electrically connected to bottom surface 411A of PCB 411 while distal portion 403 of analyte sensor 401 protrudes outwards or downwards from bottom surface 410A of on body electronics 400. Distal portion 403 of analyte sensor 401 is maintained in fluid contact with, for example, ISF under the skin layer when on body electronics 400 is positioned on the skin surface with analyte sensor 401 transcutaneously positioned for analyte monitoring.

Referring to FIG. 4A, in certain embodiments, PCB 411 and the proximal portion 402 of analyte sensor 401 may be encapsulated either partially or entirely, with potting material. Encapsulation of PCB 411 and proximal portion 402 of analyte sensor 401 provides protection of the electronic components provided on PCB 411 from contaminants and/or moisture. In certain embodiments, PCB 411 includes a data processing or control unit such as one or more microprocessors and/or ASICs, one or more memory or data storage devices such as random access memory (RAM), read only memory (ROM) and the like, to store data and programming and/or control logic or routines to perform the operations related to the processing of signals received from analyte sensor 401. Data processing or control unit may be programmed to perform signal processing such as, for example, but not limited to, analog to digital conversion, signal filtering, storage, data transmission and reception.

Referring still to FIG. 4A, in certain embodiments, analyte sensor 401 is permanently connected to PCB 411, such that the respective electrical contacts of the sensor including electrical contacts for one or more of the electrodes including, for example, a working electrode, a counter electrode, a reference or a counter/reference electrode, in a three electrode system are permanently maintained in electrical communication with respective electrical contacts on PCB 411. In other words, during manufacturing and assembly, analyte sensor 401 and PCB 411 are permanently connected together to provide a fixed electrical coupling. In this manner, in certain embodiments, on body electronics 400 is disabled, deactivated or no longer used after the expiration of the sensor useful life.

Figures 4B, 5, 6, 7A, 7B:
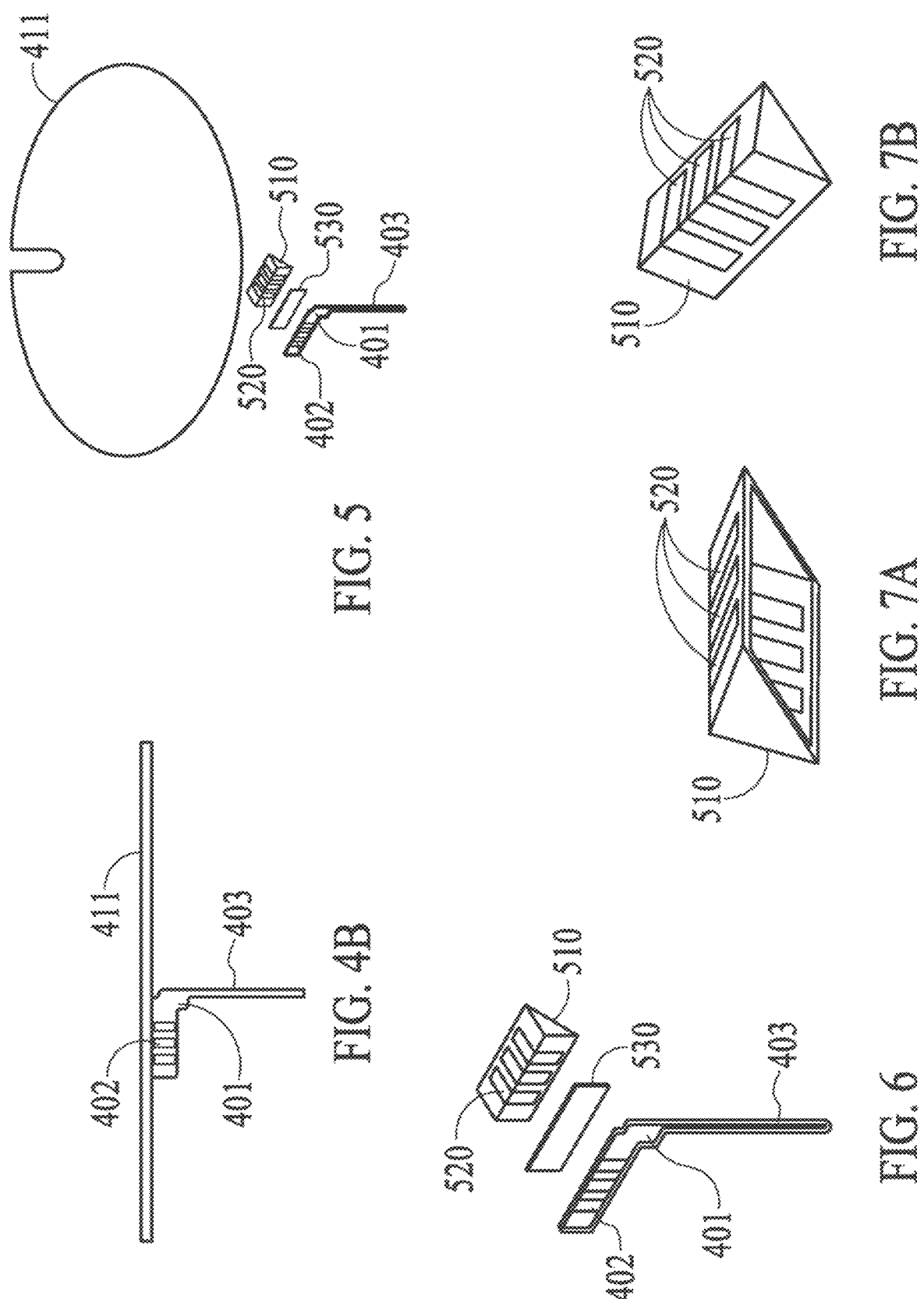
FIG. 4B illustrates a side view of a PCB of the on body electronics assembled with an analyte sensor in certain embodiments.
FIG. 5 is a perspective view of the electronics assembly shown in FIG. 4B with separated components including the PCB and the analyte sensor.
FIG. 6 is a component view of the analyte sensor and interconnect components of FIG. 5 in certain embodiments.
FIGS. 7A-7B are perspective views of the interconnect component of FIG. 5 in certain embodiments

FIG. 4B illustrates a side view of PCB 411 in contact with analyte sensor 401 in certain embodiments with housing 400 removed. Referring to FIG. 4B, analyte sensor 401 is physically attached to PCB 411 without any substantial or significant stress or pressure upon the body of analyte sensor 401 to either bend or otherwise deform the shape of analyte sensor 401 in order to connect the electrodes of analyte sensor 401 to respective electrical contacts on PCB 411 (however, the sensor could be bent if desired, for example, to further minimize the height of the on body electronics assembly). That is, as discussed further in conjunction with FIG. 5 below, sensor 401 may be connected to PCB 411 using an interconnect component that provides electrical connection or coupling between analyte sensor 401 and PCB 411 without deforming or otherwise bending of flexing the body of analyte sensor 401 in order to make the electrical connection.

FIG. 5 is a perspective, exploded view of the components of PCB 411 in contact with the analyte sensor 401 shown in FIG. 4B in certain embodiments. Referring to FIG. 5, proximal portion 402 of analyte sensor 401 is connected to PCB 411 using a conductive film 530 and an interconnect component 510 that includes conductive material 520. That is, in certain embodiments, conductive film 530 is positioned between the proximal portion 402 of analyte sensor 401 and interconnect component 510 such that when analyte sensor 401, conductive film 530 and interconnect component 510 are physically attached, the electrical connection of each of the electrodes of the analyte sensor 401 is maintained via the conductive film 530 and interconnect component 510 to PCB 411.

In certain embodiments, conductive film 530 includes conductive traces or contact points that electrically couple with respective electrical contacts on the proximal portion 402 of analyte sensor 401 to provide a continuous electrical signal path for electrodes of the analyte sensor 401. Furthermore, as shown in FIG. 5, conductive film 530 in certain embodiments may be configured to provide electrical conductivity to at least two (e.g., opposing) surfaces of its body such that when the two surfaces of the conductive film 530 are physically coupled to the interconnect component 510, the continuous electrical signal path for each of the electrodes of the analyte sensor 401 is maintained via the interconnect component 510 to PCB 411.

Referring still to FIG. 5, in certain embodiments, the interconnect component 510 may include a three-sided or more configuration, e.g., a substantially triangular shape or the like. For example, a triangularly shaped interconnect may have a first surface in contact with the respective surface of the conductive film 530, while a second surface of the interconnect component 510 configured for electrical contact with the electrical contact points on PCB 411 is substantially at a right angle relative to the first surface of the interconnect component 510. The defined angular relationship between the first and second surfaces respectively coupling to conductive film 530 and the contact points on PCB 411 substantially define the transcutaneous insertion angle of the analyte sensor 401 relative to PCB 411 of on body electronics 400 (FIG. 4). In certain embodiments, this geometry of interconnect component 510 facilitates the electrical connection between the electrodes of the analyte sensor 401 and the respective electrical contact points on PCB 411 without physically modifying the configuration of either the analyte sensor 401 or PCB 411. Of course, other geometries could be employed as well. For example, different geometries (e.g., based on angular relationships between a first and second surface) of interconnect component 510 provides varied insertion angle of analyte sensor 101 such as, for example, about 90 degrees or less, e.g., about 80 degrees or less, about 70 degrees or less, about 60 degrees or less, about 50 degrees or less, about 40 degrees or less, about 30 degrees or less, or about 20 degrees or less, relative to the skin surface.

In certain embodiments, conductive film 530 includes an anisotropic conductive film while the interconnect component 510 includes molded components which, in combination provide for a reduced height or z-profile 420 of the on body electronics 400 resulting from, for example, the geometry of the interconnect component 510 that provides a planar surface for connection or coupling with analyte sensor 401 and another planar surface for connection to PCB 411. Embodiments also include conductive film 530 that is isotropic, or die cut. In this manner, in certain embodiments, the configuration of the interconnect component 510 provides mechanical fixturing and electrical connection of analyte sensor 401 to PCB 411 of on body electronics 400.

FIG. 6 is a close up detailed perspective view of analyte sensor 401, conductive film 530 and the interconnect component 510 shown in FIG. 5 in certain embodiments. FIG. 7A is a bottom perspective view of the interconnect component 510 shown in FIG. 6 while FIG. 7B is a top perspective view of the interconnect component 510 shown in FIG. 6 in certain embodiments. As can be seen from the figures, analyte sensor 401, conductive film 530 and interconnect component 510 in certain embodiments are sized and shaped to be mated or physically coupled to each other with the conductive film 530 disposed between the respective surfaces of the analyte sensor 401 proximal portion 402 and the first contacting surface of the interconnect component 510.

In this manner, electrical contacts 520 of interconnect component 510 are maintained in signal communication with the respective electrodes of analyte sensor 401 via the conductive film 530 (and to the respective contact points on the printed circuit board (PCB) 411 of on body electronics 400) such that when ready to use, on body device electronics 400 includes PCB 411 connected to analyte sensor 401 in a fixed position relative to each other. Further, as discussed, PCB 411 may be fully or partially encapsulated with potting material such as epoxy, polyurethane or other suitable material or compounds to, for example, protect the components of on body electronics 400 from contaminants or moisture.

In certain embodiments, the conductive film 530 may include anisotropic conductive adhesive film, e.g., such as those available from 3M Corporation, St. Paul, Minnesota, which is heat bondable, electrically conductive and include a thermosetting epoxy/acrylate adhesive matrix with conductive particles that allow interconnection of circuit lines through the adhesive thickness after bonding while providing sufficient space or gap for electrical insulation in the plane of the adhesive.

Furthermore, referring back to FIGS. 5-7B, the interconnect component 510 in certain embodiments may be manufactured using one or more processes of injection molding, laser activation and/or metallization to provide electrical conductive paths (for example, as shown on the surfaces of the interconnect component 510), or assembly procedure to form the desired three dimensional triangular shape with two conductive surfaces at substantially a 90 degree angle relative to each other as shown, for example, in FIGS. 5-7B. In certain embodiments, the two conductive surfaces may be formed at an angle greater or less than 90 degrees relative to each other.

Additionally, in certain embodiments, interconnect component 530 may be configured to be used as a spacer component for a temperature probe (for example, thermistor, a thermocouple, or a resistive thermal device (RTD, or sometimes referred to as resistance temperature detectors)) that detects or monitors the temperature of or around or surrounding analyte sensor 401. In certain embodiments, monitored or detected temperature data may be used to process the signals from analyte sensor 401 to, for example, compensate for potential analyte sensor signal deviation (thus resulting in error) due to temperature change or variation.

Accordingly, in certain embodiments, analyte sensor 401 including sensing chemistry, an analyte flux-limiting membrane and/or other compositions, may be initially manufactured separately from the printed circuit board (PCB) 411 and other components of on body electronics 400, and electrically connected during the final stages of the manufacturing process to electrically connect the electrodes of the analyte sensor 401 to the respective electrical contact points on PCB 411. Use of interconnect component 510 in certain embodiments allows for the initial separate manufacturing of analyte sensor 401 and on body electronics 400, and thereafter, assembled or connected together to form an integrated assembly prior to use.

In certain embodiments, the conductive material for the interconnect component 510 includes conductive traces embedded in a flexible material, such as a flexible strip, which generally can be formed from a thermoplastic material. Suitable thermoplastic materials may include polyimides such as for example, Kapton polyimide film, but other suitable material may be used. In other embodiments, conductive traces are encapsulated in a flexible sheath.

Figure 8C:
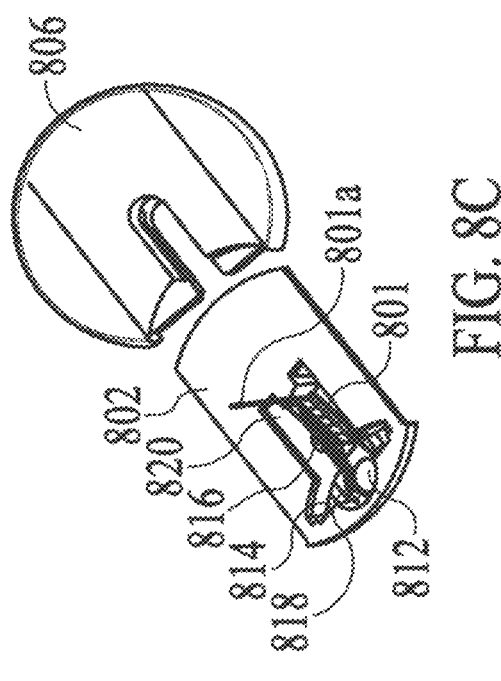
FIGS. 8A-8D illustrate on body electronics including a module interconnect in certain embodiments.
Figure 8D:
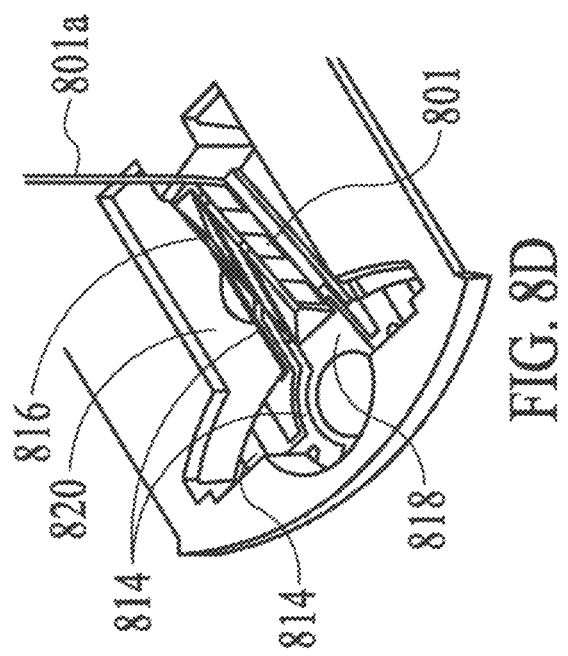
Figure 8A:
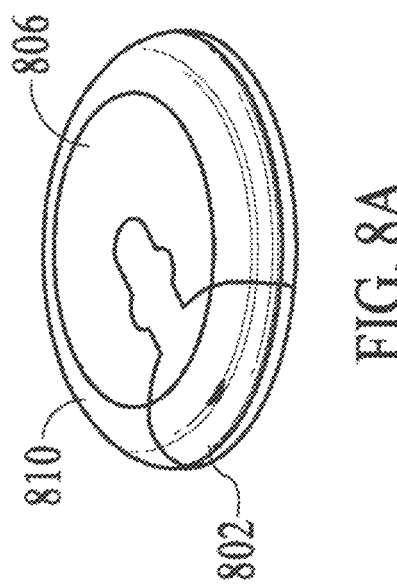
Figure 8B:
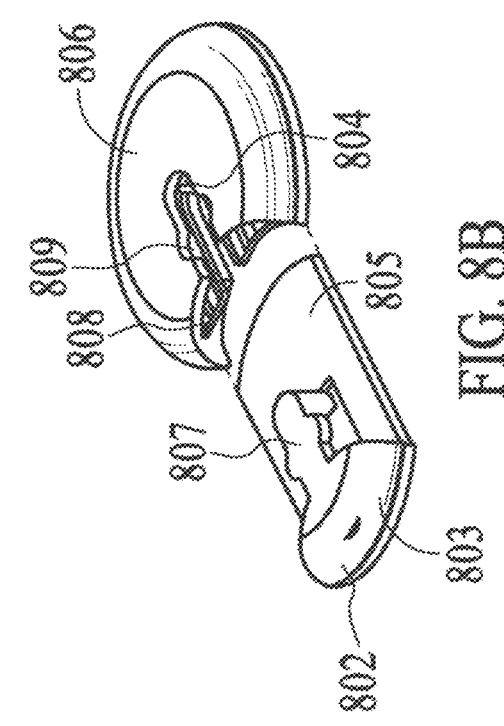

FIGS. 8A-8D illustrate on body electronics including a module interconnect in certain embodiments, with FIGS. 8A-8B illustrating top perspective views, while FIGS. 8C-8D illustrate bottom perspective views. Referring to FIGS. 8A-8D, on body electronics 810 includes modular sensor assembly 802 which includes analyte sensor 801 (see e.g., FIGS. 8C-8D), for engageably coupling with electronics component 806. As illustrated, the modular sensor assembly 802 may be configured to interlock or otherwise engage with the electronics component 806. Accordingly, upon engagement of modular sensor assembly 802 and electronics component 806, on body electronics 810 with analyte sensor 801 may be provided.

In certain embodiments, modular sensor assembly 802 may be a molded device, such as for example, formed by injection molding techniques. As illustrated in FIG. 8B, modular sensor assembly 802 includes bottom surface 805 connected to top surface 807 by sidewall 803. As can be seen in the perspective views of FIGS. 8C and 8D, in certain embodiments, top surface 807 includes conductive material 814 disposed thereon. Further, top surface 807 may include a vertical surface extending downwardly, which may include conductive material 816 disposed thereon. In certain embodiments, conductive material 816 includes conductive traces and/or conductive contacts.

Still referring to the figures, on body electronics 810 in certain embodiments include modular sensor assembly 802 and electronics component 806 configured for a slidable engagement. As illustrated in FIG. 8B, the bottom of electronics component 806 may include a surface 809 configured to slidably receive modular sensor assembly 802. Further, in certain embodiments, top surface 807 of modular sensor assembly 802 may be configured to define a tongue to interlock with a corresponding groove 804 defined in electronics component 806 to define the shape of on body electronics 810.

Electronics component 806 in certain embodiments may include one or more PCBs including conductive material 808 disposed thereon, such as one or more conductive traces and/or conductive contacts. During engagement of electronics component 806 with modular sensor assembly 802, the conductive material 808 can interface with interconnect conductive material 814. Thus, during engagement, the electronics component 806 and modular sensor assembly 802 establishes electrical communication.

As illustrated in FIG. 8C, modular sensor assembly 802 includes analyte sensor 801 secured or otherwise coupled to a surface 818 of the modular sensor assembly 802. For example, analyte sensor 801 may be coupled to the vertical surface extending from the top surface 807 of the modular sensor assembly 802. In this manner, the vertical surface includes conductive material, such as conductive contacts 816 that connect with the one or more conductive contacts of analyte sensor 801 to establish an electrical communication between analyte sensor 801 and modular sensor assembly 802.

In certain embodiments, as best illustrated in FIGS. 8C and 8D, analyte sensor 801 may be mounted to sidewall 803 of modular sensor assembly 802. In this embodiment, distal portion 801a of analyte sensor 801 is inserted perpendicular to the skin (not shown). In this regard, the bottom surface 805 of the modular sensor assembly 802 includes an aperture 820 (FIGS. 8C and 8D) to permit the distal portion 801a of analyte sensor 801 to extend from the bottom of on body electronics 810 such that distal portion 801a of analyte sensor 801 may be implanted into the body of a user when in use. In certain embodiments, modular sensor assembly 802 may also include a power source 812, such as a battery. Power source 812 may provide power via conductive traces 814 to the electronics component 806. In this manner, the electronics component 806 may be powered by power source 812 of modular sensor assembly 802 such that the electronics component 806 does not need an internal power source.

The conductive material disposed on the modular sensor assembly 802 and/or the electronics component 806 and analyte sensor 801 may include conductive film, such as but not limited to, an anisotropic film. Conductive material, such as the conductive film and/or the Zebra style connector, can provide both a mechanical and electrical connection between modular sensor assembly 802 and sensor 801 or electronics component 806. Modular sensor assembly 802, analyte sensor 801, and electronics component 806 may also be bonded together utilizing an adhesive, such as a UV curable adhesive, or a multi-adhesive, such as a silver loaded epoxy can be used. Other adhesives can alternatively be employed.

FIGS. 9A-9J illustrate on body electronics including an analyte sensor and the PCB provided in the housing of the on body electronics in certain embodiments. Referring to the Figures, in certain embodiments, the analyte sensor 901 is electrically connected to the printed circuit board 911 during manufacturing of the on body patch assembly such that the position of the analyte sensor 901 is fixed relative to the printed circuit board 911 prior to and during use. For example, referring to FIGS. 9A and 9B, as shown, the analyte sensor 901 is electrically connected to the printed circuit board 911 such that the respective contact pads 904 on the analyte sensor 901 are soldered, jet bonded, or otherwise electrically connected to the respective one of the contact points 960 on the printed circuit board 911. In certain embodiments, printed circuit board 911 may include a hole 915 for guiding and/or aligning insertion needle assembly 930 (FIG. 9E) and the sensor distal portion 903.

Figures 9A, 9B, 9C, 9D:
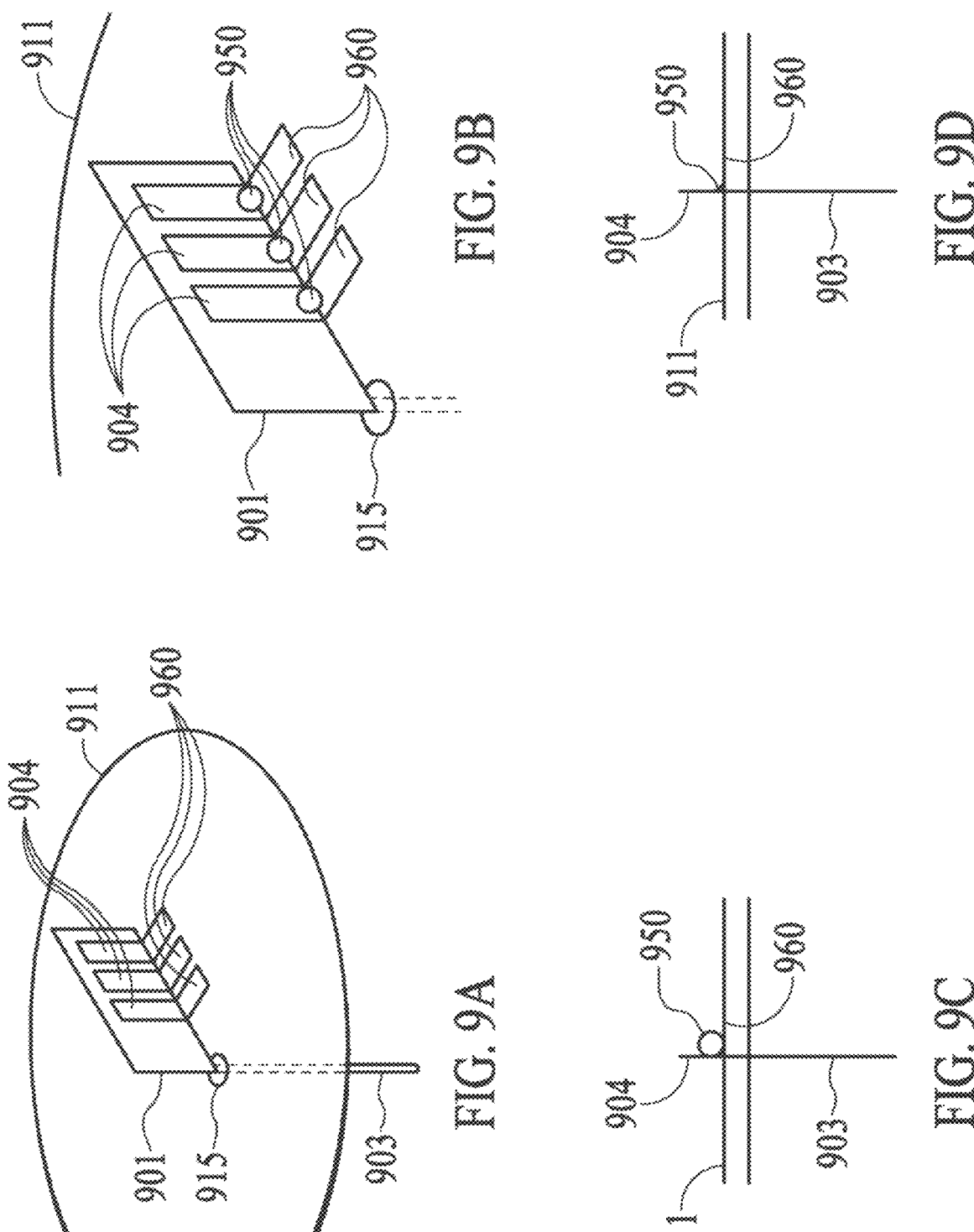

In certain embodiments, as shown in FIG. 9C, conductive material 950 such as solder, gold, silver, silver filled epoxy, copper or other suitable material is separately provided on each of the contact pads 904 of analyte sensor 901 so as to establish electrical connection with the respective contact points 960 on PCB 911. A side cross sectional view of such connection is shown in FIGS. 9C and 9D where the analyte sensor 901 is permanently connected to PCB 911, for example, at a substantially 90 degree angle relative to PCB 911 or at other suitable angles. In FIGS. 9C-9D, it can be seen that wetted solder or conductive adhesive 950 is provided to establish permanent electrical connection between the contact pads 904 of the analyte sensor 901 and the respective contact points 960 on the printed circuit board 911. More specifically, FIG. 9D shows conductive material 950 after it has been applied and integrated with the contact point 960 on PCB 911, while FIG. 9C shows conductive material 950 applied on the contact point 960 on PCB 911 before it is integrated with it to form the electrical connection.

Referring still to the Figures, while the connection between analyte sensor 901 and PCB 911 is shown and described as a 90 degree angle, in certain embodiments, the relative angle between the sensor 901 and printed circuit board 911 may vary and include one or more angles less than 90 degrees relative to each other, such as about 80 degrees or less, about 70 degrees or less, about 60 degrees or less, about 50 degrees or less, about 45 degrees or less, about 40 degrees or less, about 30 degrees or less, or about 20 degrees or less. Furthermore, in certain embodiments, the attachment or connection of the analyte sensor 901 to the printed circuit board 911 may include conductive adhesive bonding, gold ball bonding, silver ball bonding, solder jet bonding, or other suitable equivalent bonding techniques.

Referring to FIGS. 9E-91, certain embodiments include a mounting bracket 910 for retaining analyte sensor 901 in position relative to PCB 911 during manufacturing and/or use. More specifically, in certain embodiments, mounting bracket 910 includes a guide or a hole 905 for alignment of insertion needle 930 and distal portion 903 of analyte sensor 901 coupled with insertion needle 930 prior to and during the insertion of analyte sensor 901. Mounting bracket 910 may be further be configured to retain or assist in the withdrawal of insertion needle 930 after transcutaneous placement of analyte sensor 901 distal portion 903. As shown, FIGS. 9G-91 illustrate a top planar view, a side planar view and a bottom planar view, respectively, of mounting bracket 910 in certain embodiments. Also shown is guide or hole 905 in mounting bracket 910 discussed above for guiding and/or aligning insertion needle 930 and sensor distal portion 903.

Referring back to the Figures, FIG. 9E illustrates a component view of insertion needle 930, mounting bracket 910, analyte sensor 901, and PCB 911, while FIG. 9F illustrates an assembled view of insertion needle 930, mounting bracket 910, analyte sensor 901, and PCB 911. In certain embodiments, insertion needle 930 includes an opening along a longitudinal side for disengaging with analyte sensor 901 when on body electronics 902 is placed on the skin surface, with distal portion 903 of analyte sensor 901 positioned under the skin surface in fluid contact with ISF. Again, guide or hole 905 of mounting bracket 910 in certain embodiments guides or assists the withdrawal or retraction of insertion needle 930 after transcutaneous sensor placement. In certain embodiments, mounting bracket 910 may be fabricated using injection molding process or other suitable processes.

Referring still to the Figures, in certain embodiments, optional features such as support 990 for positioning and maintaining analyte sensor 901 in the desired orientation or position relative to PCB 911 during on body electronics assembly is shown in FIG. 9J. Also shown in FIG. 9J is insertion needle guide 980 having distal portion 903 of analyte sensor 901 provided therethrough. Support 990 may include additional protrusions, dimples or accents on its side facing the top surface of the PCB 911 to assist and/or guide the orientation of analyte sensor 901 during assembly of on body electronics 902.

In this manner, in certain embodiments, analyte sensor 901 may be permanently connected to PCB 911 of on body electronics such that the formed integrated assembly is used and discarded together based on the use of the analyte sensor.

FIGS. 10A and 10B illustrate a top planar view and a cross sectional view, respectively, of an antenna and electronic circuit layout of the on body electronics for use in the analyte monitoring system 100 of FIG. 1 in certain embodiments. More particularly, FIG. 10B is a cross sectional view along the dotted line B shown in FIG. 10A in certain embodiments. Referring to FIGS. 10A and 10B, antenna 1010 in certain embodiments includes a conductive material 1001, such as a PCB copper trace or the like, provided on a substrate 1002, and further, a plurality of inductors 1003a-1003e disposed on the substrate 1002 and electrically connected to the conductive layer 1001 in a loop configuration. In certain embodiments, inductors 1003a-1003e are spaced equidistantly from each other in the loop configuration.

In this embodiment, the loop is positioned substantially near the perimeter of the substrate, e.g., within about 50 mm or less, e.g., within about 40 mm or less, within about 30 mm or less, within about 20 mm or less, within about 10 mm or less, within about 5 mm or less, within about 3 mm or less, within about 1 mm or less. The looping and/or perimeter positioning further increases the area (or length) of the antenna, thereby increasing the transmission range of the antenna, for example. In certain embodiments, some or all of the inductors 1003a-1003e may not be spaced apart equidistant from each other. Also shown in FIGS. 10A and 10B is ASIC and/or microprocessor 1004 in electrical communication with the conductive layer 1001 for processing signals from an in vivo analyte sensor (not shown) and interfacing with the sensor in addition to processing the commands or signals from display device 120 (FIG. 1) and generating and/or providing the response data packet to display device 120.

FIG. 11 illustrates a top planar view of an antenna layout on the circuit board of on body electronics in certain alternate embodiments. Referring to FIG. 11, compared to antenna 1010 of FIGS. 10A and 10B, antenna 1110 of the on body electronics shown in FIG. 11 may be provided around only a portion or section of the outer periphery of PCB 1102, and radially wound substantially around the portion or section of the outer periphery of PCB 1102. For example, as shown in FIG. 11, the conductive trace forming the antenna 1110 may be provided in a looped, threaded manner such that the continuous trace is alternatingly provided on the top and the bottom surfaces of PCB 1102 along the portion of its outer edge or periphery, and/or threaded through the PCB 1102 repeatedly with each loop about the periphery of PCB 1102. In certain embodiments, such looping back and forth between the top and bottom surfaces of PCB 1102 may be about most or all of the perimeter of PCB 1102.

In certain embodiments, antenna 1110 shown in FIG. 11 provides for lower manufacturing cost by reducing the antenna components and importantly may require less space on PCB 1102 which further enables miniaturization of an on body electronics unit. For example, configuration of antenna 1110 in the embodiment shown in FIG. 11 obviates the need for separate inductors as compared to the antenna configuration shown in FIGS. 10A and 10B. As such, the diameter of the overall PCB 1102 may be reduced by about 10% or more, about 15% or more, about 20% or more, about 25% or more, or about 30% or more. Also shown in FIG. 11 is microprocessor and/or ASIC 1104, in electrical communication with the antenna 1110 for processing signals from an in vivo analyte sensor (not shown) and interfacing with the sensor in addition to processing the commands or signals from display device 120 (FIG. 1) and generating and/or providing the response data packet to display device 120.

In the manner described above and shown in conjunction with FIGS. 10A-10B and 11, in certain embodiments, on body electronics antenna 1010, 1110 may be printed as an internal conductive layer of PCB surrounded by the ground plane on the top and bottom layers of PCB. That is, in one aspect, the top and bottom conductive layers may be separated by layers of one or more dielectrics and a conductive layer with a loop antenna disposed therebetween as shown in FIG. 11. Alternatively, antenna for on body electronics may be printed on the top substrate 1002 in series with a plurality of inductors 1003a-1003e as shown in FIGS. 10A and 10B. In certain embodiments of antenna with inductors, the number of inductors may range from about 2 to about 10, for example, about 3 to about 7, or about 5 in some embodiments.

Figure 12A:
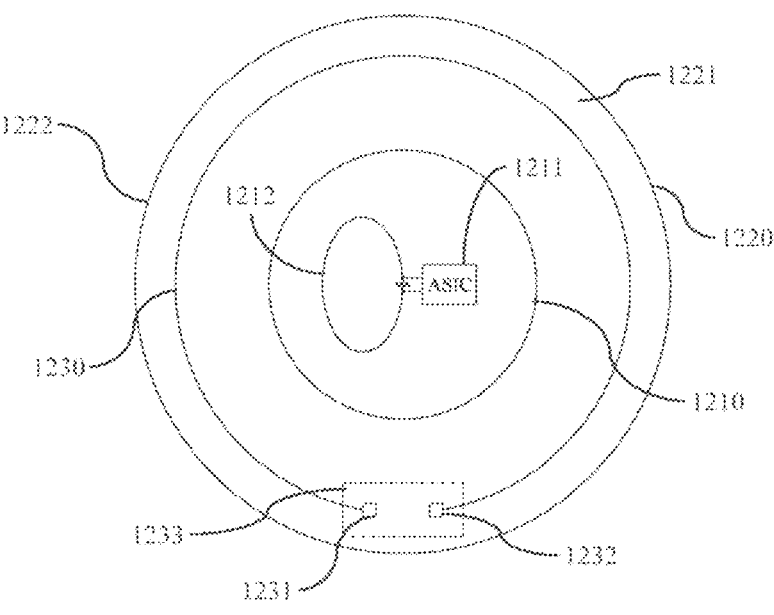
FIGS. 12A-12C illustrate an antenna configuration of the on body electronics in certain embodiments.
Figure 12B:
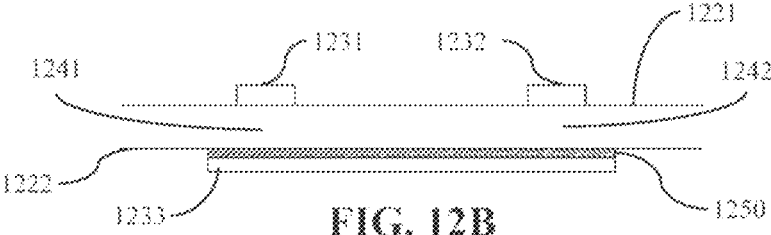
Figure 12C:
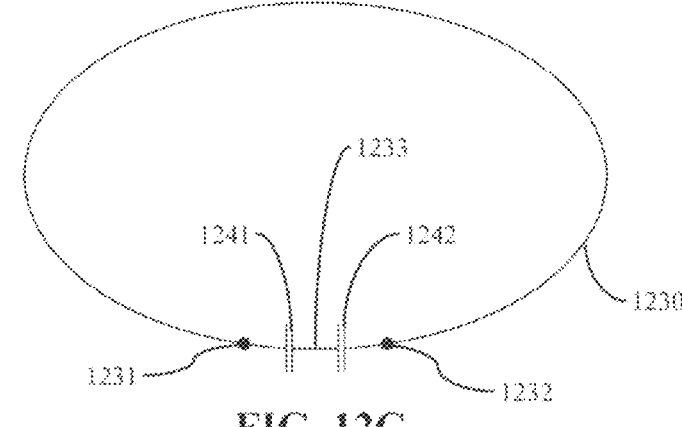

FIGS. 12A-12C illustrate an antenna configuration for on body electronics 1210 in certain embodiments. In particular, FIG. 12A illustrates an embodiment of on body electronics 1210 with adhesive layer 1220 which includes an antenna 1230, FIG. 12B illustrates a cross sectional view of on body electronics 1210 and adhesive layer 1220 shown in FIG. 12A, and FIG. 12C illustrates an equivalent circuit diagram of the terminals and the capacitances from the antenna on the adhesive layer of FIG. 12B.

Referring to FIG. 12A, embodiments include on body electronics 1210 mounted to adhesive patch layer 1220 that includes an antenna 1230 on surface 1221 of adhesive layer 1220. On body electronics 1210 in certain embodiments includes data control and logic implemented in ASIC 1211 that is coupled to antenna 1212 for data communication. As shown in FIG. 12A, antenna 1212 of on body electronics 1210 in certain embodiments may include a loop antenna operatively coupled to ASIC 1211 on a PCB of the on body electronics 1210.

Referring back to FIG. 12A, antenna 1230 in certain embodiments includes copper, aluminum, or other suitable material, and may further include a single, double or multiple loop antenna disposed around a periphery of the adhesive layer 1220. As further shown, antenna 1230 in certain embodiments includes two terminals 1231, 1232 which, in certain embodiments include capacitive terminals that may be formed of the same material as loop antenna 1230 such as copper or aluminum. As shown in FIG. 12A, terminals 1231, 1232 of antenna 1230 are positioned on adhesive layer 1220 such that the terminals 1231, 1232 do not contact each other. Referring now to FIGS. 12A and 12B, on surface 1222 of adhesive layer 1220, terminal 1233 is provided with dielectric layer 1250 positioned between surface 1222 of adhesive layer 1220 and terminal 1233. Terminal 1233, in certain embodiments, includes a capacitive terminal that may be formed of the same material as terminals 1231, 1232. In other embodiments, terminal 1233 may be formed of different material than material used to form terminals 1231, 1232.

Furthermore, as can be seen from the cross sectional view of FIG. 12B, terminal 1233 is sized and positioned on surface 1222 of adhesive layer 1220 such that terminals 1231, 1232 are positioned on surface 1221 of adhesive layer 1220 within a surface area of the adhesive layer 1220 that includes the surface area on surface 1222 of the adhesive layer where terminal 1233 is positioned. In this manner, capacitance 1241 is formed between terminal 1231 and terminal 1233, and capacitance 1242 is formed between terminal 1231 and terminal 1233.

Referring again to FIG. 12B, in certain embodiments, dielectric layer 1250 provided between terminal 1240 and surface 1222 of adhesive layer 1220 includes material with relatively high dielectric constant (for example, materials with dielectric constant of greater than about 90 or more) increases capacitances 1241, 1242 generated between terminal 1231 and terminal 1233, and between terminal 1222 and terminal 1233, respectively. In this manner, capacitances 1241, 1242 in certain embodiments are used to control the inductance to tune antenna 1230 on adhesive layer 1220 to the same frequency of the antenna 1212 of on body electronics 1210. Tuning antenna 1230 to the same frequency as the frequency of antenna 1212 extends the transmission range of on body electronics 1210 for signal communication with display device and/or other components of the overall system 100 (FIG. 1). For example, by tuning antenna 1230 on adhesive layer 1220 to the frequency of antenna 1212 of on body electronics 1210, the transmission range of on body electronics 1210 for signal communication with display device 120 (FIG. 1) or other components of the system 100 (FIG. 1) may be increased by about 25%, about 50%, about 100%, about 150% or about 200% of the transmission range using the antenna 1220 of on body electronics 1210 only.

In the manner described, in certain embodiments, additional single or multiple loop antenna disposed on an adhesive layer or other components separate from the PCB of on skin electronics extends data transmission range for signal communication without requiring additional antenna within the on skin electronics. Furthermore, capacitances 1241, 1242 in certain embodiments can be modified by using dielectric layer 1250 with a different dielectric constant provided between adhesive layer 1220 and terminal 1222. In other embodiments, dielectric layer 1250 may be optional and not included between adhesive layer 1220 and terminal 1233 to achieve the desired capacitance 1241, 1242.

Figure 13:
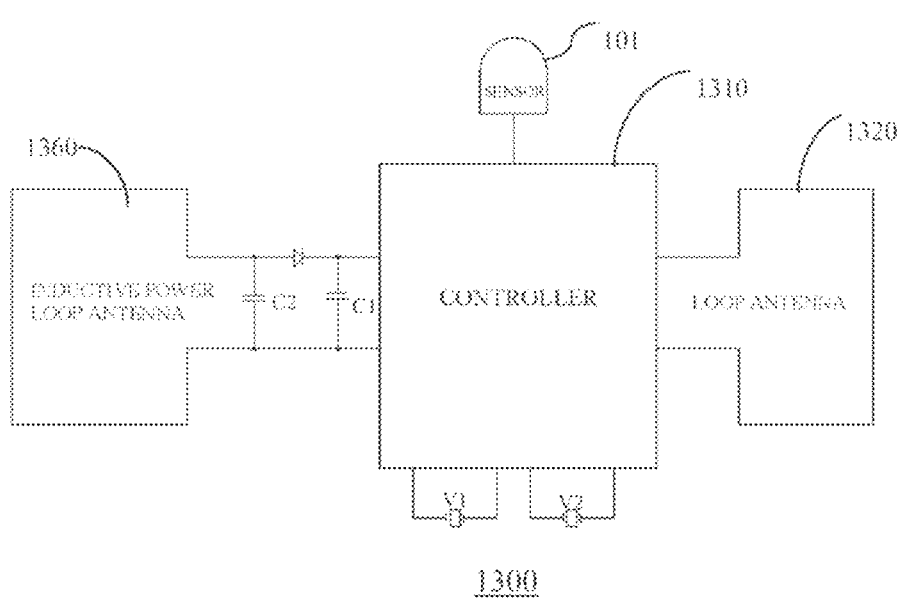
FIG. 13 is a schematic of an on body electronics in the analyte monitoring system 100 of FIG. 1 in certain embodiments.

FIG. 13 is an exemplary schematic of an on body electronics including an in vivo analyte sensor and sensor electronics component for use in the analyte monitoring system 100 of FIG. 1 in certain embodiments. As shown in FIG. 13, on body electronics 1300 of the analyte monitoring system 100, in certain embodiments includes a loop antenna 1320 for transmitting the analyte related data to the display device 120 (or other component or device in the system 100 (FIG. 1)). Inductive power loop antenna 1360 for processing the RF power from display device 120 is provided, which in certain embodiments converts the RF power from display device 120 (FIG. 1) to corresponding DC power for the operation of the on body electronics 1300. In this manner, in certain embodiments, on body electronics 1300 may be configured to operate as a passive data communication component, adopting inductive coupling power without a separate power supply or battery for data transmission.

Furthermore, on body electronics 1300 in certain embodiments does not require a mechanism to initialize the device to place it in its operational mode (turn on the device) nor to deactivate or turn off (or power down) on body electronics 1300. That is, on body electronics 1300 may be initialized and enters an active or operational mode when it detects the RF power from a display device. After initialization, on body electronics 1300, in certain embodiments, upon detection of radiated RF power from a display device, data communication components of on body electronics 1300 enters an active communication mode to transmit and/or receive data packets or otherwise communication with a display device.

Referring back to FIG. 13, also provided is a plurality of super capacitors C1, C2 coupled to inductive power loop antenna 1360 and controller 1310. Referring still to FIG. 13, controller 1310 may be provided on a PCB assembly including the loop antenna 1320, thermistor is provided (not shown), analyte sensor contacts for coupling to the electrodes of an analyte sensor, one or more storage devices such as non-volatile memory (not shown), and other discrete components. In certain aspects, the PCB assembly may be partially or fully encapsulated with, for example, potting material for protection from moisture and/or contaminants.

Figure 14A:
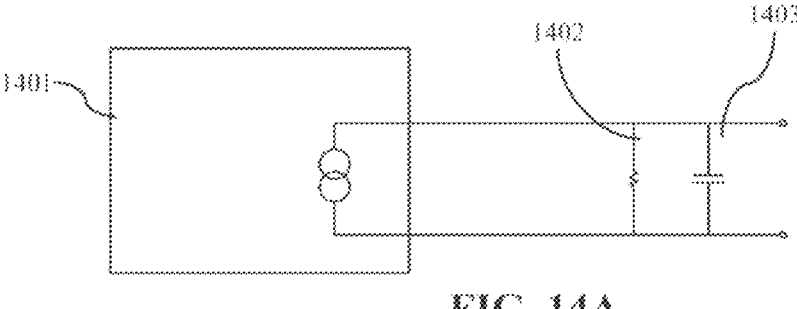
FIGS. 14A-14E illustrate on body electronics configurations of analyte monitoring system 100 of FIG. 1 in certain embodiments.

FIG. 14A illustrates an embodiment of an input circuit for connection between an in vivo analyte sensor and on body electronics. Referring to FIG. 14A, in certain embodiments, sensor 1401 may also function as an electrolytic current source, and its output coupled with a resistor 1402. Voltage developed across resistor 1402 can be measured, to provide a value indicative of analyte concentration. In certain embodiments, while sensor 1401 may function as the electrolytic current source, and thus configured to generate a signal that is correlated with the monitored analyte level without a separate power supply, the on body electronics coupled to sensor 1401 may include a power supply to provide power to operate the components of the on body electronics. For example, the power supply provided on the on body electronics may be used to provide power to the microprocessor and/or ASIC of the on body electronics to convert and/or filter and/or smooth and/or clip and/or average and/or correct and/or otherwise process the signals received from sensor 1401 and/or to store data associated with the signals from sensor 1401.

In addition, capacitor 1403 may be provided in parallel or series with resistor 1402, such that the signal from analyte sensor 1401 may be smoothed. The instantaneous reading from the sensor assembly may provide a time-averaged signal, or alternatively, a series of resistor-capacitor elements could be coupled to provide readings indicative of a time trend. In such embodiments, separate power supply to power the sensor 1401 is not necessary. In such embodiments, on body electronics 110 may not include a separate power supply and rather, include a self-powered sensor as described in further detail in U.S. patent application Ser. No. 12/393,921, 61/325,260, and 61/247,519 incorporated by reference herein for all purposes.

In certain embodiments, passive electronic (analog) components may be used to generate average and/or trend data. For example, by adding a capacitor (such as capacitor 1403) in parallel to current-measuring resistor 1402, the resulting measured voltage signal is a smoother signal than the original signal without the capacitor. Spikes, discontinuities and other rapid changes in the signal are removed or slowed down by the capacitor.

The averaging process in certain embodiments may generate a time shift (delay) in the measured signal, and circuits may be provided to derive information related to the monitored analyte level from such delays.

One type of passive circuit that may be employed to generate signals indicative of data trends over time comprises network of a plurality of parallel resistor-capacitor pairs connected in series, wherein the current provided by the analyte sensor is directed through the two ends of the network and the respective smoothed and time-shifted signal measurements are taken across each resistor-capacitor pair.

Figure 14B:
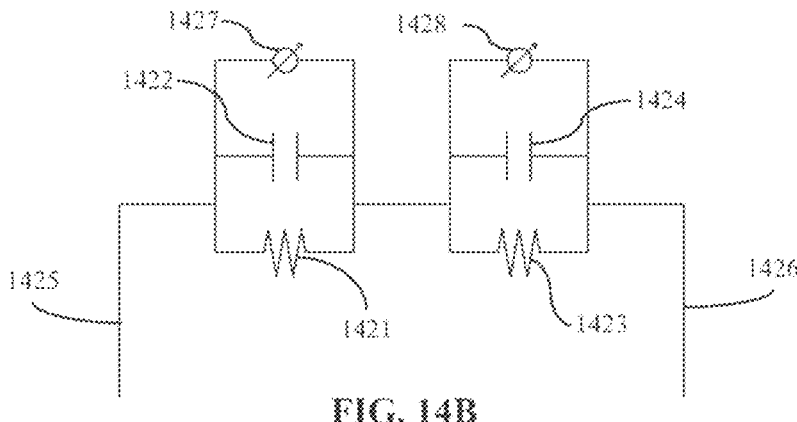

FIG. 14B illustrates such a network, comprising two resistor-capacitor pairs, resistor 1421 in parallel with capacitor 1422, and resistor 1423 in parallel with capacitor 1424, with the two resistor-capacitor pairs connected in a series connection between working electrode 1425 and counter electrode 1426. Measurement points for voltages 1427 and 1428, indicative of analyte concentration, are disposed respectively across each of the two parallel resistor-capacitor pairs. In this network, the two resistors 1421 and 1423 are both of approximately equal resistance, in this embodiment, approximately 5 Megaohms (the exact resistance of the resistors may not be critical, as long as it is sufficiently high to limit current flow). In certain embodiments, resistance may be maintained approximately equal between the resistors to equivalently scale the respective voltage measurements.

To achieve the desired delay, in certain embodiments, the capacitance of capacitor 1422 is greater than the capacitance of capacitor 1424. In this embodiment, the measured voltages 1427 and 1428, provide two analyte measurement signals with different time delays. If the signal is increasing, the more averaged signal 1427 will be lower than the less averaged signal 1428. When the signal is decreasing the situation is reversed. This information is generated passively, powered by the electricity generated by analyte sensor 1401 (FIG. 14A). In this manner both quantitative analyte measurements, and the measurement trend data can be obtained.

Figure 14C:
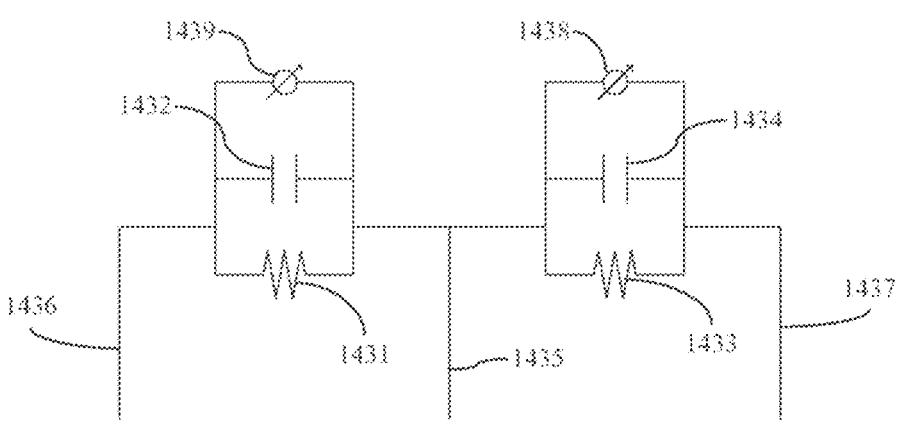

FIG. 14C shows an electronic circuit in which sensor 1401 (FIG. 14A) has a working electrode 1435, and two counter electrodes 1436 and 1437, with signal current split between the two counter electrodes, in certain embodiments. Working electrode 1435 is connected to the circuit between the respective resistor-capacitor parallel pairs resistor 1431 and capacitor 1432, and resistor 1433 and capacitor 1434, and the counter electrodes 1436 and 1437 are connected to the respective ends of the network. Again, the resistors are each approximately 5 Megaohms and capacitor 1432 has higher capacitance than capacitor 1434. In this manner, two voltage signals 1439 and 1438 across capacitor 1432 and capacitor 1434, respectively are generated, one signal with a larger delay compared to the other. The capacitors 1432 and 1434 again determine the delays corresponding to the two arms of the circuit.

Figure 14D:
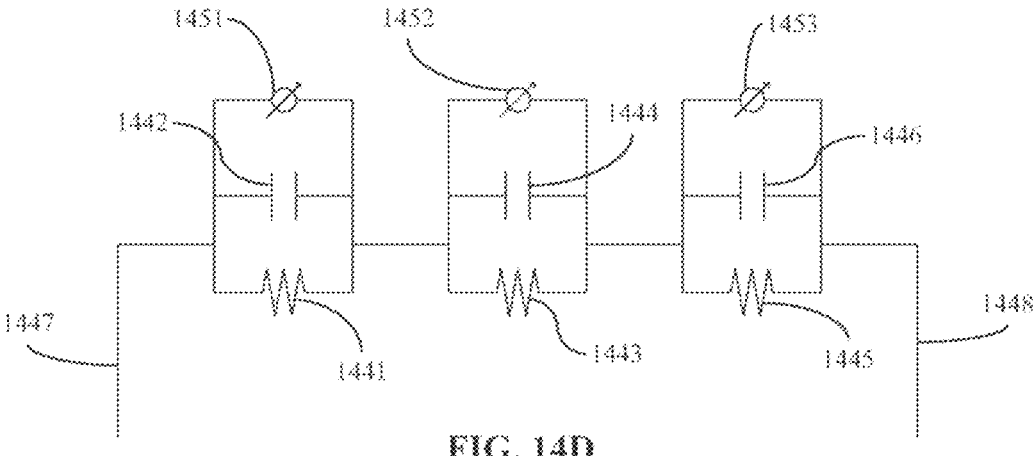

A higher resolution of the analyte level trend especially during periods were the analyte level trend is changing (peaks and valleys) may be achieved by using a greater number of parallel resistor-capacitor elements in series and measuring the potential drop at each of the elements simultaneously. This is illustrated in FIG. 14D, which shows measurements taken across three series resistor-capacitor pairs between working electrode 1447 and counter electrode 1448. In this embodiment, capacitor 1442 has higher capacitance than capacitor 1444, which has higher capacitance than capacitor 1446, and the three resistors 1441, 1443 and 1445, are of approximately equal resistance, of about 5

Megaohms. In this manner three voltage signals 1451, 1452, and 1453 across capacitor 1442, capacitor 1444, and capacitor 1446, respectively are generated, each voltage signal 1451, 1452, 1453 with a different delay compared to each other. In certain embodiments, the size of the capacitance of capacitors 1442, 1444, and 1446 determines the delays corresponding to the arms of the circuit.

Figure 14E:
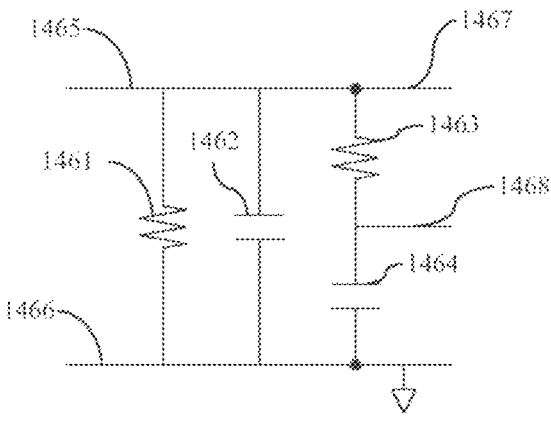
Figure 15:
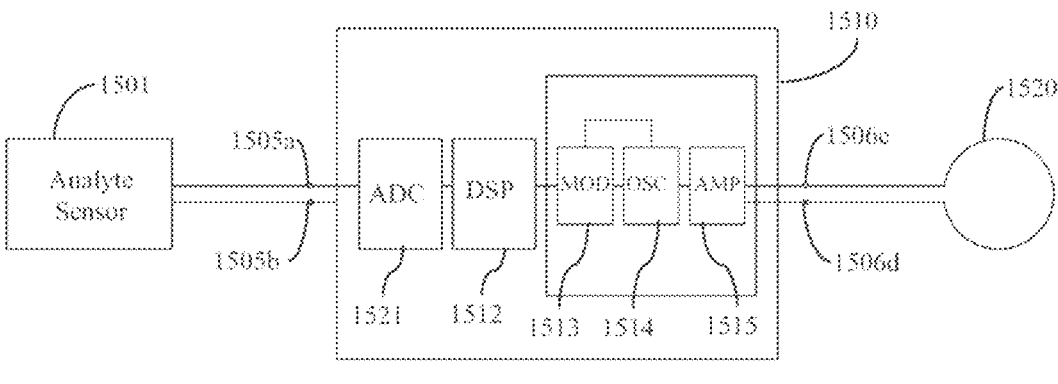
FIG. 15 is a block diagram of illustrating an on body electronics of analyte monitoring system 100 of FIG. 1 in certain embodiments.

Referring now to FIG. 14E, shown is an alternative circuit to the ones depicted in FIGS. 14B-14D. As shown, this circuit allows any value of resistor-capacitor pair 1463/1464 to be chosen without any effect on the scale factor of the sensor with work electrode 1465 and counter electrode 1466. In this embodiment, resistor 1463 x capacitor 1464 is greater than capacitor 1462 x resistor 1461 and resistor 1461 is approximately 5 Megaohms. The voltages 1467 and 1468 are referenced to the transmitter signal ground and measure the un-lagged sensor output on voltage 1467 and the time lagged output on voltage 1468. These two voltages are measured by a circuit that has a very high input impedance. For example, it may be reasonable to achieve 10 Gigaohms input impedance in ASIC 1510 (FIG. 15).

Consequently there may be no electrical "loading" effects on the signal. Any value of resistor 1463 may be selected allowing a small value of capacitor 1464 that is physically smaller and less expensive. Similar to the parallel resistor-capacitor circuit described in FIG. 14D, additional time delayed signals may be obtained with the addition of more segments of resistors and capacitors similar to resistor-capacitor pair 1463/1464.

Delay and smoothing circuits such as those shown in FIGS. 14B-14E may be incorporated in an embodiment such as sensor assembly 1500 (FIG. 15) by providing additional inputs to ASIC 1510 (FIG. 15) or corresponding electronics. The signals provided may be selectively accessed through the ASIC for use in interfaced devices including on-demand devices, periodic reading devices, and data loggers, as required by the reading or logging application. The respective measurements can be appropriately coded into the RF transmission stream from sensor assembly 1500, and decoded and used as needed for the functions performed by the particular interfaced device.

If ASIC 1510 (FIG. 15) is part of the sensor, then ASIC 1510 can be programmed with a unique ID number. If ASIC 1510 is separate from the sensor, then it may be feasible to add a unique resistor to the sensor that would allow identification of the sensor. For example, the resistor could be a laser trimmed resistance in a range of values, with around 50 different values. ASIC 1510 could be made to read that resistance so that if a user attempted to re-use the same sensor the system software would recognize a re-use occurrence.

FIG. 15 is a block diagram of the components of on body electronics in certain embodiments. More specifically, on body electronics 1500 in certain embodiments does not include a dedicated power supply and is configured to provide analyte concentration data in processed digital format. In such embodiments, the data processing functionality of on body electronics 1500 may include analog to digital converter (ADC) 1521 and digital signal processor (DSP) 1512. ADC 1521 and DSP 1512 may be integrated with one or more oscillators 1514, modulator 1513, and RF amplifier 1515 for data communication to display device 120 (FIG. 1) or other data processing devices such as, for example, the data processing module 160 and/or remote terminal 170. In certain embodiments, this integration may be in the form of a monolithic integrated circuit, such as an ASIC 1510.

In one embodiment, ASIC 1510 includes at least four terminals, including at least two terminals 1505a, 1505b for the input from analyte sensor 1501 and two terminals 1506c, 1506d for connection to antenna 1520 (shown in FIG. 15 as a loop antenna), which may also serve as a power input for ASIC 1510. ASIC 1510 may also provide additional functions, such as data encryption, data compression, providing or communicating a serial number, time stamp and temperature readings, operating logic, and other functions, in addition to digitizing and transmitting data packets and/or signals corresponding to measured analyte levels.

Antenna 1520 may be inductively coupled, including for example by RF coupling in a manner similar to that used in passive RFID designs as discussed herein. Antenna 1520, when functioning as a passive RF or inductive pickup, may be configured to provide power to ASIC 1510, for example, powering it long enough to take a sensor reading, digitizing it, and communicating the reading through the same antenna 1520, or otherwise for as long or short a period as may be required by the particular application. While in many embodiments, battery-less operation of the sensor assembly will be an important feature, in other embodiments a battery (including one or more cells) could be provided within on body electronics 1500 to supplement the power provided through antenna 1520.

In certain embodiments, the on body electronics may include a power supply such as a battery (for example, encapsulated with the electronic components and/or the sensor with a suitable potting material within the housing). The power supply in such embodiments is configured to provide power to the electronic components in the housing in addition to providing power to the sensor. Furthermore, in certain embodiments, the power supply of the on body electronics is not used or configured to power the data communication between the on body electronics with other devices of the analyte monitoring system.

Figure 16:
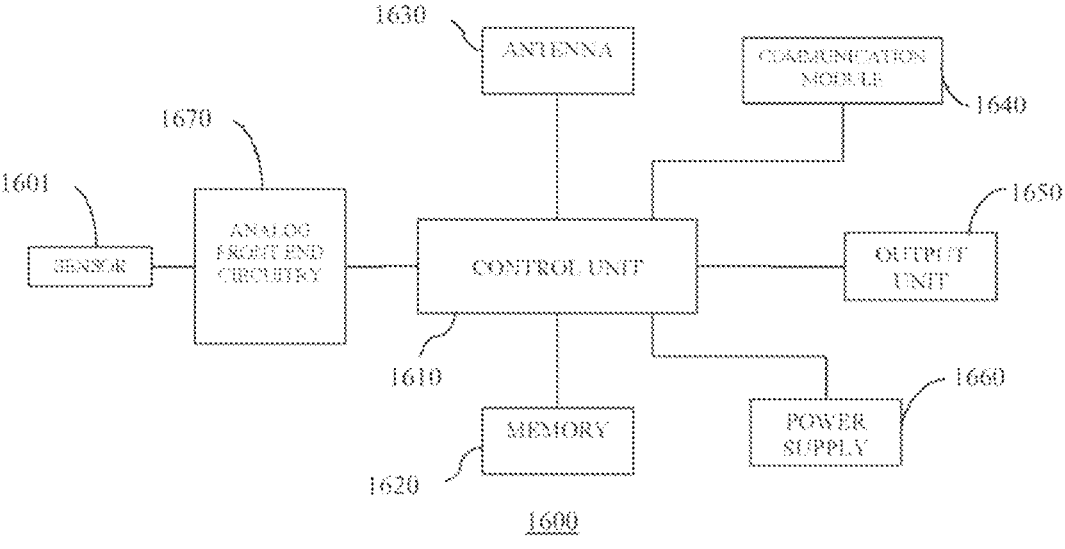
FIG. 16 is a block diagram of on body electronics in analyte monitoring system 100 of FIG. 1 in certain embodiments.

FIG. 16 is a block diagram of the on body electronics in certain embodiments. Referring to FIG. 16, on body electronics 1600 in certain embodiments includes a control unit 1610 (such as, for example but not limited to, one or more microprocessors, and/or ASICs), operatively coupled to analog front end circuitry 1670 to process signals such as raw current signals received from analyte sensor 1601. Also shown in FIG. 16 is memory 1620 operatively coupled to control unit 1610 for storing data and/or software routines for execution by control unit 1610. Memory 1620 in certain embodiment may include electrically erasable programmable read only memory (EEPROM), erasable programmable read only memory (EPROM), random access memory (RAM), read only memory (ROM), flash memory, or one or more combinations thereof.

In certain embodiments, control unit 1610 accesses data or software routines stored in the memory 1620 to update, store or replace stored data or information in the memory 1620, in addition to retrieving one or more stored software routines for execution. Also shown in FIG. 16 is power supply 1660 which, in certain embodiments, provides power to some or all of the components of on body electronics 1600. For example, in certain embodiments, power supply 1660 is configured to provide power to the components of on body electronics 1600 except for communication module 1640. In such embodiments, on body electronics 1600 is configured to operate analyte sensor 1601 to detect and monitor the analyte level at a predetermined or programmed (or programmable) time intervals, and storing, for example, the signals or data corresponding to the detected analyte levels.

In certain embodiments, power supply 1660 in on body electronics 1600 may be toggled between its internal power source (e.g., a battery) and the RF power received from display device 120. For example, in certain embodiments, on body electronics 1600 may include a diode or a switch that is provided in the internal power source connection path in on body electronics 1600 such that, when a predetermined level of RF power is detected by on body electronics 1600, the diode or switch is triggered to disable the internal power source connection (e.g., making an open circuit at the power source connection path), and the components of on body electronics is powered with the received RF power. The open circuit at the power source connection path prevents the internal power source from draining or dissipating as in the case when it is used to power on body electronics 1600.

When the RF power from display device 120 falls below the predetermined level, the diode or switch is triggered to establish the connection between the internal power source and the other components of on body electronics 1600 to power the on body electronics 1600 with the internal power source. In this manner, in certain embodiments, toggling between the internal power source and the RF power from display device 120 may be configured to prolong or extend the useful life of the internal power source.

The stored analyte related data, however, is not transmitted or otherwise communicated to another device such as display device 120 (FIG. 1) until communication module 1640 is separately powered, for example, with the RF power from display device 120 that is positioned within a predetermined distance from on body electronics 1600. In such embodiments, analyte level is sampled based on the predetermined or programmed time intervals as discussed above, and stored in memory 1620. When analyte level information is requested, for example, based on a request or transmit command received from another device such as display device 120 (FIG. 1), using the RF power from the display device, communication module 1640 of on body electronics 1600 initiates data transfer to the display device 120.

Referring back to FIG. 16, an optional output unit 1650 is provided to on body electronics 1600. In certain embodiments, output unit 1650 may include an LED indicator, for example, to alert the user of one or more predetermined conditions associated with the operation of the on body electronics 1600 and/or the determined analyte level. For example, in one aspect, on body electronics 1600 may be programmed or configured to provide a visual indication to notify the user of one or more predetermined operational conditions of on body electronics 1600. The one or more predetermined operational conditions may be configured by the user or the healthcare provider, so that certain conditions are associated with an output indication of on body electronics 1600.

By way of nonlimiting example, the on body electronics 1600 may be programmed to assert a notification using an LED indicator, or other indicator on the on body electronics 1600 when signals (based on one sampled sensor data point, or multiple sensor data points) received from analyte sensor 1601 are indicated to be beyond a programmed acceptable range, potentially indicating a health risk condition such as hyperglycemia or hypoglycemia, or the onset or potential of such conditions. With such prompt or indication, the user may be timely informed of such potential condition, and using display device 120, acquire the glucose level information from the on body electronics 1600 to confirm the presence of such conditions so that timely corrective actions may be taken.

As discussed, output unit 1650 of on body electronics 1600 may optionally include one or more output components such as a speaker, a tactile indicator such as a vibration module, a visual indicator (for example, an LED or OLED indicator), or the like to provide one or more indications associated with its functions such as upon providing the analyte related data to display device 120, alarm conditions associated with its internal components, detection of the RF power received from the display device 120, for example. By way of a non-limiting example, one or more exemplary output indication may include an audible sound (including for example, a short tone, a changing tone, multi-tone, one or more programmed ringtones or one or more combinations thereof), a visual indication such as a blinking light of an LED or OLED indicator, a solid light on the LED or OLED indicator maintained at a predetermined or programmed or programmable time period (for example, about 3 seconds, about 5 seconds, about 7 seconds, about 10 seconds or more), each of which may be preprogrammed in the on body electronics 1600 and/or programmable by the user through the user interface of display device 120 when in communication with on body electronics 1600.

For example, different levels of audible tones may be associated (programmed by the user, or pre-programmed in on body electronics 1600) with different conditions such that when asserted, each outputted tone may be easily recognized by the user as an indication of the particular associated condition. That is, the detected onset of hyperglycemic condition based on the signal from the analyte sensor may be associated with a first predetermined loudness and/or tone, while the detected onset of hypoglycemic condition based on the signal from the analyte sensor 101 may be associated with a second predetermined loudness and/or tone. Alternatively, the programmed or programmable audible alerts may include one or more sequence of audible outputs that are output based on a temporally spaced sequence or a sequence indicating an increase or decrease in the level of loudness (using the same tone, or gradually increasing/decreasing tones).

Furthermore, in aspects of the present disclosure the audible output indication may be asserted in conjunction with the visual output indicator, simultaneously or alternating, as may be customized or programmable in the on body electronics 1600 or pre-programmed.

Referring again to FIG. 16, antenna 1630 and communication module 1640 operatively coupled to the control unit 1610 may be configured to detect and process the RF power when on body electronics 1600 is positioned within predetermined proximity to the display device 120 (FIG. 1) that is providing or radiating the RF power. Further, on body electronics 1600 may provide analyte level information and optionally analyte trend or historical information based on stored analyte level data, to display device 120. In certain aspects, the trend information may include a plurality of analyte level information over a predetermined time period that are stored in the memory 1620 of the on body electronics 1600 and provided to the display device 120 with the real time analyte level information. For example, the trend information may include a series of time spaced analyte level data for the time period since the last transmission of the analyte level information to the display device 120. Alternatively, the trend information may include analyte level data for the prior 30 minutes or one hour that are stored in memory 1620 and retrieved under the control of the control unit 1610 for transmission to the display device 120.

In certain embodiments, on body electronics 1600 is configured to store analyte level data in first and second FIFO buffers that are part of memory 1620. The first FIFO buffer stores 16 (or 10 or 20) of the most recent analyte level data spaced one minute apart. The second FIFO buffer stores the most recent 8 hours (or 10 hours or 3 hours) of analyte level data spaced 10 minutes (or 15 minutes or 20 minutes). The stored analyte level data are transmitted from on body electronics 1600 to display unit 120 in response to a request received from display unit 120. Display unit 120 uses the analyte level data from the first FIFO buffer to estimate glucose rate-of-change and analyte level data from the second FIFO buffer to determine historical plots or trend information.

In certain embodiments, for configurations of the on body electronics that includes a power supply, the on body electronics may be configured to detect an RF control command (ping signal) from the display device 120. More specifically, an On/Off Key (OOK) detector may be provided in the on body electronics which is turned on and powered by the power supply of the on body electronics to detect the RF control command or the ping signal from the display device 120. Additional details of the OOK detector are provided in U.S. Patent Publication No. 2008/0278333, now U.S. Pat. No. 8,456,301, the disclosure of which is incorporated by reference for all purposes. In certain aspects, when the RF control command is detected, on body electronics determines what response packet is necessary, and generates the response packet for transmission back to the display device 120. In this embodiment, the analyte sensor 101 continuously receives power from the power supply or the battery of the on body electronics and operates to monitor the analyte level continuously in use. However, the sampled signal from the analyte sensor 101 may not be provided to the display device 120 until the on body electronics receives the RF power (from the display device 120) to initiate the transmission of the data to the display device 120. In one embodiment, the power supply of the on body electronics may include a rechargeable battery which charges when the on body electronics receives the RF power (from the display device 120, for example).

Referring back to FIG. 1, in certain embodiments, on body electronics 110 and the display device 120 may be configured to communicate using RFID (radio frequency identification) protocols. More particularly, in certain embodiments, the display device 120 is configured to interrogate the on body electronics 110 (associated with an RFID tag) over an RF communication link, and in response to the RF interrogation signal from the display device 120, on body electronics 110 provides an RF response signal including, for example, data associated with the sampled analyte level from the sensor 101. Additional information regarding the operation of RFID communication can be found in U.S. Pat. No. 7,545,272, and in U.S. application Ser. Nos. 12/698,124, 12/699,653, 12/761,387, now U.S. Pat. No. 8,497,777, and U.S. Patent Publication No. 2009/0108992 the disclosure of which are incorporated herein by reference.

For example, in one embodiment, the display device 120 may include a backscatter RFID reader configured to provide an RF field such that when on body electronics 110 is within the transmitted RF field of the RFID reader, on body electronics 110 antenna is tuned and in turn provides a reflected or response signal (for example, a backscatter signal) to the display device 120. The reflected or response signal may include sampled analyte level data from the analyte sensor 101.

In certain embodiments, when display device 120 is positioned in within a predetermined range of the on body electronics 110 and receives the response signal from the on body electronics 110, the display device 120 is configured to output an indication (audible, visual or otherwise) to confirm the analyte level measurement acquisition. That is, during the course of the 5 to 10 days of wearing the on body electronics 110, the user may at any time position the display device 120 within a predetermined distance (for example, about 1-5 inches, or about 1-10 inches, or about 1-12 inches) from on body electronics 110, and after waiting a few seconds of sample acquisition time period, an audible indication is output confirming the receipt of the real time analyte level information. The received analyte information may be output to the display 122 (FIG. 1) of the display device 120 for presentation to the user.

Figure 17:
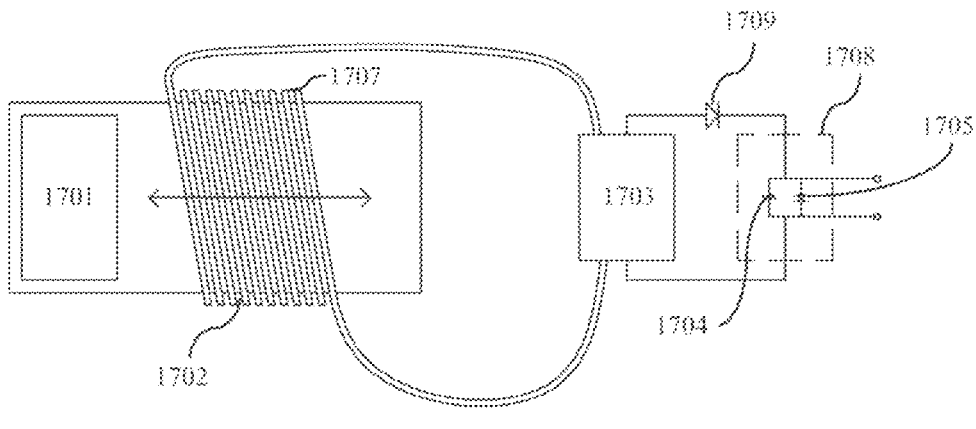
FIG. 17 is a schematic of an on body electronics including an induction generator for use in certain embodiments.

In some embodiments, a small linear induction generator, powered by body movement, may be built into on body electronics 120 of FIG. 1. The induction generator can serve to replace or supplement a battery, or other power source, or RF power configuration of on body electronics 110. As schematically shown in FIG. 17, a generator may include magnet 1701, which is movable relative to conductor 1702. Magnet 1701 may be a strong magnet, such as a rare earth magnet, and conductor 1702 may be a solenoid 1707 comprising a predetermined number of turns or winding of copper wire, within which magnet 1701 is axially slidable back and forth or up and down with respect to the solenoid windings. The movement of the magnet 1701 may be responsive to movement of the on body electronics 110 (FIG. 1) as may occur during normal daily activity of the user with the on body electronics 110 in place during use.

In certain embodiments, dimensions for the induction charging component may not be critical. The solenoid (tube) can be about 5 mm in diameter and 20 mm in length or smaller. Ranges for magnet sizes may range from about 3 mm in diameter and 3 mm in length, to micro sizes depending on the distance available for travel and the amount of current and/or charge desired. Wire diameter can be from about 0.003 mm to about 0.007 mm. To cap the ends, a rubber stopper or snap on lid with a bumper can be used. Alternatively, the cap features can be part of the transmitter casing.

Movement of magnet 1701 relative to conductor 1702 generates electromotive forces (EMF) in conductor 1702 responsive to magnetic flux changes relative to the surface of conductor 1702. The EMF polarity may fluctuate according to the direction in which the magnet 1701 is moving (although a single-polarity embodiment may be achieved where magnet 1701 moves past conductor 1702 in one direction on a circular track). In certain embodiments, such as linear embodiments with back-and-forth magnet movement, in which electricity of changing polarity is generated, rectifier circuit 1703 (which may be a bridge rectifier) may be interposed, and the output from the rectifier 1703 may be stored in storage unit 1708. An additional diode 1709 may be placed in the charging circuit to prevent passive discharge through conductor 1702 when the device is not actively charging. Storage device 1708 for the electrical output of the generator may be a capacitor 1704 and/or diode 1705, or alternately in a mechanical energy storage device such as a flywheel or a spring. Capacitor 1704 may be a supercapacitor, preferably of high quality (high internal resistance, low leakage). Capacitor 1704 (or other storage device) may be used as the sole power source for the on body device, or to supplement battery power. Used as a supplement to a battery, such a generator can extend battery life and/or permit the use of high power consumption functions for the on body electronics 110 (FIG. 1).

In certain embodiments, on body electronics 110 includes an ASIC that includes on chip a RISC (reduced instruction set computing) processor, an EEPROM, and a register (A/D converter operatively coupled to an analyte sensor). EEPROM in certain embodiments includes a portion that has programmed in it one or more characteristics or details associated with a memory management routine. Exemplary characteristics or details include, for example, a source address (e.g., whether it is an array or a single memory location), a destination address, a size/number of bytes to copy to memory, whether the memory location is a loop buffer (e.g., overwriting the older stored values with new values when the end of the buffer is reached).

In certain embodiments, a preset number of specific events may be fined and stored. For example, such events may include, but not limited to (1) RF power on event, (2) RF data read command; (3) RF data log command, (4) 1 minute data ready event (e.g., the A/D conversion of the signal from the analyte sensor is complete and the digitized data is ready for storage), or (5) log data (10 minute analyte data) ready event (e.g., when 10 minutes of analyte data is available for storage). For example, 10 minutes of analyte data is available in certain embodiments when the last A/D conversion for the 10 minute analyte data is complete. In certain embodiments, other events or states may be defined.

In certain embodiments, when the RISC processor detects one of the specific events, the RISC processor executes the programmed memory management routine. During the execution of the memory management routine, the stored characteristics in EEPROM are retrieved. Based on the retrieved characteristics, the memory management routine stores data associated with the detected event. For example, in certain embodiments, when a RF data log command event is detected, the data associated with this event is logged in another section of the EEPROM on ASIC chip in accordance with the retrieved characteristics (e.g., source and destination address for the data associated with this event).

In certain embodiments, the characteristics stored in EEPROM associated with the specific events may be modified. For example, the source and destination address may be changed or modified to point to a different memory device or storage unit of on body electronics 110 (e.g., a separate EEPROM or memory that is not part of the ASIC chip). For example, data logger applications of the monitoring system 100 requires storing an amount of data (e.g., data for about 30 days, about 45 days, about 60 days or more, of 1 minute interval sampled analyte data (or 5 minute interval sampled data, or 10 minute interval sampled data)) in on body electronics 110 much greater than in on demand application where a limited amount of data is stored (e.g., 15 samples of 1 minute interval sampled analyte data, and 6 hours of historical 10 minute interval sampled analyte data). In certain embodiment, the amount of data for storage in data logger application may exceed the capacity of on chip EEPROM. In such cases, a larger capacity, off chip EEPROM may be provided in on body electronics 110 for storing data from the data logger application. To configure on body electronics 110 to store sampled analyte data in the larger capacity, off chip EEPROM, in certain embodiments, the characteristics stored in EEPROM associated with the events are reprogrammed or updated (for example, by updating the source and destination addresses associated with the events) so that data logging or storage is pointed to the larger off chip EEPROM.

In this manner, by updating or reprogramming the portion of on chip EEPROM that stores the event characteristics, location of data storage in on body electronics 110 may be updated or modified depending upon the desired application or use of on body electronics 110. Furthermore, other stored characteristics associated with one or more particular events may be updated or reprogrammed in EEPROM as desired to modify the use or application of on body electronics 110 in analyte monitoring system 100. This is further advantageously achieved without reprogramming or modifying the stored routines for executing the particular events by the RISC processor.

Embodiments of On Body Electronics Initialization/Pairing

Prior to initialization of the on body electronics 110 (FIG. 1) for use, there may be a period of time post manufacturing during which on body electronics 110 may be placed in sleep or idle mode. To initialize on body electronics 110 to transition from the sleep or idle mode, in certain embodiments, a wireless signal may be provided to on body electronics 110 which, upon receipt by on body electronics 110 initiates an initialization routine to turn on body electronics 110 into operational mode for example, by turning on its power source.

Figures 18A, 18B:
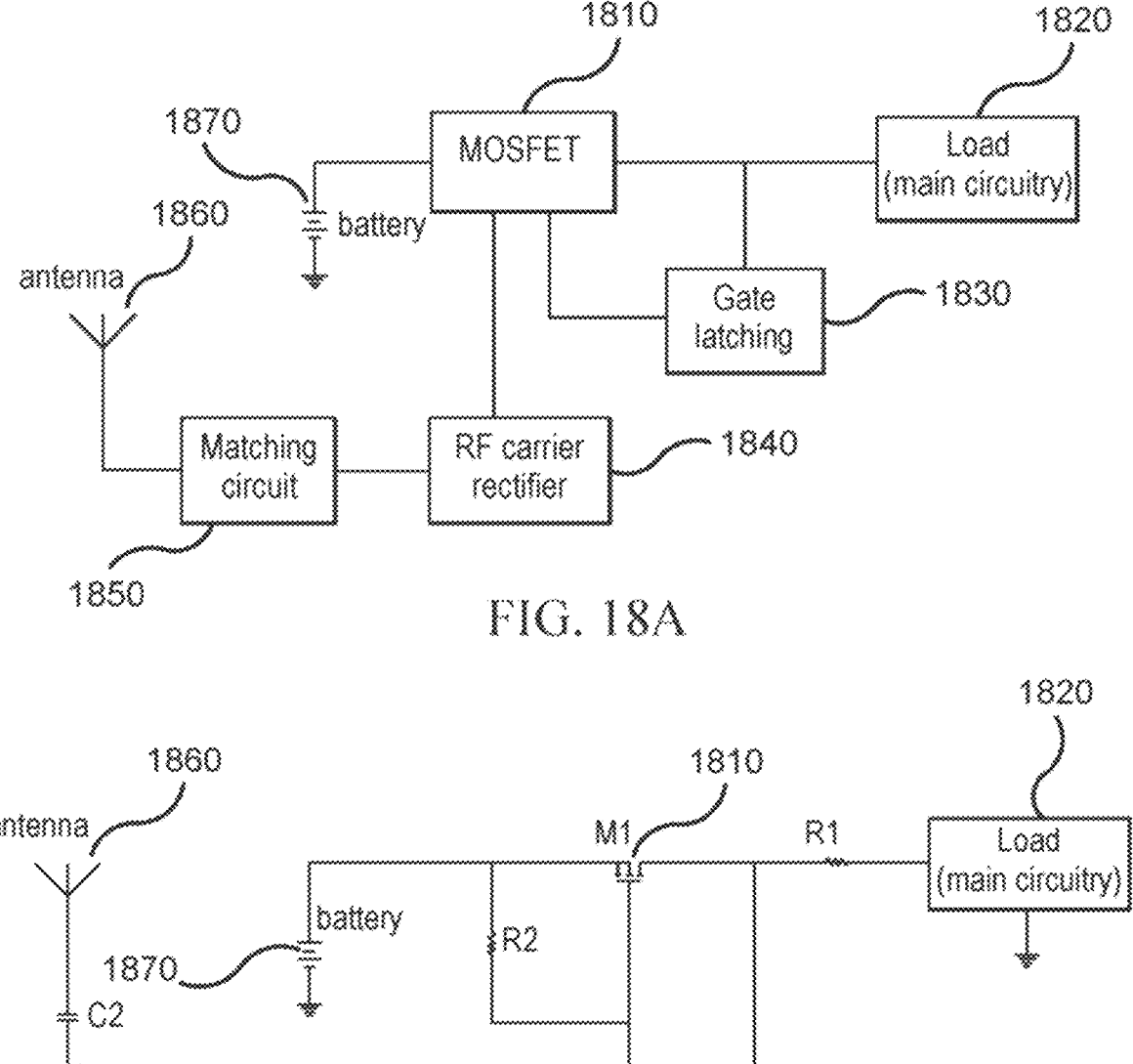
FIG. 18A illustrates a block diagram of the wireless turn on mechanism for analyte monitoring system in certain embodiments.
FIG. 18B illustrates an exemplary circuit schematic of wireless turn on mechanism of FIG. 18A in certain embodiments.

FIGS. 18A-18B illustrates a block diagram and circuit schematic, respectively of wireless turn on mechanism to initialize on body electronics 110 (FIG. 1) in certain embodiments. Referring to FIGS. 16 and 18A, in certain embodiments, communication module 1640 (FIG. 16) includes an electronic switching mechanism for turning on or initializing on body electronics 110 (FIG. 1). More particularly, in certain embodiments, communication module 1640 (FIG. 16) includes a complimentary MOSFET (metal oxide semiconductor field effect transistor) 1810 arranged in combination with the battery or power supply 1870 and gate latching component 1830, which are connected to the load (or the main circuitry of the on body electronics 110 (FIG. 1). In certain embodiments, power supply 1870 may be a separate power supply, or the power supply 1660 (FIG. 16) of on body electronics 110.

Referring back to FIG. 18A, also shown is antenna 1860 for receiving RF signals. Antenna 1860 may be coupled to matching circuit 1850 and RF carrier rectifier 1840 which is coupled to complimentary MOSFET 1810. An exemplary equivalent circuit schematic for the wireless turn on mechanism shown in FIG. 18A is illustrated in FIG. 18B.

Referring to FIGS. 18A-18B, in certain embodiments, when an RF signal is received, for example, from display device 120 (FIG. 1) via the antenna 1860, the received RF signal momentarily biases the gate of the N channel MOSFET M2 through diode D1 which rectifies the received RF signal. Capacitor C1 and inductors L1 and L2 form the matching circuit 1850 (FIG. 18A). Matching circuit 1850 is configured to match the impedance between the antenna 1860 and diode D1. When the N-channel MOSFET M2 is biased, the drain pin of the P-channel MOSFET M1 is biased. When the N-channel MOSFET M2 is biased, the battery or power source 1870 is coupled to the load or the main circuitry 1820 of the on body electronics 110 (FIG. 1). With this connection from the battery 1870 to diode D2, diode D2 biases the N-channel MOSFET M2, and the resulting connection maintains the connection from the battery 1870 to the load 1820 as diode D2 will latch the gate of the N-channel MOSFET M2 even after the received RF signal has dissipated. In this manner, in certain embodiments, communication module 1640 (FIG. 16) of on body electronics 110 (FIG. 1) includes an RF signal based turn on mechanism to initialize on body electronics 110 from the post manufacturing shelf mode. In certain embodiments, display device 120 (FIG. 1) wirelessly transmits the RF turn on signal to on body electronics 110 in response to the user activation or actuation of a command or a signal transmission.

In certain embodiments, the initial positioning and/or maintaining (for a given time period such as about 3-5 seconds, for example) of the display device 120 within a predetermined distance from the on body electronics 110 (after placement on the skin surface) may automatically initiate the transmission of the RF turn on signal to the on body electronics 110 for initialization. In certain embodiments, the RF turn on signal may include one of a plurality of predetermined OOK (On-Off Key) signals.

During post manufacturing shelf mode, on body electronics 110 draws little or no current from the power supply or battery. The internal processing component (such as for example, microprocessor or programmed logic) and the oscillators are in inactive state. RF envelope detector of on body electronics 110 may be configured to be triggered only upon detection of an RF signal from, for example, display device 120 that is positioned within a predetermined distance or data communication range to on body electronics 110 (for initialization) such as within one inch or less, within 3 inches or less, within 5 inches or less, for example.

Alternatively, the on body electronics 110 may be provided or packaged within an RF shielding bag such as a foil pouch. When the RF signal is detected by the envelope detector of on body electronics 110, the output of the envelope detector is configured to control an electronic switch such as a field effect transistor (FET) that, when triggered, applies power or draws power signals from the internal power source such as a battery and the processing component is temporarily latched on.

Figure 19:
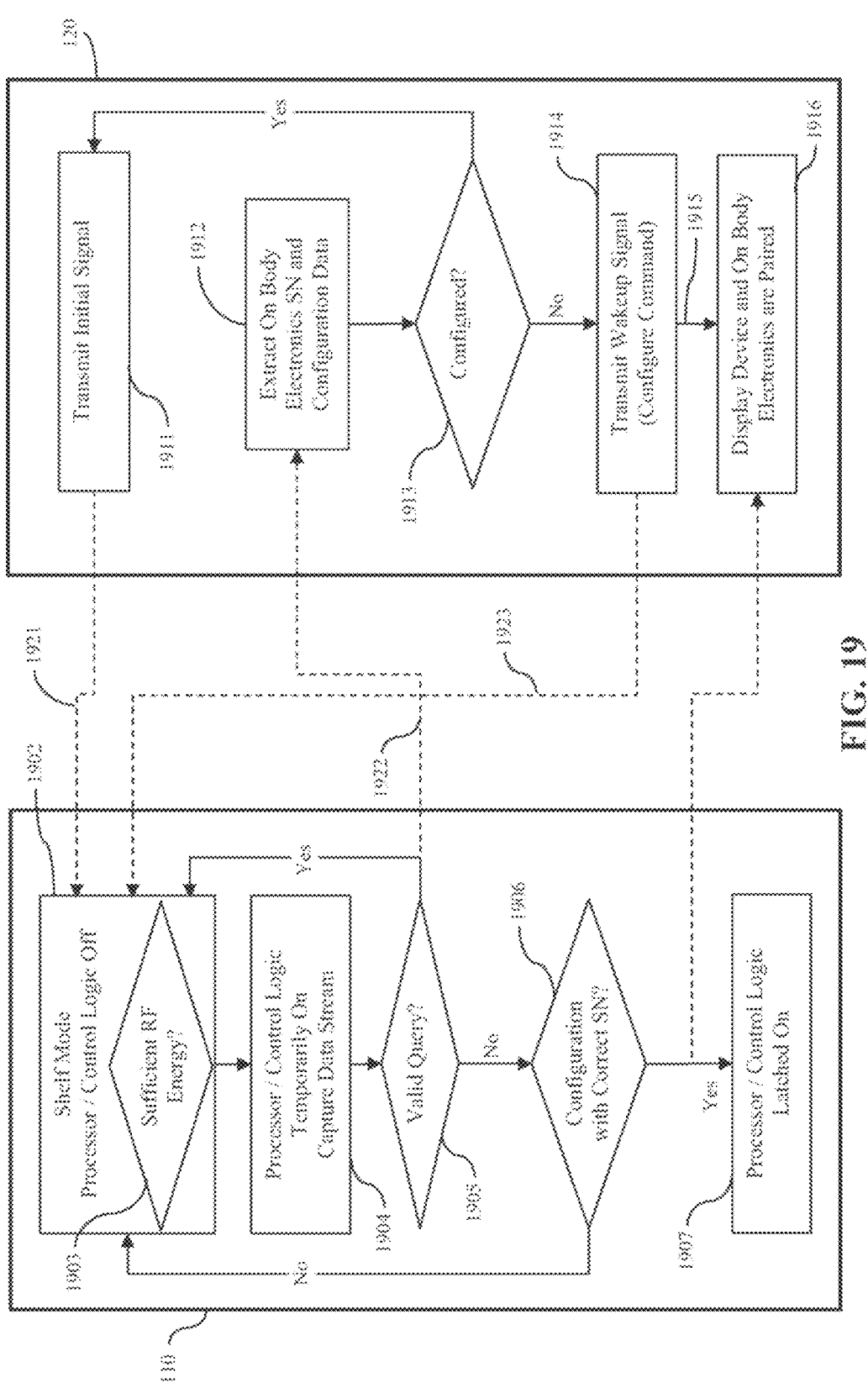
FIG. 19 is a flowchart illustrating data/command exchange between display device and on body electronics for executing wireless turn on procedure in certain embodiments.

Referring now to FIG. 19 which illustrates data and/or commands exchange between on body electronics 110 and display device 120 during the initialization and pairing routine, display device 120 provides and initial signal 1921 to on body electronics 110. When the received initial signal 1921 includes RF energy exceeding a predetermined threshold level 1903, an envelope detector of on body electronics 110 is triggered 1904, one or more oscillators of on body electronics 110 turns on, and control logic or microprocessors of on body electronics 110 is temporarily latched on to retrieve and execute one or more software routines to extract the data stream from the envelope detector 1904. If the data stream from the envelope detector returns a valid query 1905, a reply signal 1922 is transmitted to display device 120. The reply signal 1922 from on body electronics 110 includes an identification code such as on body electronics 110 serial number. Thereafter, the on body electronics 110 returns to shelf mode in an inactive state.

On the other hand, if the data stream from the envelope detector does not return a valid query from display device 120, on body electronics 110 does not transmit a reply signal to display device 120 nor is an on body electronics 110 serial number provided to display device 120. Thereafter, on body electronics 110 returns to shelf mode 1902, and remains in powered down state until it detects a subsequent initial signal 1921 from display device 120.

When display device 120 receives the data packet including identification information or serial number from on body electronics 110, it extracts that information from the data packet 1912. With the extracted on body electronics 110 serial number, display device 120 determines whether on body electronics 110 associated with the received serial number is configured. If on body electronics 110 associated with the received serial number has already been configured, for example, by another display device, display device 120 returns to the beginning of the routine to transmit another initial signal 1911 in an attempt to initialize another on body electronics that has not been configured yet. In this manner, in certain embodiments, display device 120 is configured to pair with an on body electronics that has not already been paired with or configured by another display device.

Referring back to FIG. 19, if on body electronics 110 associated with the extracted serial number has not been configured 1913, display device 120 is configured to transmit a wake up signal 1923 to on body electronics 110 which includes a configure command 1914 so that the devices can be prepared for pairing 1915. In certain embodiments, wake up command from display device 120 includes a serial number of on body electronics 110 so that only the on body electronics with the same serial number included in the wake up command detects and exits the inactive shelf mode and enters the active mode. More specifically, when the wake up command including the serial number is received by on body electronics 110, control logic or one or more processors of on body electronics 110 executes routines 1903, 1904, and 1905 to temporarily exit the shelf mode, when the RF energy received with the wakeup signal (including the configure command) exceeds the threshold level, and determines that it is not a valid query (as that determination was previously made and its serial number transmitted to display device 120). Thereafter, on body electronics 110 determines whether the received serial number (which was received with the wake up command) matches its own stored serial number 1906. If the two serial numbers do not match, routine returns to the beginning where on body electronics 110 is again placed in inactive shelf mode 1902. On the other hand, if on body electronics 110 determines that the received serial number matches its stored serial number 1906, control logic or one or more microprocessors of on body electronics 110 permanently latches on 1907, and oscillators are turned on to activate on body electronics 110. Further, referring back to FIG. 19, when on body electronics 110 determines that the received serial number matches its own serial number 1906, display device 120 and on body electronics 110 are successfully paired 1916.

In this manner, using a wireless signal to turn on and initialize on body electronics 110, the shelf life of on body electronics 110 may be prolonged since very little current is drawn or dissipated from on body electronics 110 power supply during the time period that on body electronics 110 is in inactive, shelf mode prior to operation. In certain embodiments, during the inactive shelf mode, on body electronics 110 has minimal operation, if any, that require extremely low current. The RF envelope detector of on body electronics 110 may operate in two modes—a desensitized mode where it is responsive to received signals of less than about 1 inch, and normal operating mode with normal signal sensitivity such that it is responsive to received signals at a distance of about 3-12 inches.

During the initial pairing between display device 120 and on body electronics 110, in certain embodiments, display device 120 sends its identification information such as, for example, 4 bytes of display device ID which may include its serial number. On body electronics 110 stores the received display device ID in one or more storage unit or memory component and subsequently includes the stored display device ID data in response packets or data provided to the display device 120. In this manner, display device 120 can discriminate detected data packets from on body electronics 110 to determine that the received or detected data packets originated from the paired or correct on body electronics 110. The pairing routine based on the display device ID in certain embodiments avoids potential collision between multiple devices, especially in the cases where on body electronics 110 does not selectively provide the analyte related data to a particular display device, but rather, provide to any display device within range and/or broadcast the data packet to any display device in communication range.

In certain embodiments, the payload size from display device 120 to on body electronics 110 is 12 bytes, which includes 4 bytes of display device ID, 4 bytes of on body device ID, one byte of command data, one byte of spare data space, and two bytes for CRC (cyclic redundancy check) for error detection.

After pairing is complete, when display device 120 queries on body electronics 110 for real time monitored analyte information and/or logged or stored analyte data, in certain embodiments, the responsive data packet transmitted to display device 120 includes a total of 418 bytes that includes 34 bytes of status information, time information and calibration data, 96 bytes of the most recent 16 one-minute glucose data points, and 288 bytes of the most recent 15 minute interval glucose data over the 12 hour period. Depending upon the size or capacity of the memory or storage unit of on body electronics 110, data stored and subsequently provided to the display device 120 may have a different time resolution and/or span a longer or shorter time period. For example, with a larger data buffer, glucose related data provided to the display device 120 may include glucose data over a 24 hour time period at 15 minute sampling intervals, 10 minute sampling intervals, 5 minute sampling intervals, or one minute sampling interval. Further, the determined variation in the monitored analyte level illustrating historical trend of the monitored analyte level may be processed and/or determined by the on body electronics 110, or alternatively or in addition to, the stored data may be provided to the display device 120 which may then determine the trend information of the monitored analyte level based on the received data packets.

The size of the data packets provided to display device 120 from on body electronics 110 may also vary depending upon the communication protocol and/or the underlying data transmission frequency-whether using a 433 MHZ, a 13.56 MHz, or 2.45 GHz in addition to other parameters such as, for example, the availability of a data processing devices such as a microprocessor (e.g., central processing unit CPU) in on body electronics 110, in addition to the ASIC state machine, size of the data buffer and/or memory, and the like.

In certain embodiments, upon successful activation of on body electronics 110 and pairing with display device 120, control unit of display device 120 may be programmed to generate and output one or more visual, audible and/or haptic notifications to output to the user on display 122, or on the user interface of display device 120. In certain embodiments, only one display device can pair with one on body electronics at one time. Alternatively, in certain embodiments, one display device may be configured to pair with multiple on body electronics at the same time.

Once paired, display 122 of display device 120, for example, outputs, under the control of the microprocessor of display device 120, the remaining operational life of the analyte sensor 101 in user. Furthermore, as the end of sensor life approaches, display device may be configured to output notifications to alert the user of the approaching end of sensor life. The schedule for such notification may be programmed or programmable by the user and executed by the microprocessor of display device.

Embodiments of Display Devices

Figure 20:
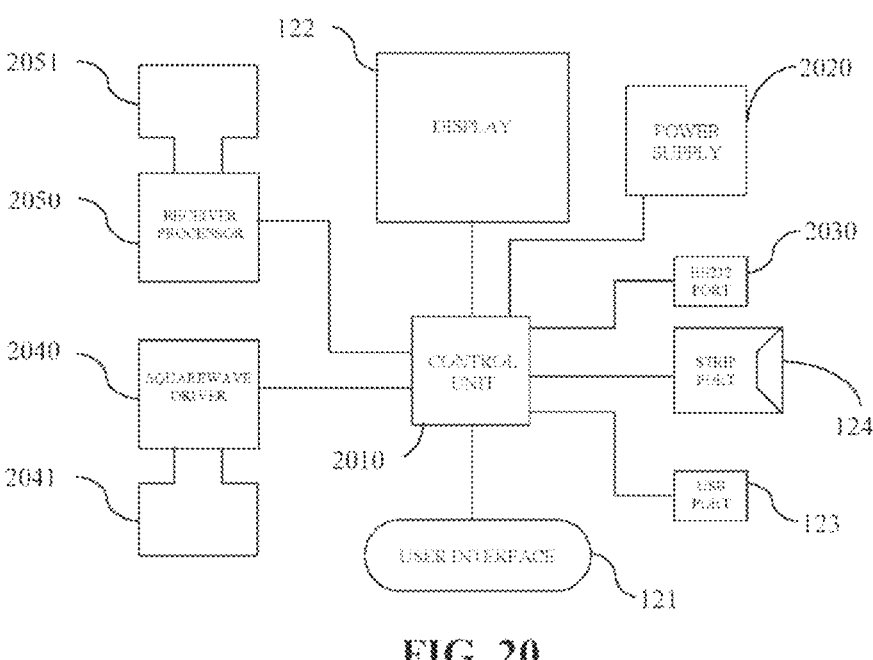
FIG. 20 is a block diagram of the display device of FIG. 1 in certain embodiments.

FIG. 20 is a block diagram of display device 120 as shown in FIG. 1 in certain embodiments. Referring to FIG. 20, display device 120 (FIG. 1) includes control unit 2010, such as one or more microprocessors, operatively coupled to a display 122 and a user interface 121. The display device 120 may also include one or more data communication ports such as USB port (or connector) 123 or RS-232 port 2030 (or any other wired communication ports) for data communication with a data processing module 160 (FIG. 1), remote terminal 170 (FIG. 1), or other devices such as a personal computer, a server, a mobile computing device, a mobile telephone, a pager, or other handheld data processing devices including mobile telephones such as internet connectivity enabled smart phones, with data communication and processing capabilities including data storage and output. Additional information on details of display device and other components of analyte monitoring system are provided in U.S. application Ser. Nos. 12/698,124, 12/699,653, 12/761,387, now U.S. Pat. No. 8,497,777, and U.S. Provisional Applications No. 61/325,155, 61/325,021, the disclosure of each of which are incorporated by reference for all purposes.

Referring back to FIG. 20, display device 120 may include a strip port 124 configured to receive in vitro test strips, the strip port 124 coupled to the control unit 2010, and further, where the control unit 2010 includes programming to process the sample on the in vitro test strip which is received in the strip port 124. Any suitable in vitro test strip may be employed, e.g., test strips that only require a very small amount (e.g., one microliter or less, e.g., about 0.5 microliter or less, e.g., about 0.1 microliter or less), of applied sample to the strip in order to obtain accurate glucose information, e.g. FreeStyle® or Precision® blood glucose test strips and systems from Abbott Diabetes Care Inc. Display devices with integrated in vitro monitors and test strip ports may be configured to conduct in vitro analyte monitoring with no user calibration in vitro test strips (i.e., no human intervention calibration), such as FreeStyle® Lite glucose test strips from Abbott Diabetes Care Inc.

In certain embodiments, an integrated in vitro meter can accept and process a variety of different types of test strips (e.g., those that require user calibration and those that do not), some of which may use different technologies (those that operate using amperometric techniques and those that operate using coulometric techniques), etc. Detailed description of such test strips and devices for conducting in vitro analyte monitoring is provided in U.S. Pat. Nos. 6,377,894, 6,616,819, 7,749,740, 7,418,285; U.S. Published Patent Publication Nos. 2004/0118704, 2006/0091006, 2008/0066305, now U.S. Pat. No. 7,895,740, 2008/0267823, 2010/0094110, now U.S. Pat. No. 8,688,188, 2010/0094111, now U.S. Pat. No. 8,346,337, and 2010/0094112, now U.S. Pat. No. 8,465,425, and U.S. application Ser. No. 12/695, 947, now U.S. Pat. No. 8,828,330, the disclosure of each of which are incorporated herein by reference for all purposes.

Glucose information obtained by the in vitro glucose testing device may be used for a variety of purposes, computations, etc. For example, the information may be used to calibrate analyte sensor 101 (FIG. 1) if the sensor requires in vivo calibration, confirm results of analyte sensor 101 to increase the confidence in the results from sensor 101 indicating the monitored analyte level (e.g., in instances in which information obtained by sensor 101 is employed in therapy related decisions), etc. In certain embodiments, analyte sensors do not require calibration by human intervention during its usage life. However, in certain embodiments, a system may be programmed to self-detect problems and take action, e.g., shut off and/or notify a user. For example, an analyte monitoring system may be configured to detect system malfunction, or potential degradation of sensor stability or potential adverse condition associated with the operation of the analyte sensor, the system may notify the user, using display device 120 (FIG. 1) for example, to perform analyte sensor calibration or compare the results received from the analyte sensor corresponding to the monitored analyte level, to a reference value (such as a result from an in vitro blood glucose measurement).

In certain embodiments, when the potential adverse condition associated with the operation of the sensor, and/or potential sensor stability degradation condition is detected, the system may be configured to shut down (automatically without notification to the user, or after notifying the user) or disable the output or display of the monitored analyte level information received from the on body electronics assembly. In certain embodiments, the analyte monitoring system may be shut down or disabled temporarily to provide an opportunity to the user to correct any detected adverse condition or sensor instability. In certain other embodiments, the analyte monitoring system may be permanently disabled when the adverse sensor operation condition or sensor instability is detected.

Referring still to FIG. 20, power supply 2020, such as one or more batteries, rechargeable or single use disposable, is also provided and operatively coupled to control unit 2010, and configured to provide the necessary power to display device 120 (FIG. 1) for operation. In addition, display device 120 may include an antenna 2051 such as a 433 MHz (or other equivalent) loop antenna, 13.56 MHz antenna, or a 2.45 GHz antenna, coupled to a receiver processor 2050 (which may include a 433 MHz, 13.56 MHz, or 2.45 GHz transceiver chip, for example) for wireless communication with the on body electronics 110 (FIG. 1). Additionally, an inductive loop antenna 2041 is provided and coupled to a squarewave driver 2040 which is operatively coupled to control unit 2010.

In certain embodiments, antenna configurations including loop antenna configurations are provided for display device 120 for data communication at Ultra High Frequency (UHF) frequency bands, providing a real time analyte data acquisition system that includes display device 120 which is configured to generate a strong near electromagnetic field to provide power to on body electronics 110 to receive sampled and/or processed analyte related data from on body electronics 110. Such configuration also provides a weak far electromagnetic field such that the strength of the generated magnetic field at a far distance, such as about 3 meters away or 4 meters away or more from on body electronics 110 maintains the data communication range between on body electronics 110 and display device 120. In certain embodiments, display device 120 may be configured for RF transmission at any frequency.

Figure 21B:
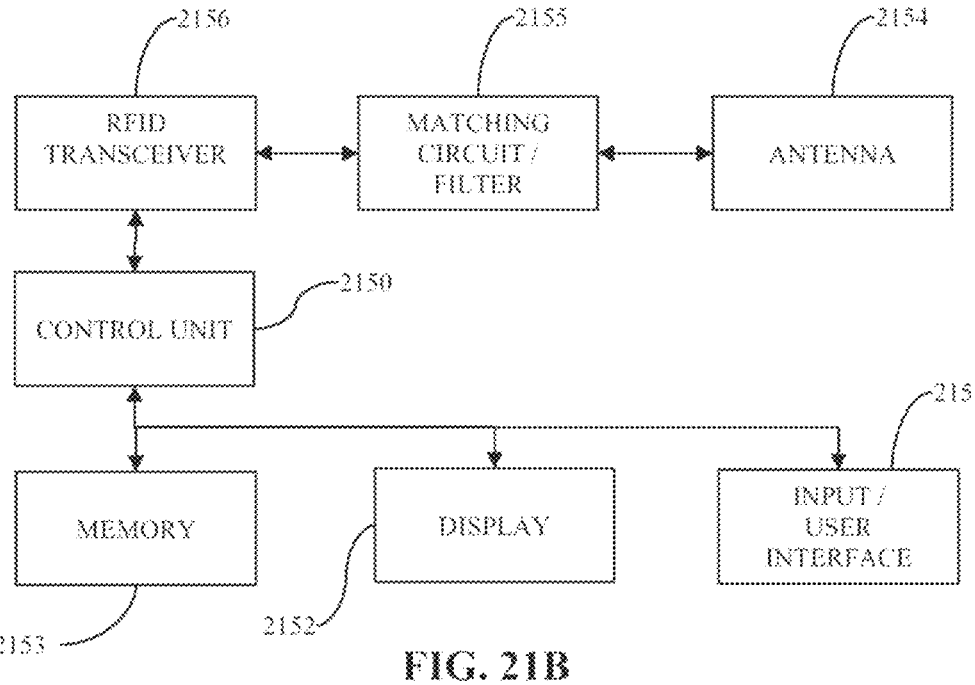
FIG. 21B is a schematic of the display device of FIG. 1 in certain embodiments.
Figure 21A:
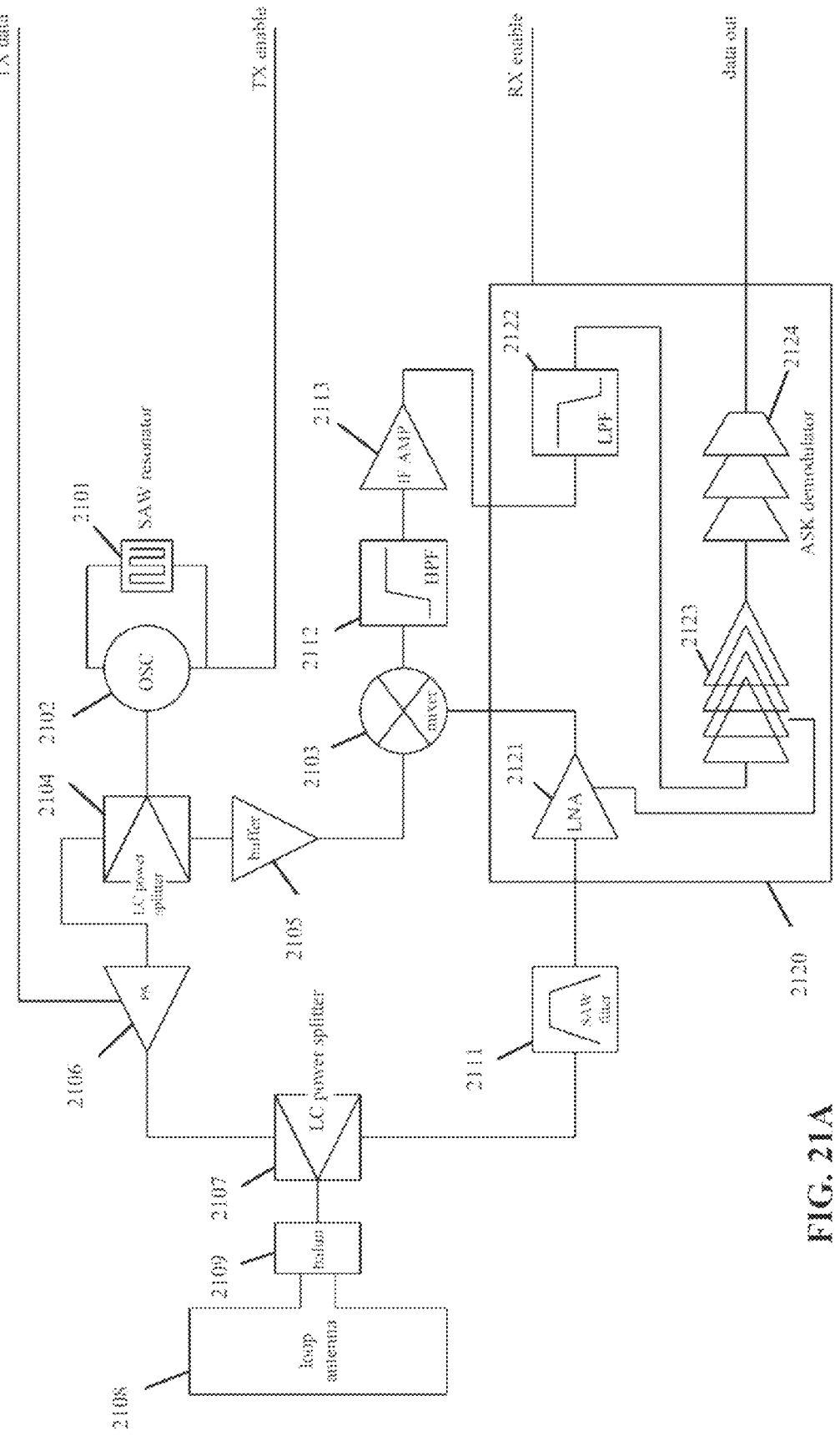
FIG. 21A is a schematic of the display device of FIG. 1 in certain embodiments.

FIG. 21A is a schematic of the display device for use in the analyte monitoring systems of FIG. 1 in certain embodiments. Referring to the figure, display device 120 (FIG. 1) configured to provide RF power to the on body electronics 110 (FIG. 1) in accordance with one aspect of the present disclosure, includes a surface acoustic wave (SAW) resonator 2101 which may include a resonator that generates the RF signal operating in conjunction with an oscillator (OSC) 2102. The oscillator 2102 is the active RF transistor component, and in conjunction with the SAW resonator 2101, is configured to send out control commands (the ping signals), transmit the RF power to receive the backscatter signal from the on body electronics 110, and generate local oscillation signal to the mixer 2103, as described in further detail below.

More specifically, in certain embodiments, in operation, the transmit data (TX data) as shown is the control signal generated by the control unit of the display device 120 (FIG. 1), and an RF control command from the power amplifier (PA) 2106, is configured for transmission to on body electronics 110. SAW resonator 2101 in certain embodiments is configured to provide the carrier signal for the control commands (ping signals). The control signal from display device 120 (FIG. 1) in certain embodiments includes data packets that are to be transmitted to on body electronics 110 to ping or prompt on body electronics 110, and to request for a response packet back display device 120.

In one embodiment, before the control signal is sent, a turn on signal from control unit of display device 120 is received at the TX enable line (as shown in FIG. 21A) and provided to oscillator 2102. After the control signal from the control unit is provided to oscillator 2102 and SAW resonator 2101, the carrier signal which is used to carry the control signal is maintained. The same carrier signal in one embodiment may be used to receive the response data packet from on body electronics 110 (FIG. 1).

When the RF control signal is provided to on body electronics 110 using the loop antenna and over the carrier signal, the RF power is provided at the same time (radiation energy) where the RF power is generated by oscillator 2102 in conjunction with SAW resonator 2101. In certain embodiments, because the carrier signal is maintained during transmit/receive time periods between display device 120 and on body electronics 110, the RF power is provided during the ping (or control signal) request transmission of the RF control signal, and also during the time period when the backscatter response is received from on body electronics 110. In certain embodiments, loop antenna 2108 of display device 120 uses the same carrier signal to transmit the RF power and the RF control signal to on body electronics 110, while in other embodiments different carrier signals are used.

Referring back to FIG. 21A, further shown is LC power splitter 2104 which is configured in certain embodiments to split the power two ways—to buffer 2105 and to power amplifier (PA) 2106. Buffer 2105 in certain embodiments is configured to boost the RF signal received from LC power splitter 2104. Output of power amplifier 2106 is a control command that is provided to a second LC power splitter 2107 which splits the antenna signal (from the loop antenna into transmit signal (the control signal) and the receive signal (backscatter signal from on body electronics 110)). That is, in one embodiment, second LC power splitter 2107 may be configured to manage the transmit/receive signals using one loop antenna 2108. Referring again to FIG. 21A, in certain embodiments, a balun 2109 provided between the loop antenna 2108 and the second LC power splitter 2107 is used in one embodiment to match the balanced signal from the loop antenna 2108 to the unbalanced signal from the power splitter 2107 (as most circuit components are unbalanced relative to ground terminal). Balun 2109 includes, in certain embodiments, an electrical transformer that converts electrical signals that are balanced about ground (differential) to signals that are unbalanced (single-ended), and vice versa, using electromagnetic coupling for operation.

Referring still to FIG. 21A, loop antenna 2108 transmits the RF control signal (the ping signal) and in response, receives a response packet from on body electronics 110. In one aspect, the received response packet by the loop antenna is passed through the balun 2109, and via power splitter 2107 to SAW filter 2111. SAW filter 2111 in certain embodiments includes a bandpass filter configured to remove noise or interference components in the received response packet, for example. The output of SAW filter 2111 is passed through ASK receiver 2120. In one aspect, ASK receiver 2120 includes low noise amplifier (LNA) 2121 whose output is sent to mixer 2103 which mixes the low noise amplified signal output from LNA 2121 with the RF carrier signal from buffer 2105.

The output of mixer 2103 is passed to high pass filter (HPF) 2112 that filters out the DC component and low frequency components of the signal, and then the output of HPF 2112 is sent to the intermediate frequency amplifier (IF amplifier) 2113 which is configured to amplify the received signal. The amplified output signal from IF amplifier 2113 is provided to the low pass filter (LPF) 2122 of ASK receiver 2120, and the output low pass filtered signal from LPF 2122 is provided to another intermediate frequency amplifier 2123 of ASK receiver 2120 which is configured to amplify the low pass filtered signal output from the LPF 2122. As shown in FIG. 21A, IF amplifier 2123 of ASK receiver 2120 is provided between LPF 2122 and ASK demodulator 2124.

Referring yet still to FIG. 21A, the gain controller signal from IF amplifier 2123 of ASK receiver 2120 controls the LNA 2121 that receives the filtered backscatter signal. The gain controller signal in one embodiment switches between high gain and low gain state of LNA 2121. For example, if IF amplifier 2123 has high gain, then the gain controller signal to LNA 2121 switches the LNA 2121 to low gain operation, and vice versa. As discussed above, the output of the IF amplifier 2123 of ASK receiver 2120 is provided to ASK demodulator 2124 of ASK receiver 2120 which is configured to demodulate (or recover the data) the output signal from IF amplifier 2123.

That is, as shown in FIG. 21A, the RX enable line to ASK receiver 2120 is configured to turn on after the TX enable line where the turn on signal from the control unit is received in display device 120 such that with the receive enable signal from the control unit, the data out line (i.e., the output of ASK demodulator 2124) of ASK receiver 2120 provides the data or signal associated with the monitored glucose level based on the raw current signals from analyte sensor 101 (FIG. 1).

Referring again to FIG. 21A, in certain embodiments, an RF transmitter chip or an ASK transmitter may be included in display device 120 (FIG. 1) to replace the SAW resonator 2101, oscillator 2102, mixer 2103, LC power splitter 2104, buffer 2105, power amplifier 2106, high pass filter (HPF) 2112, and IF amplifier 2113 shown in FIG. 21A. More specifically, in this embodiment, the RF transmitter chip may be coupled to a crystal which provides the frequency reference base for generating the RF carrier signal to receive the backscatter signal from on body electronics 110, and also to send the control commands (ping signals) to on body electronics 110.

In the embodiment discussed above, the RF transmitter chip or unit may be coupled to the LC power splitter, a balun and the loop antenna similar to the LC power splitter 2107, balun 2109, and loop antenna 2108 shown in FIG. 21A, in addition to a SAW filter and ASK receiver similar to the SAW filter 2111 and ASK receiver 2120 shown in FIG. 21A. However, compared to the configuration shown in FIG. 21A, in alternate embodiments, another crystal may be coupled to the ASK receiver to provide the frequency reference base for receiving the backscatter signal from on body electronics 110.

FIG. 21B illustrates a block diagram of display device 120 in the analyte monitoring system 100 of FIG. 1 in certain embodiments. Referring to FIG. 21B, and in conjunction with FIG. 1, display device 120 includes control unit 2150 operatively coupled to the components as shown in the Figure including input/user interface 2151, display 2152, memory 2153, and RFID transceiver 2156. As further shown in FIG. 21B, RFID transceiver 2156 in certain embodiments is operatively coupled to matching circuit/filter 2155 that is coupled to antenna 2154. Matching circuit/filter 2155 in certain embodiments is configured to tune and/or match the signals between the on body electronics 110 (FIG. 1) and display device 120, sent and received via antenna 2154. Antenna 2154, in certain embodiments includes a 13.56 MHz RFID antenna where RFID transceiver 2156 is configured to operate in the 13.56 MHz frequency. In certain embodiments, RFID transceiver 2156 may include a user programmable modulation depth in write mode where data or command is sent, whereas single subcarrier, frequency shift keying (FSK) and phase shift keying (PSK) modulations are recognized in the read mode where data is received from on body electronics 110, for example. Moreover, a logarithmic amplifier may be used for single subcarrier detection for data recovery from on body electronics 110.

Referring again to FIG. 21B, control unit 2150 in certain embodiments include one or more microcontrollers or processors, ASIC with programmed logic for execution by one or more state machines for controlling and executing the operation of the reader (FIG. 1). Memory 2153 in certain embodiments includes volatile memory and/or non-volatile memory for data storage.

In certain embodiments, data communication between on body electronics 110 and display device 120 may be achieved at the 2.45 GHz ISM band. In certain embodiments, display device 120 (FIG. 1) is configured to listen for a clear channel on 2.45 GHz radio frequency band. When a clear channel is detected and selected, a clear channel identifier is sent to a control unit of an on body electronics 110 (FIG. 1). After the clear channel identifier is received, the data packets are provided to the receiver unit. Thus, the power drain of the "listen before talk" process required of operation in the 2.45 GHz ISM band comes off of the larger batteries in display device 120, conserving power in the on body electronics 110.

Figure 23:
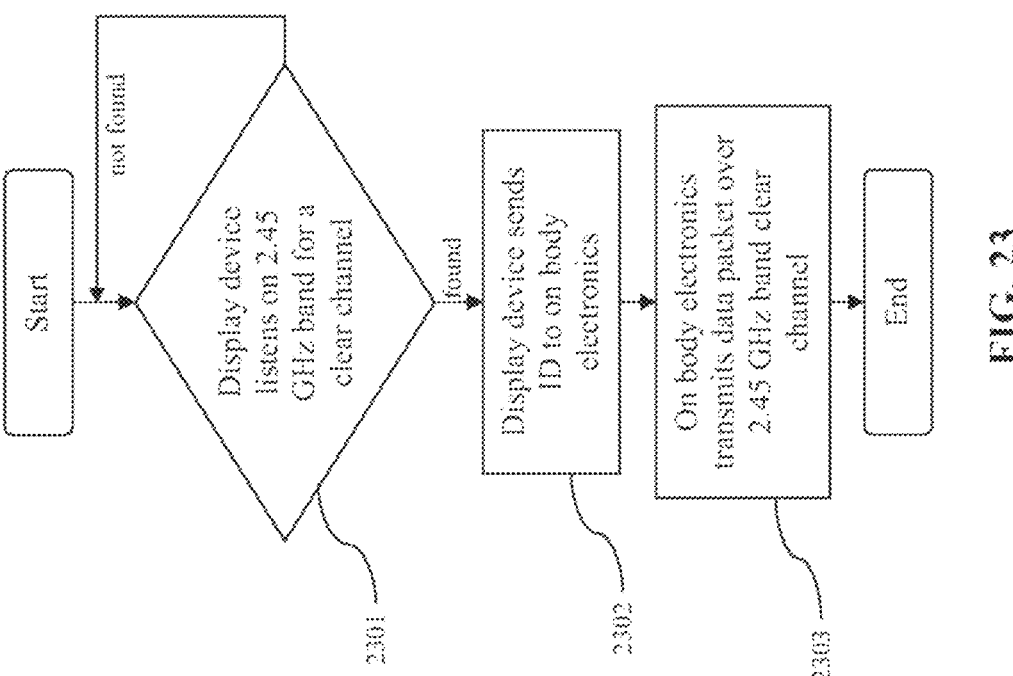
FIGS. 22 and 23 are diagram and flowchart, respectively, illustrating a process for implementing a wireless communication in the system of FIG. 1 in certain embodiments.
Figure 22:
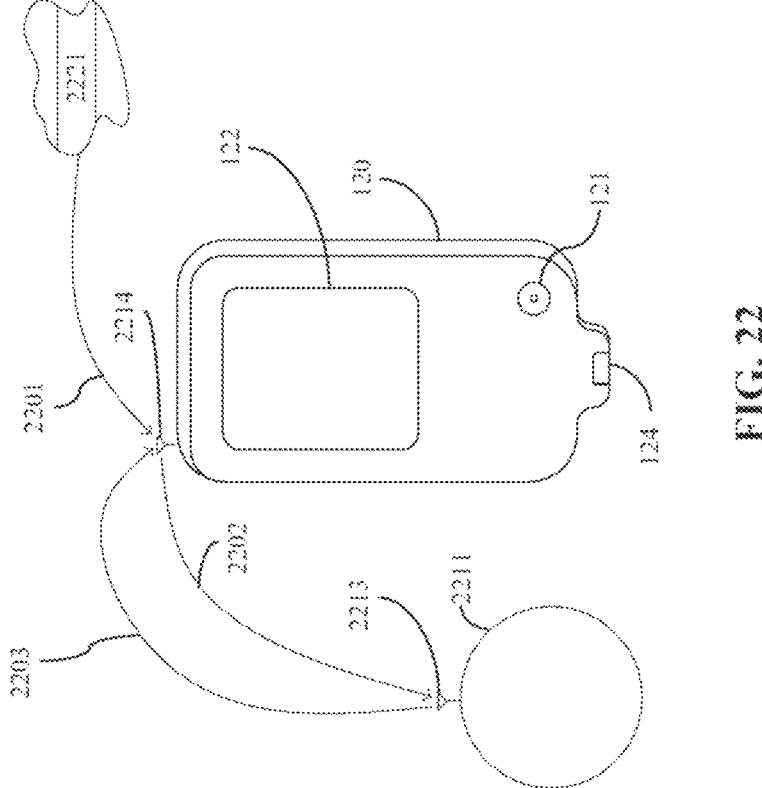

An exemplary process for using this communications system is illustrated in the schematic diagram of FIG. 22 in conjunction with the routine shown in FIG. 23. When the user desires or requires an analyte reading, such as a current glucose level, and/or wants to collect logged analyte data, display device 120 can be used to find a clear channel (2201) on the 2.45 GHz band (2221) (step 2301), and then, to separately send an OOK (or other suitably modulated) message to the on body electronics 2211, communicating a clear frequency identifier (2202) (step 2302). On body electronics 2211 then responds with a high-baud rate stream of data packets, transmitted over the clear channel (2203) (step 2303). With this procedure, on body electronics 2211 does not have to perform the "listen to talk" routine because this routine has been conducted by the display device 120.

Referring again to FIGS. 22-23, in certain embodiments, display device 120 may include an RF transceiver, with an RF transmitter on the 2.45 GHz band coupled to antenna 2214 (schematically shown as external; however, the antenna may be mounted internally to the display device 120). It also may have a digitally modulated RF signaling function, which can be an OOK signaling function, either in the 2.45 GHz band or some other band (in which case there could be a second antenna on the receiving unit (not shown)). The on body electronics 2211 in certain embodiments includes a data processing unit in which the power supply may be a small battery, and the RF transmitter/receiver can be a low power 2.45 GHZ transceiver, e.g., a Texas Instruments® CC2510 integrated circuit, which, in addition to the 2.45 GHz radio, also provides a microprocessor (CPU), memory, analog-to-digital conversion (ADC), and signal processing functions.

In certain embodiments, the RF communication component of the on body device 2211 may be coupled to antenna 2213 (schematically shown as external; however, the antenna may be mounted internally to the on body device 2211). The on body electronics 2211 may also have a receiver capable of receiving a digitally modulated signal containing a clear channel identifier. In this regard, the RF transceiver may be configured as an ultra-low power OOK receiver that requires extremely low power to listen, but only has a limited listening range. The listening range is sufficient, however, to be operable when the receiver unit 120 is in proximity to the on body electronics 2211, for example when one unit is placed next to the other within a predetermined distance of for example, less than about 10 inches, less than about 5 inches, less than about 3 inches, or less than about one inch, or any other suitable distance.

In certain embodiments, data packets received from on body electronics and received in response to a request from display device, for example, include one or more of a current glucose level from the analyte sensor, a current estimated rate of glycemic change, and a glucose trend history based on automatic readings acquired and stored in memory of on skin electronics. For example, current glucose level may be output on display 122 of display device 120 as a numerical value, the current estimated rage of glycemic change may be output on display 122 as a directional arrow 131 (FIG. 1), and glucose trend history based on stored monitored values may be output on display 122 as a graphical trace 138 (FIG. 1). In certain embodiments, microprocessor of display device 120 may be programmed to output more or less information on display 122, and further, the type and amount of information output on display 122 may be programmed or programmable by the user.

In certain embodiments, display device 120 is programmed to maintain a time period between each consecutive of analyte data request from on body electronics 110. For example, in certain embodiments, display device 120 is configured such that after an initial analyte data request has been sent to on body electronics 110, and the monitored analyte level information received from on body electronics 110, display device 120 disallows a subsequent analyte data request to be sent to on body electronics 110 until a predetermined time period has elapsed measured from the transmission of the initial analyte data request. For example, when display device 120 is operated to send to on body electronics 110 a request for analyte related data, an internal clock or timer of the display device 120 starts or activates the internal clock or timer programmed with a predetermined time period to count down. Display device 120 in certain embodiments include programming to disable or prevent sending the second, subsequent request for analyte data from on body electronics 110 until after the predetermined time period has elapsed.

In certain embodiments, the predetermined time period includes about 120 seconds, about 90 seconds, about 60 seconds, or about 30 seconds or less. The predetermined time period in certain embodiments is determined by the time period for performing analog to digital conversion by on body electronics 110 to convert the sampled signal from monitoring the analyte level to a corresponding digital signal for transmission and/or the sampling period of analyte sensor 101, monitoring analyte level every minute, or every 5 minutes, or every 10 minutes or other suitable time interval. The time interval in certain embodiments may be pre-programmed as software logic in on body electronics 110, or alternatively, is programmable and can be modified during in vivo sensor use.

In certain embodiments, display device 120 requires a minimum time period to elapse between each successive analyte data request from on body electronics 110 to avoid corrupting the data in on body electronics 110. For example, when the analog to digital (A/D) conversion routine is being executed by on body electronics 110 (for example, during the initial 30 second window for each 1 minute sampling period associated with analyte sensor 101), display device 120 transmits an analyte data request (for example, the RF power level from display device 120 may disrupt the A/D conversion routine) or otherwise corrupt the data resulting from the A/D conversion routine being executed by on body electronics 110. Accordingly, in certain embodiments, display device 120 is programmed to disallow sending a request for analyte data from on body electronics (110) (for example, performing a read function by display device 120) during an (A/D) conversion cycle in on body electronics 110. Accordingly, the time interval between data requests from display device 120 ensures that the A/D conversion routine is complete in on body electronics 110 when display device 120 sends the data request to on body electronics 110.

In certain embodiments, display device 120 may be programmed or programmable to discard or identify received data from on body electronics 110 that is corrupt or otherwise includes error. For example, in certain embodiments, a minimum time period between subsequent analyte data request is not enforced or programmed in display device 120. However, display device 120 includes software routines that can identify data that is corrupt or not based on examining the data packet. For example, each data packet received from on body electronics 110 includes a single bit or a byte or other suitable portion of the data packet that provides an indication of the data status. In the case of a single bit as the data status identifier in the data packet from on body electronics 110, in certain embodiments, a value of 1 indicates that the data is not corrupt. In such embodiments, on body electronics 110 is configured to reset this bit in the data packet to 0 at the end of each sampling period (for example, after each minute), and change the value to 1 when the A/D conversion routine is completed during the sampling period without error.

Embodiments of Data Processing Routines

In certain embodiments, data from on body electronics 110 (FIG. 1) provided to display device 120 may include raw monitored analyte level data, measured or monitored temperature data, stored past monitored analyte level data, analyte level trend data (such as a series of consecutive or near consecutive data points corresponding to the monitored analyte level) that was stored or buffered in the on body electronics for a predetermined time period, since the activation of the on body electronics, or since the time period when the last data packet or signals were provided to the display device, or any one or more combinations of the above. For example, the historical information constructed by a series of consecutive and/or near consecutive data points corresponding to the monitored analyte level may indicate the variation in the monitored analyte level over the particular time period based on signals received from the analyte sensor and stored in the on body electronics.

In certain embodiments, display device 120 is configured to determine and adjust for deviation or drift of time base in on body electronics 110 such that the analyte sensor 101 life is monitored and accurately terminated upon expiration of its useful time period. In certain embodiments, on body electronics 110 include limited storage capacity in its memory (for example, storing the past 24 hours, or 12 hours, or 8 hours, or 5 hours of logged data, overwriting the older data). In such cases, if the sensor is not disabled when it reaches the end of its useful life time period (for example, 10 days, or seven days, or five days, or three days), the logged data will be overwritten by new data generated from the expired sensor.

Figure 24:
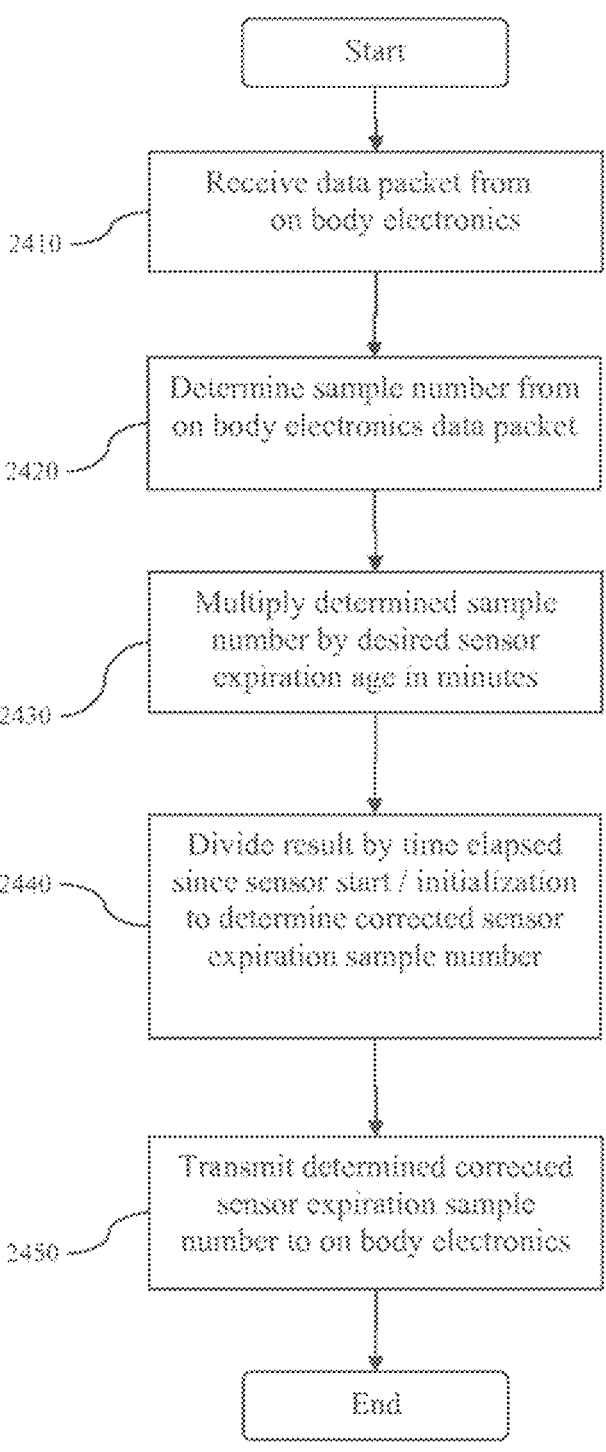
FIG. 24 is a flowchart illustrating a routine for determining the sensor expiration information by display device 120 for communication to on body electronics in certain embodiments.

More specifically, FIG. 24 is a flowchart illustrating a routine for determining the sensor expiration information by display device 120 for communication to on body electronics in certain embodiments. Display device 120 is configured to track time information accurately based on its internal clock(s). In certain embodiments, on body electronics 110 is programmed with total sample number information that corresponds to the sensor life duration. For example, if the sensor is a 10 day sensor, and it is configured to sample analyte level in ISF once every minute, the total sample number for the 10 day analyte sensor is 14,400 samples (60 mins/hr*24 hrs/day*10 days). When display device 120 receives a data packet with the sample number information from on body electronics 110, display device 120 in certain embodiments includes software routines that are executed to determine, based on the sample number received from the on body electronics 110 and time information from the internal clock or crystal of the display device 120, the correct total sample number for the sensor 101.

For example, referring to FIG. 24, when display device 120 receives a data packet from on body electronics 110 (2410), microprocessor or controller of display device 120 extracts sample number information associated with the received data packet in addition to other data such as current analyte level data, current temperature data, stored historical monitored analyte data, for example (2420). Display device 120 then retrieves the analyte sensor expiration information (for example, in time based unit such as 14,400 minutes for 10 day sensors) and multiplies the retrieved sensor expiration time information with the received sample number (2430). The resulting value from the multiplication is then divided by the time elapsed since sensor initialization (measured, for example, in time based units) (2440), resulting in the corrected expiration sample number for the analyte sensor.

When the display device 120 is in subsequent communication with on body electronics 110, the determined expiration sample number is transmitted to on body electronics 110 (2450). On body electronics 110, in turn, stores the received expiration sample number, and compares the sample number for each sampled analyte from the analyte sensor, and when the sample number corresponding to the sample analyte level from the analyte sensor matches or exceeds the received expiration sample number, on body electronics 110 is programmed to no longer log data. In this manner, in certain embodiments, display device 120 is configured to determine correction to the sensor expiration or end of life time period for the sensor, and communicate the adjustment or correction to on body electronics 110 so that data logged from unexpired analyte sensor is not overwritten by data from sensor whose useful life has ended.

In the manner described above, a first order model is provided to correct for sensor expiration time period deviation. In certain embodiments, second or higher order models or polynomials may be used to improve accuracy of the sensor life expiration determination. For example, the first order model described in conjunction with FIG. 24 assumes that the on body electronics time reference remains substantially constant during the sensor life. In cases where the time reference does not remain constant during the sensor life, a weighing function may be introduced such that, different weighing function is applied at the initial stage of sensor life compared to the later stage of the sensor life, such that the average value over the course of the sensor life more accurately represents the true sensor expiration time period.

Furthermore, in certain embodiment, the time base of the on body electronics may accumulate error continuously from the start of the sensor life until the last sampled data logged at the end of the sensor life. In certain embodiments, display device 120 may be configured to determine a precise time-sample number pair each time data packet is received from on body electronics 110. To address the accumulation of error in on body electronics time base, display device 120 in certain embodiments, for each data packet received from on body electronics 110, display device 120 determines a new time-sample number pair. By keeping the previous time-sample pair, the display device 120 may perform piece wise interpolation to determine the actual time of each sample logged and received from on body electronics 110.

For example, at sample time t=980 (e.g., elapsed time since sensor insertion and initialization), with sample number of 1,000, and at sample time t=2020 corresponding to sample number 2000, piece wise interpolation yields an increment in time t of 104 for each increment of 100 in sample number as shown below:

TABLE 1

| Sample Number | Time |
|---|---|
| 1000 | 980 |
| 1100 | 1084 |
| 1200 | 1188 |
| 1300 | 1292 |
| 1400 | 1396 |
| 1500 | 1500 |
| 1600 | 1604 |
| 1700 | 1708 |
| 1800 | 1812 |
| 1900 | 1916 |
| 2000 | 2020 |

As can be seen in conjunction with Table 1 above, in certain embodiments, using interpolation based on the two sample number-time pairs, actual sample time for each sample can be determined, and any error accumulated or introduced by on body electronics 110 may be corrected.

Figures 25, 26:
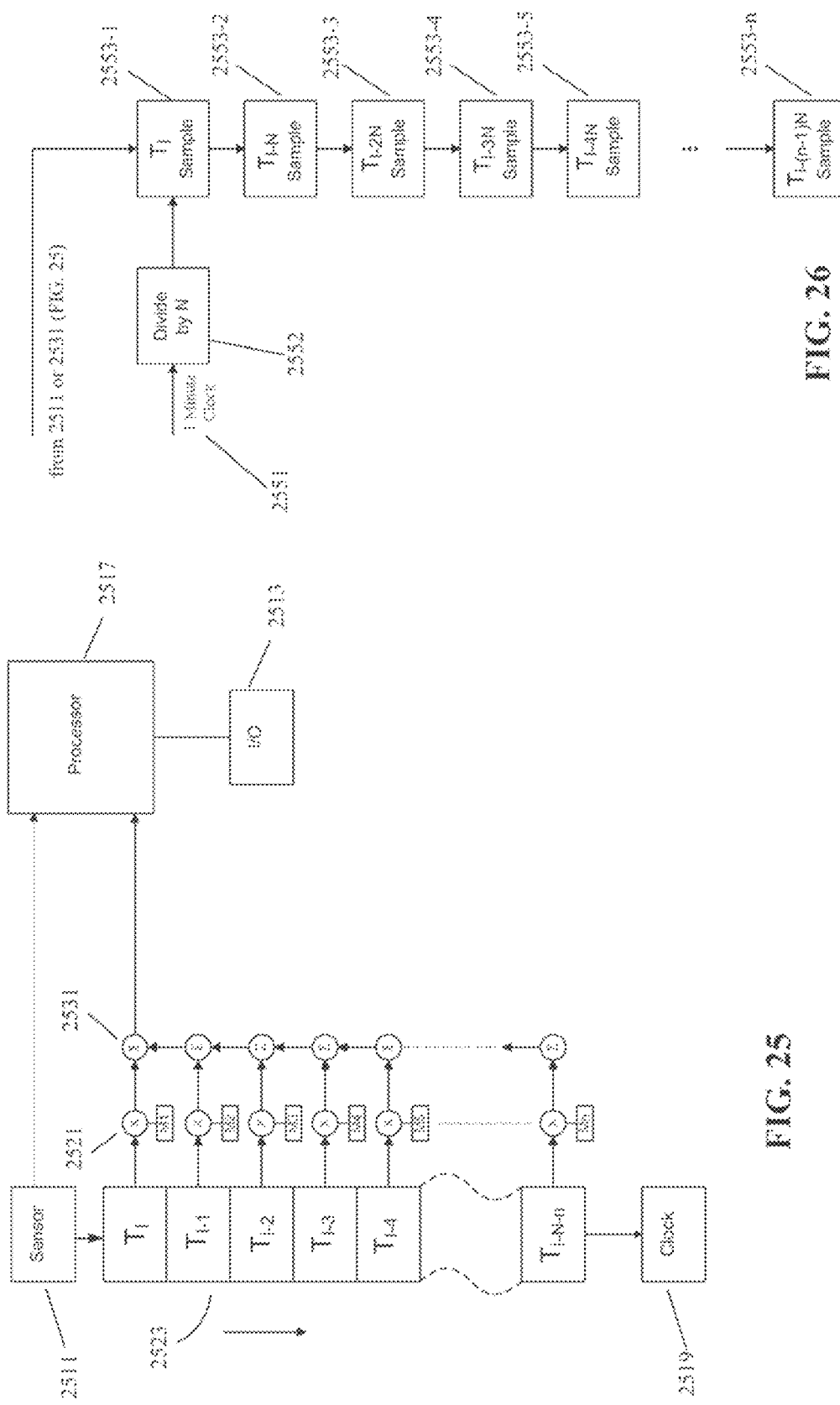
FIGS. 25-26 are functional block diagrams illustrating analyte sensor data processing routines in certain embodiments.

Referring back to the Figures, an exemplary implementation of the on body electronics adapted to process signals from the analyte sensor and to provide the processed or raw signals to the display device in response to such data request or upon demand is shown in FIG. 25. Referring to FIG. 25, there are provided a sensor 2511, clock 2519, processor 2517 and input/output (I/O) interface 2513. The functions of the memory are performed in part by shift register 2523. Shift register 2523 provides storage locations for n measurements from most current measurement Tl to the nth past measurement Tl-(n−1). Each storage location Tl-*x* provides an output into a multiplier, each configured to input a multiplicative weighting factor MX (2521). Each multiplier product is input into a corresponding summer 1, and the summers are chained to provide a composite weighted sum (weighted average) in summer (2531). Processor 2517 may also be adapted to read the individual values Tl to Tl-(n–1), and possibly individual sums. The multiplicative weighing factors may also be adjustable through processor 2517, responsive to two-way communications from a commanding device such as the display device 120 (FIG. 1). In certain embodiments a weighing factor in binary form may be used, which could be adjusted by a series of left or right shifts. This implementation might further include a similar (but likely smaller) additional shift register-multiplier-summer structure (not shown) to store a sequence of averages from summer 1, and provide a moving average of those averages, whose values and averages would be likewise provided to processor 2517.

Certain embodiments may be used to efficiently determine, store and provide upon request, the real time monitored analyte data, averaged analyte data and/or rate-of-change information of the monitored analyte. For example, a moving average may be used to indicate a trend in the monitored analyte level. If, for example, there were four storage elements (n=4), receiving shifted-in analyte measurement data once per minute, a multiplier of 1/n (e.g., ¼) may be used, in which case the trend or variation in the monitored analyte level may be regarded as the average of the past four samples. In another example, trend data might be the average of the third and fourth samples, in which case the weighing factors would be 0, 0, ½ and ¹A. In one embodiment, there may be 15 storage elements (with sensor data again collected once per minute), with two calculated trends—the first over the past 10 minutes and the second over the full 15 minutes. In addition on body electronics may store selected data on a long term basis, for example once every 15 or 20 minutes, for an extended wear period of on body unit 1 (e.g., up to several weeks).

Other approaches involving the determination of the analyte level and/or trend information or like or analogous components used for the same will be apparent to those of skill in the art. For example, the first location and the second location may be the same, e.g., data is overwritten. FIG. 26 shows a further memory structure that may be employed, which stores long term data at a slower sampling rate (short term trend vs. long term history). In one embodiment, clock signal 2551, e.g., a one-minute clock, may be divided by N in clock divider 2552. N may be any desired number, for example, 5, 10, 15, 20, 60 or other desired value in order to generate the desired time base for measurements. In certain embodiments, an analyte measurement may be determined (and not immediately provided to the display device), and stored in a memory or storage location. In one embodiment, an n-position shift register may be employed for this purpose, in which each measurement 2553-1, etc. to 2553-*n* is sequentially entered and shifted in the shift register. The most recent measurement at any time will be 2553-1. Alternatively, the memory or storage employed for this purpose may be addressable, and used as a circular buffer, with a pointer to the most recent measurement value. In certain embodiments (not shown), two or more sections as illustrated in FIG. 26 may be cascaded, to provide a plurality of further spaced apart measurements, e.g., over a period of hours.

FIGS. 27A-27D illustrate routines to determine periodic and/or averaged and/or rate-of-change data from monitored analyte level in analyte monitoring system 100 of FIG. 1. Referring to the Figures, a time or a series of times for taking sensor measurements may be derived from clock pulses, and separate measurements taken at such time or times (2710). In certain embodiments, a series of measurements (2715) may be digitized and directly recorded (2720, 2725). In other embodiments, a calculation, such as a rolling average of measurements, may be performed (2720) and the resulting value recorded (2725). In either case, at least one element (e.g., a measurement or an average) may be recorded or stored in a memory location of a memory device in on body electronics 110. A second computation may then be performed based upon the stored value(s), and the results of the computation again stored (e.g., each new analyte measurement may be accompanied by the further calculation (2720) of an updated average value or rate data). This process may be repeated continuously (e.g., returning to 2710), such that at any time there may be stored in on body electronics 110, or other storage device, whatever data is of interest, e.g., a sequence of measurements, a sequence of averages, and/or a current moving average of some number (n) of prior measurements.

Responsive to a user command (by actuation of a switch on the display device 120 (FIG. 1) or by positioning the display device 120 (FIG. 1) within a predetermined distance to on body electronics 110 (2730), the monitored analyte level information from the analyte sensor is provided to display device 120. In some embodiments, the user command is a user input, such as pressing a button or an actuator. In other embodiments, the user command includes both placing the display device 120 and on body electronics 110 within a defined communication range as well providing a user input.

Figure 27A:
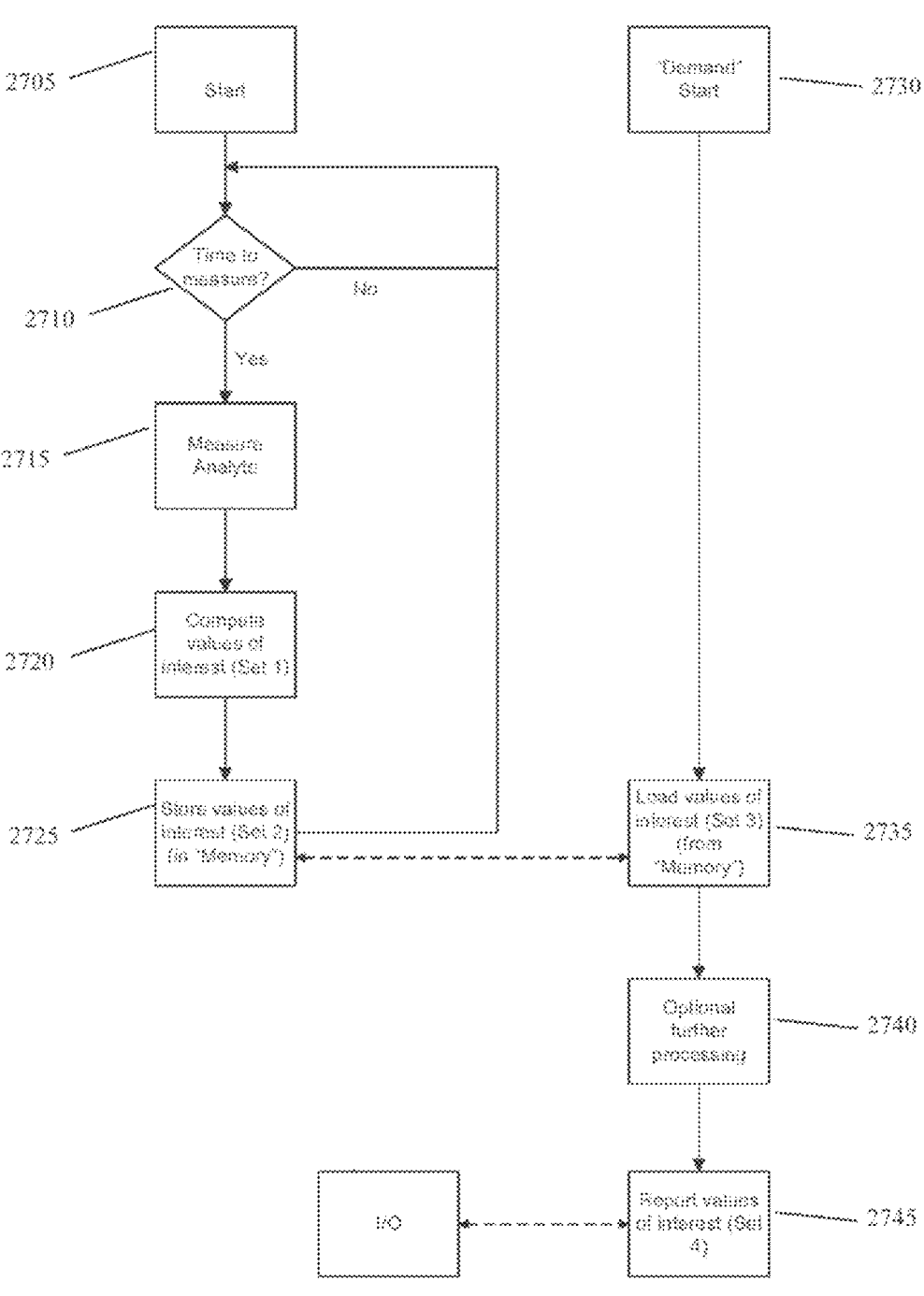
FIGS. 27A-27D are flowcharts illustrating analyte sensor data processing routines in certain embodiments.
Figure 27B:
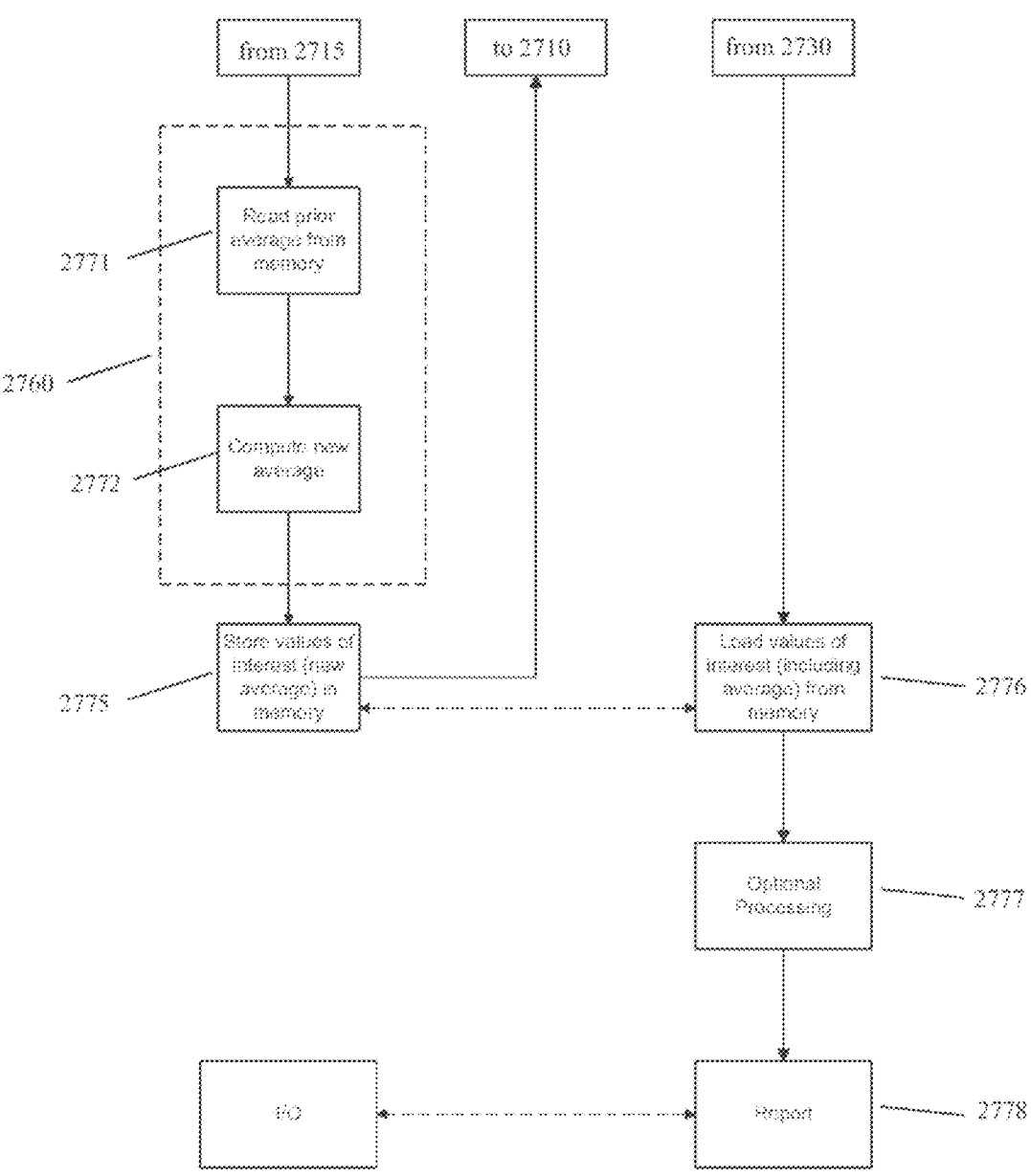

Referring now to FIGS. 27A and 27B, in certain embodiments, after starting or initiating the data processing routine (2705), a processor or programmed logic of the on body electronics 110 (FIG. 1) may be configured to verify one or more signals from a clock and determine, (2710), whether it was time to take a sensor measurement. If yes, then analyte sensor 101 reading is acquired by on body electronics 110 (2715). This value could be used as is (a measurement point), or processed in some manner (e.g., to calculate an updated rolling average based on a past rolling average), and the result (from 2720) stored in a memory location in the on body electronics 110 (2725). The measurement or rolling average points will be referred to as data set 1, and the stored data will be referred to as data set 2. The process may repeat in a loop (2710). In embodiments in which a plurality of storage locations is provided, new values are continuously stored, and the oldest values deleted or de-referenced.

At any time unrelated to the state of cycling of loop 2710-2725, a user may initiate a data request (2730). This will start a sub-process in which one or more values of interest may be loaded from the storage of data set 2 (2735). The selection, which may or may not be a different set, will be referred to as data set 3. Data set 3 may be subjected to optional further processing within on body electronics 110 (2740). For example, where data set 2 is a sequence of periodic analyte measurements the routine includes calculating a weighted moving average of the measurements and/or filtering, or the like (2740). The data set 3 data is reported to display device 120 (2745) with the I/O component. For example, the data set 3 data could include a series of periodic sensor measurements plus moving average data. As shown in FIG. 27B, the routine may also include a new average of the monitored analyte level determination (2760). A prior average may be read from the memory (2771) and a new average may be computed (2772), which may then be stored in the memory (2775) and returns to step 2710. From the user-initiated data request (2730), the stored values from 2775 are loaded (2776). The loaded values may be subjected to optional further processing (2777) and then reported (2778) using the I/O component.

Figure 27C:
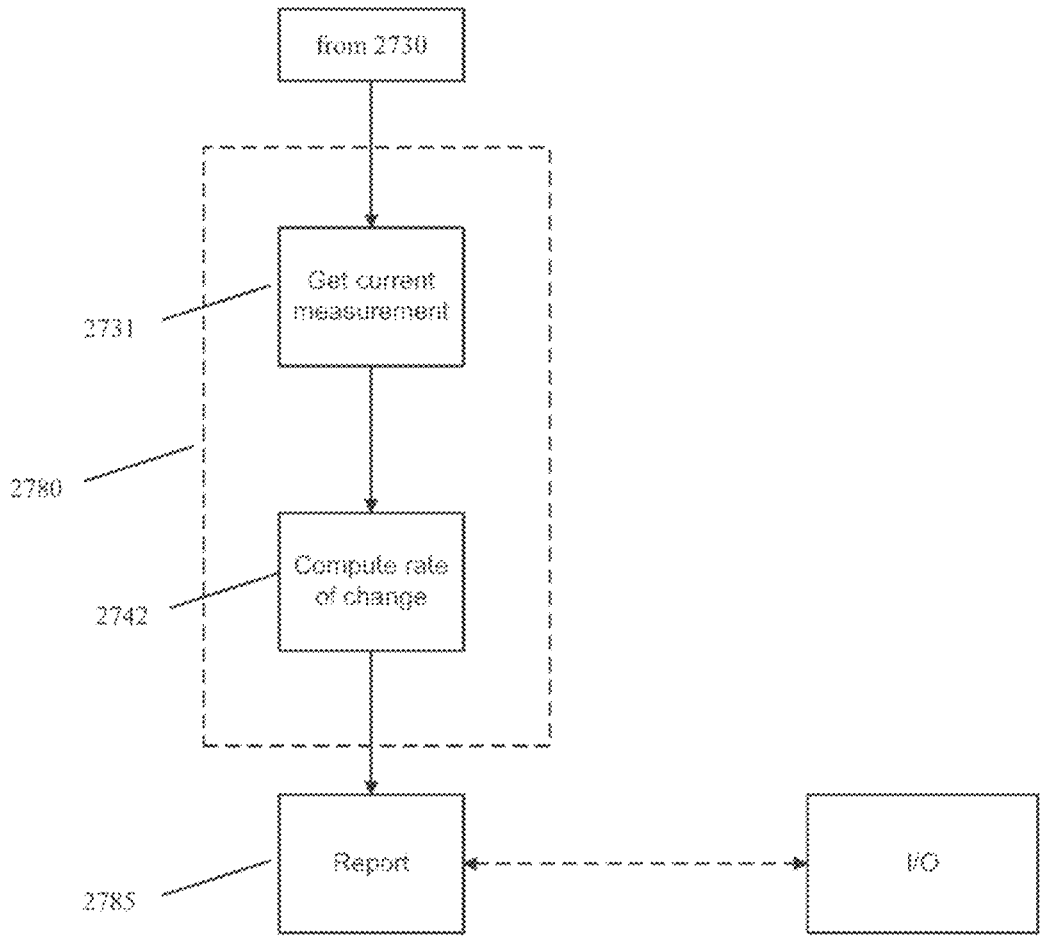
Figure 27D:
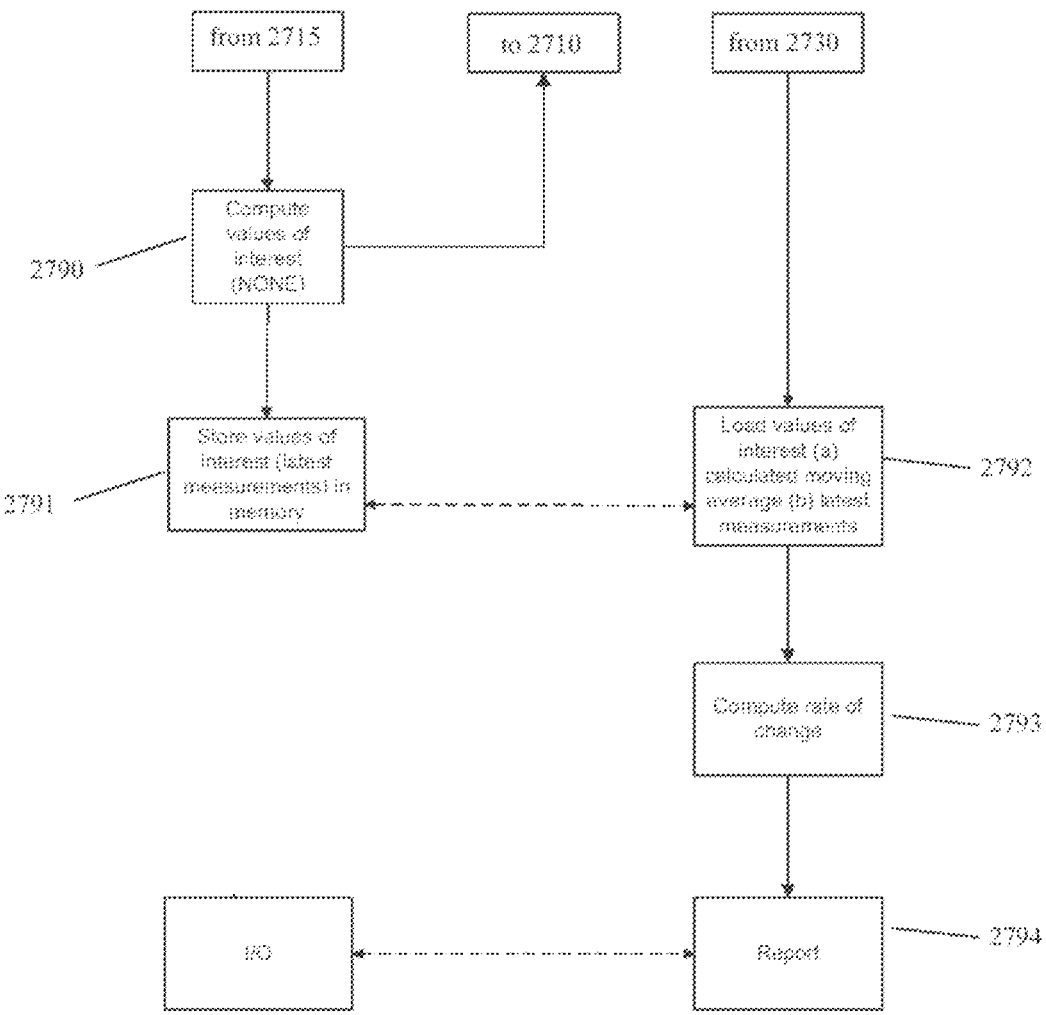

As shown in FIG. 27C, the routine may also include a rate-of-change of the monitored analyte level determination (2780). For example, a current analyte sensor measurement may be retrieved (2731), based on which a rate-of-change information of the monitored analyte level may be determined (2742) and reported (2785) with the I/O component. For example, referring to FIG. 27D, data set 2 may be the same as data set 1 (2790), and includes a set of periodic analyte measurements, which are stored (2791). Referring again to the Figure, the most current analyte measurement and a moving average are determined (2792), computing a rate of change on that basis (2793) and reporting the data (2794) using the I/O component. Within the scope of the present disclosure, different rates may be provided by comparison to averages determined in different ways or over a different number of measurements.

Where a plurality of storage elements are used, for instance, n elements, storing a data element could be accompanied by freeing the space occupied by the nth previously recorded element, for example by overwriting data, physically shifting data in a register, pushing or popping data from a stack structure, queuing or dequeuing data from a queue, or by changing pointers into a memory area in some other manner.

In embodiments in which averages are calculated, the averages may be weighted averages. In a simple case, the weighting factors could all be equal. Alternatively, certain factors could be reduced to zero in order to eliminate one or more measurements. Alternatively, weighting factors could be varied to attenuate or emphasize data from specific points in time. In some embodiments, where the data of interest is a sequence of measurements, the second calculation referred to above could be bypassed by simply using the first values recorded (e.g., without calculating or storing an average).

Where an average has been calculated and recorded or stored, a further calculation may be performed and the results used for further processing and/or communicating the results to another device or remote location, reflecting a further calculation performed on a current measurement and the average. For example, comparison of a current reading with a stored moving average would be a value indicative of the current analyte level rate of change or analyte data trend information. Additionally, successive rate-of-change figures may be recorded or stored in order to provide for the calculation of a moving average rate-of-change that might be less noisy than an instantaneous figure based on a single measurement compared to an average.

Figure 28:
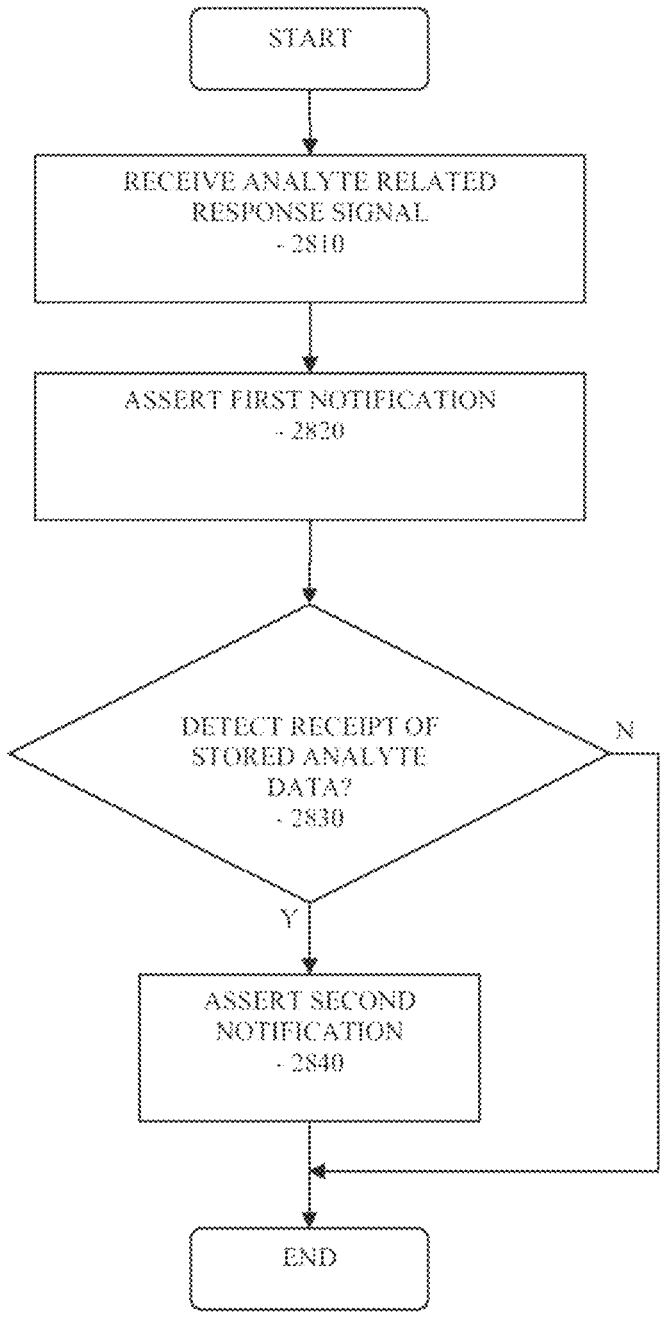
FIG. 28 is a flowchart illustrating analyte sensor data acquisition notification routine in certain embodiments.

FIG. 28 is a flowchart illustrating a glucose data acquisition notification routine in certain embodiments. Referring to FIG. 28, in one aspect, the display device 120 (FIG. 1) or a similar controller or data processing device may be configured to generate an output notification such as audible, vibratory, visual, or one or more combination notifications to indicate a successful glucose data acquisition received from the on body electronics 110 (FIG. 1) in signal communication with an analyte sensor such as a glucose sensor. That is, referring to FIG. 28, upon receipt of the analyte related response signal or data packet (2810), the display device 120 generates and asserts a first notification (2820) which may be a short audible tone. In certain embodiments, the first notification may be programmed in display device 120, or may be programmable by the user with customized output alert such as a ring tone, or a visual output (for example, a flashing indication on the screen of the display device)

representing successful real time glucose data acquisition or receipt from the on body electronics 110. In certain embodiments, receipt of the analyte related response signal or data packet (2810) is received in response to a request for the real time analyte data using, for example, RFID techniques, to acquire data in response to a data request (e.g., on demand).

In certain embodiments, the first notification may be programmed to be automatically asserted when the desired glucose data is received when the display device 120 is positioned within the predetermined distance from the on body electronics 110 to receive the backscatter signal from the on body electronics 110.

Referring again to FIG. 28, after the assertion of the first notification, it is determined whether stored analyte data is subsequently or concurrently received with the real time glucose data (2830). That is, in one aspect, in addition to the glucose data received from the on body electronics 110, display device 120 may be configured to receive additional glucose related information such as stored prior glucose data, sensor related data, such as sensor manufacturing code, calibration information, sensor status, device operational status information, updated battery life status of the device or any other information that may be provided to the display device 120 from the on body electronics 110. In aspects of the present disclosure, the additional or other information detected by the display device 120 including, for example, stored prior analyte data may be received after the real time glucose data acquisition. Alternatively, this additional data may be received concurrent or substantially contemporaneous to the receipt of the real time glucose data.

When the receipt of stored analyte data and/or other additional information is detected (2830), display device 120 in one aspect of the present disclosure may be configured to assert a second notification (2840) such as an audible alarm, alert, output tone, a ring tone, a vibratory indication, a visual output indication, or one or more combinations of the above to notify the user that the additional information has been successfully acquired or received by the display device 120. On the other hand, if it is determined that the additional information is not received by the display device 120, then the routine terminates.

In certain aspects, the assertion of the first notification and/or the second notification depends upon the duration of positioning the display device 120 in close proximity and within the short RF range of the on body electronics 110. That is, when the display device 120 is positioned within the communication range of the on body electronics 110 to transmit the request for glucose data, and in response, receives a responsive data packet including the real time glucose information, the display device 120 alerts the user with the first notification to confirm and/or notify the user that the real time glucose data has been successfully acquired or received from the on body electronics 110. Thereafter, if the display device 120 is maintained within substantially the same distance or closer to the on body electronics 110 for an extended or further time period, and the display device 120 detects the receipt of additional information or data packets from the on body electronics 110 (including, for example, historical or stored prior glucose related information), the display device 120 in one embodiment asserts the second notification or alert to the user to confirm and/or notify that additional information has been successfully received from the on body electronics 110.

In this manner, by positioning the display device 120 within a predetermined distance to the on body electronics 110, the user can receive or acquire real time and/or optionally historical glucose data and provided with confirmation notification of successful data acquisition, for example, with a first notification indicating successful real time glucose data acquisition, and a second notification indicating successful data acquisition of additional glucose or device related data. In certain embodiments, the first and second notifications may be the same, or different in characteristics. For example, in the embodiment where the notifications are audible tones, each of the first and second notifications may have different tone duration, pitch, and the like. Alternatively, the first and second notifications may share one or more characteristics (such as the pitch), but with at least one unique characteristic (such as duration of the tone), such that the two notifications can be distinguished. Furthermore in accordance with aspects of the present disclosure, additional notifications may be programmed or provided to the display device 220 (or customized by the user) to include, for example, multiple output notifications each associated with a particular data acquisition mode or event.

Figure 29:
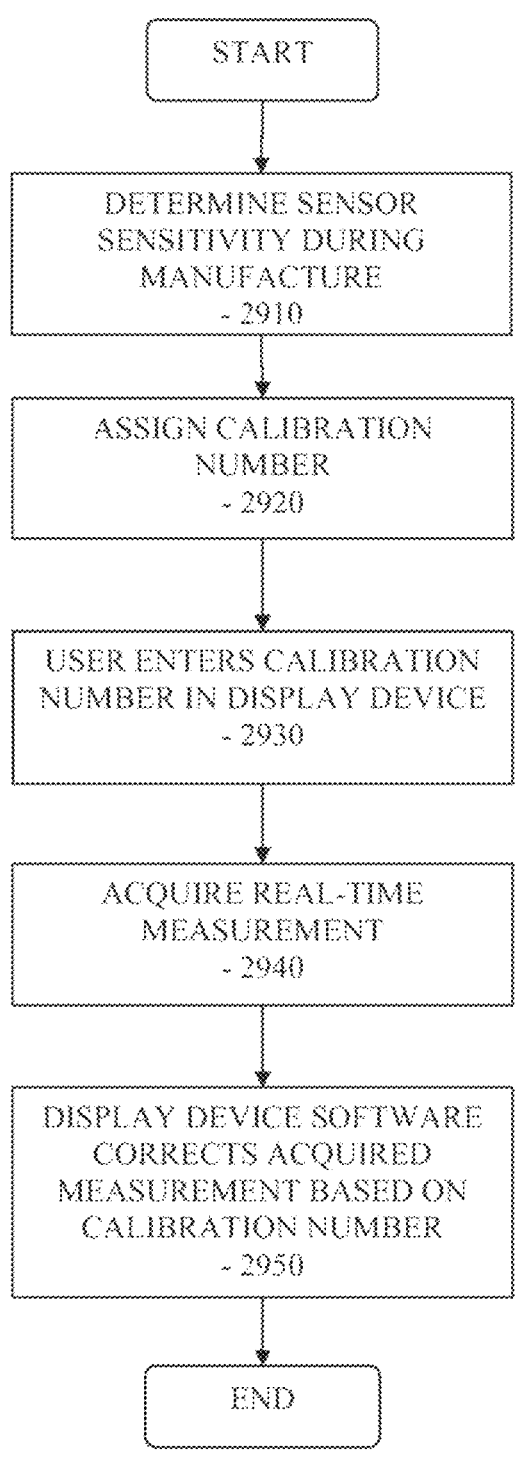
FIG. 29 is a flowchart illustrating manufacturing based analyte sensor calibration implemented in sensor data processing in certain embodiments.

In certain embodiments, analyte monitoring systems may be calibrated as part of manufacturing and shipped as already calibrated. FIG. 29 is a flowchart illustrating sensor calibration achieved as part of manufacturing in certain embodiments. Referring to FIG. 29, a determination of sensor sensitivity is performed during manufacture (2910). A calibration number is then assigned in connection with the sensor sensitivity determined during manufacture (2920). Then the user is instructed to enter, and in response thereto enters, the calibration number into the receiver unit (such as the display device 120 of FIG. 1) (2930). Using the sensor sensitivity information associated with the calibration number, after receiving analyte sensor measurement (2940), the display device processes the analyte sensor measurement data in conjunction with the sensor sensitivity information to calibrate the analyte monitoring system (2950).

In certain embodiments, the analyte monitoring system may be calibrated as part of manufacturing and may require no user calibration. In other embodiments, the analyte monitoring system may not require any calibration, including factory calibration. Further detailed description regarding analyte sensors and sensor systems that do not require calibration by human intervention is provided in U.S. patent application Ser. No. 12/714,439, the disclosure of which is incorporated herein by reference in its entirety for all purposes. Moreover, further details related to calibration and obtaining system measurements of continuous analyte monitoring systems can be found in, for example, U.S. Publication Nos. 2009/0005665, now U.S. Pat. No. 8,444,560; 2008/0288204, now U.S. Pat. No. 9,204,827; 2008/0006034, now U.S. Pat. No. 7,772,453; 2008/0255808, now U.S. Pat. No. 8,140,142; 2008/0256048, now U.S. Pat. No. 9,615,780; 2009/0006034, now U.S. Pat. No. 10,002,233; 2008/0312842, now U.S. Pat. No. 8,239,166; 2008/0312845; 2008/0312844, now U.S. Pat. No. 7,996,158; 2008/0255434, now U.S. Pat. No. 9,008,743; 2008/0287763, now U.S. Pat. No. 9,125,548; 2008/0281179; 2008/0288180, now U.S. Pat. No. 8,260,558; 2009/0033482, now U.S. Pat. No. 7,768,386; 2008/0255437, now U.S. Pat. No. 10,111,608; and 2009/0036760; and U.S. Provisional Application No. 61/247,508, the disclosures of each of which are incorporated in their entirety by reference for all purposes.

In certain embodiments, calibration of the analyte sensor by human intervention is not required, and therefore not performed prior to the output of clinically accurate analyte data. For example, the tolerances achieved during manufacturing and/or stability of a given sensor over time may be such that calibration by human intervention is not required, see for example, U.S. patent Application Ser. No. 11/322,165, now U.S. Pat. No. 8,515,518, 11/759,923, 61/155,889, 61/155,891, and 61/155,893, the disclosures of each of which are incorporated by reference in their entireties herein for all purposes.

Referring back to FIG. 1, in certain embodiments, analyte monitoring system 100 may store the historical analyte data along with a date and/or time stamp and/or and contemporaneous temperature measurement, in memory, such as a memory configured as a data logger as described above. In certain embodiments, analyte data is stored at the frequency of about once per minute, or about once every ten minutes, or about once an hour, etc. Data logger embodiments may store historical analyte data for a predetermined period of time, e.g., a duration specified by a physician, for example, e.g., about 1 day to about 1 month or more, e.g., about 3 days or more, e.g., about 5 days or more, e.g., about 7 days or more, e.g., about 2 weeks or more, e.g., about 1 month or more.

Other durations of time may be suitable, depending on the clinical significance of the data being observed. The analyte monitoring system 100 may display the analyte readings to the subject during the monitoring period. In some embodiments, no data is displayed to the subject. Optionally, the data logger can transmit the historical analyte data to a receiving device disposed adjacent, e.g., in close proximity to the data logger. For example, a receiving device may be configured to communicate with the data logger using a transmission protocol operative at low power over distances of a fraction of an inch to about several feet. For example, and without limitation, such close proximity protocols include Certified Wireless USB™, TransferJet™, Bluetooth® (IEEE 802.15.1), WiFi™ (IEEE 802.11), ZigBee® (IEEE 802.15.4-2006), Wibree™, or the like.

The historical analyte data set may be analyzed using various diagnostic approaches. For example, the historical analyte data taken over several days may be correlated to the same date/and or time. The historical analyte data may be correlated to meal times. For example, data could take into account breakfast, lunch, and dinner. Data analysis for each meal could include some pre-prandial time (e.g. 1 or 2 hours) and some post-prandial time (e.g. 1-4 hours). Such an approach eliminates apparent glucose variability due to variability in the timing of meals alone. Analyte data parameters may be determined based upon the rate of change of one or more analyte levels. In some embodiments, an analyte data parameter may be determined concerning whether a threshold relating to an analyte value is exceeded, e.g., a hyper- or hypoglycemia condition, the percentage of time in which the threshold is exceeded, or the duration of time in which the threshold is exceeded.

The analyte data parameters may be computed by a processor executing a program stored in a memory. In certain embodiments, the processor executing the program stored in the memory is provided in data processing module 160 (FIG. 1). In certain embodiments, the processor executing the program stored in the memory is provided in display device 120. An exemplary technique for analyzing data is the applied ambulatory glucose profile (AGP) analysis technique.

Additional detailed descriptions are provided in U.S. Pat. Nos. 5,262,035; 5,264,104; 5,262,305; 5,320,715; 5,593,852; 6,175,752; 6,650,471; 6,746,582, 6,284,478, 7,299,082, and in U.S. patents application Ser. Nos. 10/745,878, now U.S. Pat. No. 7,811,231; Ser. No. 11/060,365, now U.S. Pat. No. 8,771,183, the disclosure of each of which are incorporated herein by reference.

As described above, in certain aspects of the present disclosure, discrete glucose measurement data may be acquired on-demand or upon request from the display device, where the glucose measurement is obtained from an in vivo glucose sensor transcutaneously positioned under the skin layer of a user, and further having a portion of the sensor maintained in fluid contact with the ISF under the skin layer. Accordingly, in aspects of the present disclosure, the user of the analyte monitoring system may conveniently determine real time glucose information at any time, using the RFID communication protocol as described above.

FIGS. 30A-30D illustrate embodiments of the analyte data acquisition module for use with display device 120 in certain embodiments. Referring to FIGS. 30A-30D, display device 120 may include an input mechanism such as a user actuatable button 3001 positioned on an outer surface of the housing of the display device 120. While the embodiment shown in FIG. 30C positions the button 3001 on the opposing surface of display device 120 as the location of display 122 (FIG. 1), in certain embodiments, the button 3001 may be positioned along any suitable axis along a length or a width dimension of display device 120, as long as the button 3001 can be easily accessed by either hands of the user to provide ambidextrous operation of button 3001. That is, in certain embodiments, display device 120 may be provided with an input mechanism such as user actuatable button 3001 positioned on its housing such that the button is within comfortable and convenient reach for activation, regardless of whether the display device 120 is held in the left hand or the right hand of the user.

For example, button 3001 may be positioned on the opposing surface of or the back housing of display device 120 such that it is located substantially equidistant from either side edges of the display device 120 housing. That is, in certain embodiments, the position of the button 3001 is substantially in alignment with the central longitudinal axis of the display device 120. In certain embodiments, button 3001 may be positioned along the upper outer peripheral edge surface of the display device 120 such that it is located at substantially the opposite location to the location of the strip port 124 on the display device 120. While several specific locations and positions of button 3001 are described above, within the scope of the present disclosure, button 3001 may be positioned in other suitable location of the display device 120, including, for example, on the same planar surface of the housing as display 122 of display device 120.

In certain embodiments, actuation of the button 3001 on display device 120 initiates one or more routines that are programmed in the display device 120. For example, actuation of button 3001 may initiate the routine for wireless turn on of the on body electronics 110 as described above. In certain embodiments, actuation of button 3001 executes the software routine to initiate data transfer request to acquire analyte related data from on body electronics 110 (FIG. 1), when the display device 120 is positioned within the predetermined distance from the on body electronics 110 to receive the data communication. In still other embodiments, actuation of button 3001 initiates the backlight function to illuminate the display 122 of display device 120. Button 3001 may also be programmed as a power on/off switch. Within the scope of the present disclosure, other functions of display device 120 may be associated with the actuation of button 3001.

Figure 30A:
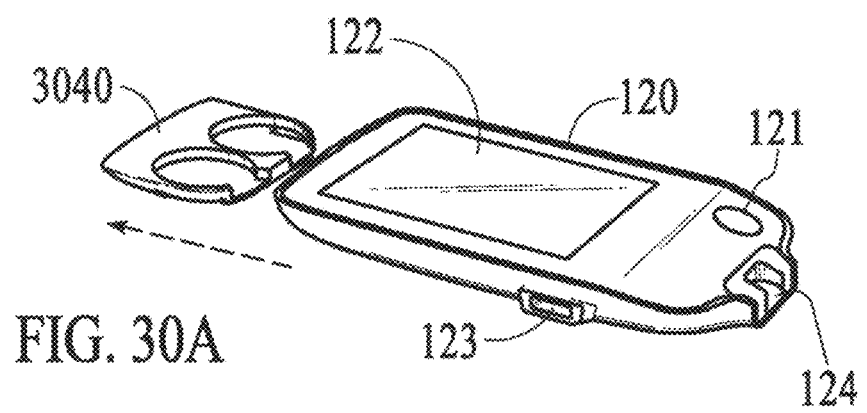
FIG. 30A-30D illustrates an embodiment of the analyte data acquisition module for use with a display device in certain embodiments.
Figure 30B:
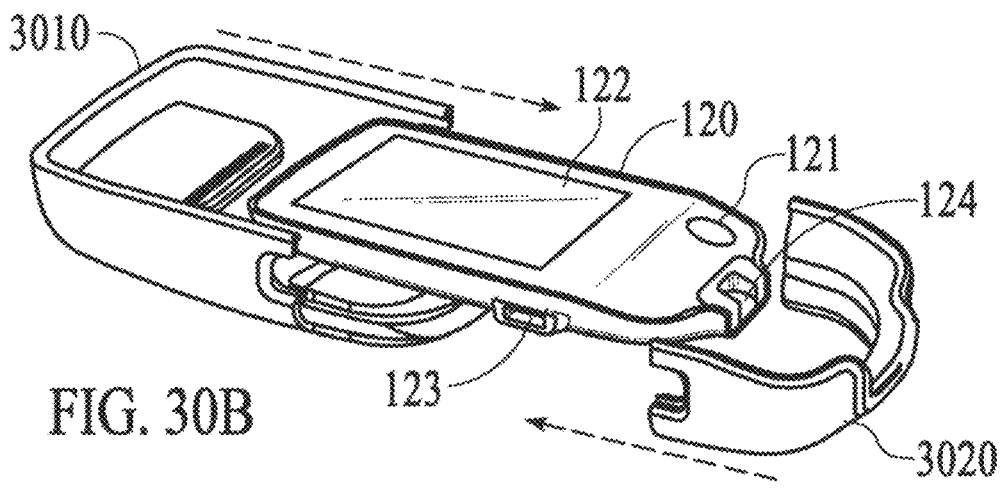
Figures 30C, 30D:
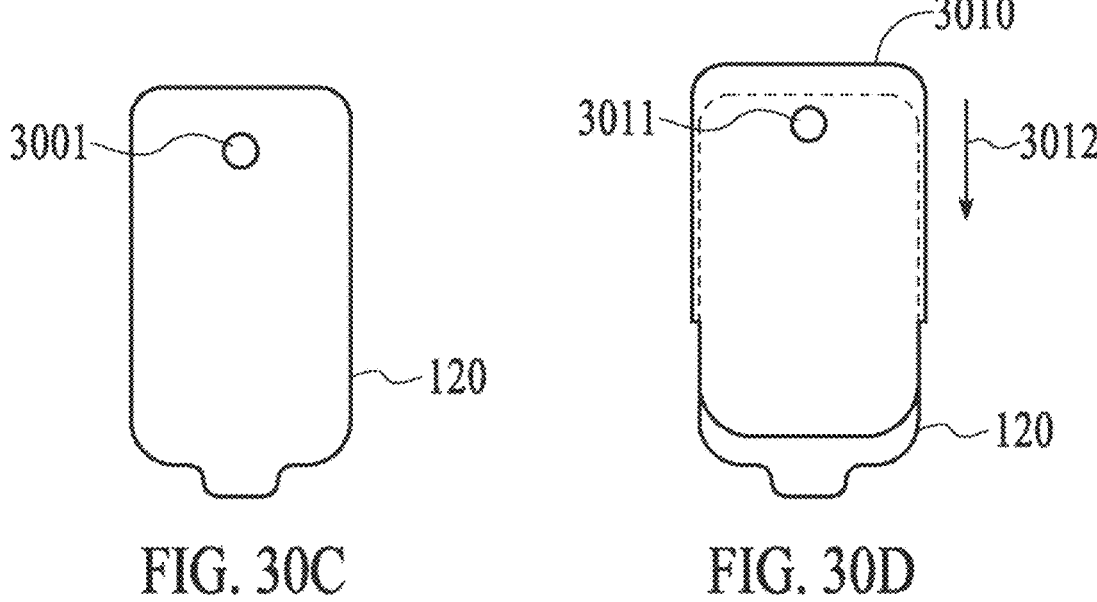

Referring back to FIGS. 30A-30D, in certain embodiments, a mateable sleeve 3010 may be provided to couple to the display device 120. The sleeve may include a second component 3020 to secure the mateable sleeve 3010 to the display device. In certain embodiments, electrical contact with display device 120 may be achieved by accessing the battery compartment of display device 120. More specifically, with battery compartment cover 3040 of display device 120 removed as shown in FIG. 30A, the exposed battery contacts of display device 120 may be connected to corresponding electrical contacts in sleeve 3010 when mated with display device 120. After mating with display device 120, actuation of button 3011 on the sleeve 3010 activates or initiates the routines similar to those discussed above in conjunction with button 3001 on the housing of display device 120. As shown in the Figures, in certain embodiments, the sleeve 3010 may be mated with display device 120 to electrically connect with the battery compartment contacts by securing the sleeve 3010 over one end of the display device 120 as shown and displaced in the direction indicated by directional arrow 3012. In certain embodiments, sleeve 3010 may be mated with display device 120 by applying pressure upon its surface against the display device 120 housing, and secure thereon in a snap fit manner. In certain other embodiments, magnetic force or other coupling mechanism may be used to mate the sleeve 3010 with the display device 120.

In certain embodiments, housing of the sleeve 3010 may be provided with processing electronics including antenna, storage device such as memory, and application logic and/or microprocessor for processing data and communicating with the on body electronics 110. Accordingly, when mated or coupled to another electronic device such as, for example, an in vitro glucose meter, the programmed routines and executable software stored in the sleeve 3010, for example, to communicate with on body electronics 110 in analyte monitoring system described above in conjunction with FIG. 1, glucose meter with the mated sleeve 3010 in certain embodiments may communicate with such devices by sharing the stored software routine in sleeve 3010 with one or more microprocessors of the in vitro glucose meter and executed or implemented by the glucose meter microprocessor(s).

Furthermore, when the user does not wish to use the sleeve 3010, it can be disabled or deactivated while engaged to display device 120 or removed from the display device by sliding or otherwise disengaging the module 3010 from the display device 120, e.g., moving it in the opposite direction from the directional arrow shown in 3012 or otherwise simply detaching the sleeve 3010 from display device 120.

In the manner described above, in accordance with various embodiments of the present disclosure, discrete glucose measurements may be obtained without the need for lancing or performing fingerprick test for access to blood sample each time a measurement is desired. The analyte monitoring system described in further aspects may be configured to log or store glucose data monitored by the analyte sensor continuously over a predetermined or programmable time period, or over the life of the sensor without user intervention, and which data may be retrieved at a later time as desired. Furthermore, output indications such as audible, visual or vibratory alerts may be provided to inform the user of a predetermined condition or when the monitored glucose level deviates from a predefined acceptable range (for example, as warning indication of low glucose or high glucose level).

In still another aspect, the methods, devices and systems described above may be configured to log and store (for example, with an appropriate time stamp and other relevant information such as, for example, contemporaneous temperature reading) the real time analyte data received from the analyte sensor, and may be configured to provide the real time analyte data on-demand by using, for example a device such as a blood glucose meter or a controller discussed above that is configured for communication with the on body integrated sensor and sensor electronics component.

That is, in one embodiment, real time data associated with the analyte being monitored is continuously or intermittently measured and stored in the integrated on body sensor and sensor electronics component, and upon request from another device such as the receiver unit or the display device 120 (operated by the user, for example) or any other communication enabled device such as a cellular telephone, a PDA, an internet or WiFi data network enabled smartphones, or any other suitable communication enabled device which may be used to receive the desired analyte data from the on body integrated sensor and sensor electronics component while being worn and used by the user. In one aspect, such communication enabled device may be positioned within a predetermined proximity to the integrated on body sensor and sensor electronics component, and when the communication enabled device is positioned within the predetermined proximity, the data from the integrated on body sensor and sensor electronics component may be provided to the communication enabled device. In one aspect, such data communication may include inductive coupling using, for example, electromagnetic fields, Zigbee® protocol based communication, or any other suitable proximity based communication techniques. In this manner, glucose on-demand mode may be provided such that the information associated with contemporaneously monitored analyte level information is provided to the user on-demand from the user.

In this manner, in certain embodiments, the size and dimension of the on body electronics may be optimized for reduction by, for example, flexible or rigid potted or low pressure/low temperature overmolded circuitry that uses passive and active surface mount devices for securely positioning and adhering to the skin surface of the user. When flexible circuitry is with or in the overmold, the on body electronics may include the analyte sensor and/or other physiological condition detection sensor on the flex circuit (or PCB). Furthermore in embodiments of the present disclosure, one or more printed RF antenna may be provided within the sensor electronics circuitry for RF communication with one or more remote devices, and further, the device operation and/or functionalities may be programmed or controlled using one or more a microprocessors, or ASICs to reduce the number of internal components.

Embodiments of the present disclosure include one or more low pressure molding materials that directly encapsulate the integrated circuits or the sensor electronic components. The thermal process entailed in the encapsulation using the low pressure molding materials may be configured to shield temperature sensitive components such as, for example, the analyte sensor or other components of the sensor electronics from the heat generated during the thermal overmolding process. Other techniques such as injection molding and/or potting may be used.

In another aspect, the sensor electronics may be molded using optical techniques such as with a UV cured material, for example, or using two photon absorption materials, which may also be used to reduce the dead or unused volume surrounding the sensor electronics within the housing of the device such that the reduction of its size and dimension may be achieved. Moreover, the sensor electronics may be configured to reduce the number of components used, for example, by the inclusion of an ASIC that may be configured to perform the one or more functions of discrete components such as a potentiostat, data processing/storage, thermocouple/thermistor, RF communication data packet generator, and the like. Additionally, a field programmable gate array (FPGA) or any other suitable devices may be used in addition to the ASIC in the sensor electronics to reduce the on body electronics dimension.

Also, embodiments of the present disclosure includes analyte sensors that may be fabricated from flex circuits and integrated with the sensor electronics within the device housing, as a single integrated device. Example of flex circuits may include evaporated or sputtered gold on polyester layer, single or multi-layer copper or gold on polyimide flex circuit. When the sensor fabricated from a copper or gold polyimide flex circuit, gold or other inert material may be selectively plated on the implantable portion of the circuit to minimize the corrosion of the copper. In certain embodiments, the flex circuit may be die or laser cut, or alternatively chemically milled to define the sensor from the flex circuit roll.

A further configuration of embodiments of the present disclosure includes RF communication module provided on the flex circuit instead of as a separate component in the on body electronics. For example, the RF antenna may be provided directly on the flex circuit by, such as surrounding the on body electronics components within the housing on the flex circuit, or folded over the components, and encapsulated with the electronic components within the housing of the on body electronics.

In one aspect, the integrated assembly including the on body electronics and the insertion device may be sterilized and packaged as one single device and provided to the user. Furthermore, during manufacturing, the insertion device assembly may be terminal packaged providing cost savings and avoiding the use of, for example, costly thermoformed tray or foil seal. In addition, the insertion device may include an end cap that is rotatably coupled to the insertion device body, and which provides a safe and sterile environment (and avoid the use of desiccants for the sensor) for the sensor provided within the insertion device along with the integrated assembly. Also, the insertion device sealed with the end cap may be configured to retain the sensor within the housing from significant movement during shipping such that the sensor position relative to the integrated assembly and the insertion device is maintained from manufacturing, assembly and shipping, until the device is ready for use by the user.

In certain embodiments, an integrated analyte monitoring device assembly comprises an analyte sensor for transcutaneous positioning through a skin layer and maintained in fluid contact with an ISF under the skin layer during a predetermined time period. The analyte sensor includes a proximal portion and a distal portion. The integrated analyte monitoring device assembly includes on body electronics coupled to the analyte sensor, the on body electronics comprising a circuit board having a conductive layer and a sensor antenna disposed on the conductive layer, one or more electrical contacts provided on the PCB and coupled with the proximal portion of the analyte sensor to maintain continuous electrical communication, and a data processing component provided on the circuit board and in signal communication with the analyte sensor. The data processing component may be configured to execute one or more routines for processing signals received from the analyte sensor, and to control the transmission of data associated with the processed signals received from the analyte sensor to a remote location using the sensor antenna in response to a request signal received from the remote location.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A printed circuit board disposed within an on-body electronics unit of a glucose monitoring system, the on-body electronics unit configured to be secured on a skin surface of a user, the printed circuit board comprising:

a first side having an application-specific integrated circuit (ASIC) affixed thereto, the ASIC positioned proximate an insertion needle hole of the printed circuit board;

a second side having a temperature sensor affixed thereto and a proximal portion of an electrochemical glucose sensor electrically affixed thereto via a fixed electrical coupling during manufacturing, wherein the electrochemical glucose sensor has a distal portion which extends at an angle of at least 80 degrees from the second side of the printed circuit board, the distal portion configured to maintain fluid contact with an interstitial fluid under a skin layer of the user;

a multiple-loop antenna electrically coupled to the ASIC, the multiple-loop antenna comprising a first portion and a second portion, the first portion having a conductive trace disposed between the first side and the second side of the printed circuit board and wound along a first section of the printed circuit board, and the second portion disposed on a second section of the printed circuit board, wherein the first section of the printed circuit board comprises a part of an outer periphery of the printed circuit board, and wherein the second section of the printed circuit board is different from the first section; and a battery electrically coupled to the printed circuit board proximate the outer periphery of the printed circuit board.

2. The printed circuit board of claim 1, wherein the second portion of the multiple-loop antenna extends away from the outer periphery and across the printed circuit board.

3. The printed circuit board of claim 1, wherein the multiple-loop antenna is electrically coupled to the ASIC on at least one of the first side or the second side of the printed circuit board.

4. The printed circuit board of claim 1, wherein the distal portion of the electrochemical glucose sensor extends downwards from the second side of the printed circuit board, and wherein the electrochemical glucose sensor bends to define an angle of at least 80 degrees between the proximal portion and the distal portion.

5. The printed circuit board of claim 4, wherein the proximal portion of the electrochemical glucose sensor extends parallel to the second side of the printed circuit board.

6. The printed circuit board of claim 1, wherein the distal portion extends at an angle of approximately 90 degrees from the second side of the printed circuit board.

7. The printed circuit board of claim 1, wherein the distal portion extends at an angle between 80 to 90 degrees from the second side of the printed circuit board.

8. The printed circuit board of claim 1, wherein the conductive trace is disposed on a substrate of the printed circuit board.

9. The printed circuit board of claim 1, wherein the conductive trace comprises a copper trace.

10. The printed circuit board of claim 1, wherein the on-body electronics unit is configured to be disabled after a predetermined useful life of the electrochemical glucose sensor.

* * * * *